United States Patent
Patel et al.

(10) Patent No.: US 10,421,805 B2
(45) Date of Patent: Sep. 24, 2019

(54) ANTI-HEPATITIS C ANTIBODIES AND ANTIGEN BINDING FRAGMENTS THEREOF

(71) Applicant: United Kingdom Research and Innovation, Swindon (GB)

(72) Inventors: Arvind Patel, Strathclyde (GB); Ania Owsianka, Strathclyde (GB)

(73) Assignee: United Kingdom Research and Innovation (GB)

( * ) Notice: Subject to any disclaimer, the term of this patent is extended or adjusted under 35 U.S.C. 154(b) by 0 days.

(21) Appl. No.: 15/507,676

(22) PCT Filed: Sep. 4, 2015

(86) PCT No.: PCT/GB2015/052558
§ 371 (c)(1),
(2) Date: Feb. 28, 2017

(87) PCT Pub. No.: WO2016/034891
PCT Pub. Date: Mar. 10, 2016

(65) Prior Publication Data
US 2017/0283484 A1 Oct. 5, 2017

(30) Foreign Application Priority Data
Sep. 5, 2014 (GB) .................................. 1415714.3

(51) Int. Cl.
| | |
|---|---|
| *C07K 16/10* | (2006.01) |
| *G01N 33/576* | (2006.01) |
| *C12Q 1/70* | (2006.01) |
| *A61K 39/42* | (2006.01) |
| *C07K 16/42* | (2006.01) |
| *A61K 39/00* | (2006.01) |

(52) U.S. Cl.
CPC ............ *C07K 16/109* (2013.01); *A61K 39/42* (2013.01); *C07K 16/4216* (2013.01); *C12Q 1/707* (2013.01); *G01N 33/5767* (2013.01); *A61K 39/00* (2013.01); *A61K 2039/505* (2013.01); *C07K 2319/02* (2013.01); *C07K 2319/40* (2013.01); *C12N 2770/24222* (2013.01)

(58) Field of Classification Search
None
See application file for complete search history.

(56) References Cited

FOREIGN PATENT DOCUMENTS

| | | |
|---|---|---|
| WO | WO2006100449 | 9/2006 |
| WO | WO2009061739 A1 | 5/2009 |
| WO | 2009/081285 A2 | 7/2009 |
| WO | 2009/081285 A3 | 7/2009 |
| WO | 2010/080528 A1 | 7/2010 |

OTHER PUBLICATIONS

Owsianka et al. (Journal of Virology, 2005, p. 11095-11104).*
Zhang Pei et al: "Hepatitis C virus epitope-specific neutralizing antibodies in Igs prepared from human plasma", Proceedings of the National Academy of Sciences, National Academy of Sciences, us ,vol. 104, No. 20, May 15, 2007 (May 15, 2007), pp. 8449-8454.
J. A. Potter et al: "Toward a Hepatitis C Virus Vaccine: the Structural Basis of Hepatitis C Virus Neutralization by AP33, a Broadly Neutralizing Antibody", Journal of Virology.,vol. 86, No. 23,Dec. 1, 2012 (Dec. 1, 2012) , pp. 12923-12932.
Kong Leopold et al: "Structure of Hepatitis C Virus Envelope Glycoprotein EI Antigenic Site 314-324 in Complex with Antibody IG", Journal of Molecular Biology,vol . 427, No. 16, Dec. 2015, pp. 2617-2628.
Giuseppe Sautto et al: "Structural and Antigenic Definition of Hepatitis C Virus E2 Glycoprotein Epitopes Targeted by Monoclonal Antibodies," Clinical & Developmental Immunology. vol. 8, No. 5, Jan. 1, 2013, pp. 1-12.
Lechner, Oskar, International Search Report, European Patent Office, dated Mar. 10, 2016.
Lechner, Oskar, Written Opinion of the International Searching Authority, European Patent Office, dated Mar. 10, 2016.
Kong, L. et al. "Structure of Hepatitis C Virus Envelope Glycoprotein E2 Antigenic Site 412 to 423 in Complex with Antibody AP33", Journal of Virology, vol. 86, No. 23, Dec. 2012, pp. 13085-13088.
Tarr, A.W. et al. "Characterization of the Hepatitis C Virus defined by the broadly neutralizing monoclonal antibody AP33", Hepatology, vol. 43 (3), Mar. 2006, pp. 592-601.
Kaye, Jeremy, Search Report, UK Int'l Patent Office, dated Sep. 30, 2015.

(Continued)

Primary Examiner — Agnieszka Boesen
(74) Attorney, Agent, or Firm — Thomas G. Peterson; Maynard Cooper & Gale

(57) ABSTRACT

The invention provides an antibody or antigen binding fragment thereof capable of binding to the antigen binding pocket of the $AP_{33}$ antibody, wherein said antibody or antigen binding fragment thereof comprises VL CDR1 (L1), VL CDR2 (L2), and VL $CDR_3$ ($L_3$) consisting of the amino acid sequences of SEQ ID NO:1, SEQ ID NO:2 and SEQ ID NO:23 respectively, and comprises VH CDR1 (H1), VH CDR2 (H2), and VH $CDR_3$ ($H_3$) consisting of the amino acid sequences of SEQ ID NO:24, SEQ ID NO:25, and SEQ ID NO:26 respectively. The invention also provides compositions, methods, nucleic acids and uses.

19 Claims, 13 Drawing Sheets
Specification includes a Sequence Listing.

(56) References Cited

OTHER PUBLICATIONS

Lopez-Diaz De Cerio, A., et al, "Anti-idiotype antibodies in cancer treatment," Oncogene, vol. 26, pp. 3594-3602, 2007.
Christensen, Neil D., et al., "Induction of Neutralizing Antibodies to Papillomaviruses by Anti-idiotypic Antibodies," Virology, vol. 210, pp. 292-301, Apr. 24, 1995.
Venturini, Anja Colja, et al., "Anti-idiotypic antibodies: a new approach in prion research," BMC Immunology, vol. 10, No. 16, Mar. 19, 2009.
Lopez-Requena, Alejandro, et al., "Idiotype as immungens: facing the challenge of inducing strong therapeutic immune responses against the variable region of immunoglobulins," Frontiers in Oncology, vol. 2, No. 159, Nov. 2012.

* cited by examiner

Absorbance (A450)

(a) AP33

(b) AP33 LC (c) AP33 HC & another κ-chain

FIGURE 5

```
GCCAGCCCCCTGATGGGGGCGACACTCCACCATGAATCACTCCCCTGTGAGGAAC    55

TACTGTCTTCACGCAGAAAGCGTCTAGCCATGGCGTTAGTATGAGTGTCGTGCAG   110

CCTCCAGGACCCCCCCTCCCGGGAGAGCCATAGTGGTCTGCGGAACCGGTGAGTA   165

CACCGGAATTGCCAGGACGACCGGGTCCTTTCTTGGATAAACCCGCTCAATGCCT   220

GGAGATTTGGGCGTGCCCCCGCAAGACTGCTAGCCGAGTAGTGTTGGGTCGCGAA   275

AGGCCTTGTGGTACTGCCTGATAGGGTGCTTGCGAGTGCCCCGGGAGGTCTCGTA   330
                        ┌─► Core
                         M   S   T   N   P   K   P   Q   R   K   T     11
            GACCGTGCACC ATG AGC ACG AAT CCT AAA CCT CAA AGA AAA ACC   374

K   R   N   T   N   R   R   P   Q   D   V   K   F   P            25
AAA CGT AAC ACC AAC CGT CGC CCA CAG GAC GTC AAG TTC CCG           416

G   G   G   Q   I   V   G   G   V   Y   L   L   P   R            39
GGT GGC GGT CAG ATC GTT GGT GGA GTT TAC TTG TTG CCG CGC           458

R   G   P   R   L   G   V   R   A   T   R   K   T   S            53
AGG GGC CCT AGA TTG GGT GTG CGC GCG ACG AGG AAG ACT TCC           500

E   R   S   Q   P   R   G   R   R   Q   P   I   P   K            67
GAG CGG TCG CAA CCT CGA GGT AGA CGT CAG CCT ATC CCC AAG           542

A   R   R   P   E   G   R   T   W   A   Q   P   G   Y            81
GCA CGT CGG CCC GAG GGC AGG ACC TGG GCT CAG CCC GGG TAC           584

P   W   P   L   Y   G   N   E   G   C   G   W   A   G            95
CCT TGG CCC CTC TAT GGC AAT GAG GGT TGC GGG TGG GCG GGA           626

W   L   L   S   P   R   G   S   R   P   S   W   G   P           109
TGG CTC CTG TCT CCC CGT GGC TCT CGG CCT AGC TGG GGC CCC           668

T   D   P   R   R   R   S   R   N   L   G   K   V   I           123
ACA GAC CCC CGG CGT AGG TCG CGC AAT TTG GGT AAG GTC ATC           710

D   T   L   T   C   G   F   A   D   L   M   G   Y   I           137
GAT ACC CTT ACG TGC GGC TTC GCC GAC CTC ATG GGG TAC ATA           752

P   L   V   G   A   P   L   G   G   A   A   R   A   L           151
CCG CTC GTC GGC GCC CCT CTT GGA GGC GCT GCC AGG GCC CTG           794

A   H   G   V   R   V   L   E   D   G   V   N   Y   A           165
GCG CAT GGC GTC CGG GTT CTG GAA GAC GGC GTG AAC TAT GCA           836

T   G   N   L   P   G   C   S   F   S   I   F   L   L           179
ACA GGG AAC CTT CCT GGT TGC TCT TTC TCT ATC TTC CTT CTG           878
                                                  ┌─► E1
 A   L   L   S   C   L   T   V   P   A   S   Y   Q              193
GCC CTG CTC TCT TGC CTG ACT GTG CCC GCT TCA GCC TAC CAA           920
```

FIGURE 5 CONT

```
    V   R   N   S   S   G   L   Y   H   V   T   N   D   C   207
   GTG CGC AAT TCC TCG GGG CTT TAC CAT GTC ACC AAT GAT TGC  962

P   N   S   S   I   V   Y   E   A   A   D   A   I   L   221
   CCT AAC TCG AGT ATT GTG TAC GAG GCG GCC GAT GCC ATC CTG 1004

H   T   P   G   C   V   P   C   V   R   E   G   N   A   235
   CAC ACT CCG GGG TGT GTC CCT TGC GTT CGC GAG GGT AAC GCC 1046

S   R   C   W   V   A   V   T   P   T   V   A   T   R   249
   TCG AGG TGT TGG GTG GCG GTG ACC CCC ACG GTG GCC ACC AGG 1088

D   G   K   L   P   T   T   Q   L   R   R   H   I   D   263
   GAC GGC AAA CTC CCC ACA ACG CAG CTT CGA CGT CAT ATC GAT 1130

L   L   V   G   S   A   T   L   C   S   A   L   Y   V   277
   CTG CTT GTC GGG AGC GCC ACC CTC TGC TCG GCC CTC TAC GTG 1172

G   D   L   C   G   S   V   F   L   V   G   Q   L   F   291
   GGG GAC CTG TGC GGG TCT GTC TTT CTT GTT GGT CAA CTG TTT 1214

T   F   S   P   R   R   H   W   T   T   Q   D   C   N   305
   ACC TTC TCT CCC AGG CGC CAC TGG ACG ACG CAA GAC TGC AAT 1256

C   S   I   Y   P   G   H   I   T   G   H   R   M   A   319
   TGT TCT ATC TAT CCC GGC CAT ATA ACG GGT CAT CGC ATG GCA 1298

W   D   M   M   M   N   W   S   P   T   A   A   L   V   333
   TGG GAT ATG ATG ATG AAC TGG TCC CCT ACG GCA GCG TTG GTG 1340

V   A   Q   L   L   R   I   P   Q   A   I   M   D   M   347
   GTA GCT CAG CTG CTC CGG ATC CCA CAA GCC ATC ATG GAC ATG 1382

I   A   G   A   H   W   G   V   L   A   G   I   A   Y   361
   ATC GCT GGT GCT CAC TGG GGA GTC CTG GCG GGC ATA GCG TAT 1424

F   S   M   V   G   N   W   A   K   V   L   V   V   L   375
   TTC TCC ATG GTG GGG AAC TGG GCG AAG GTC CTG GTA GTG CTG 1466
                                        ┌──► E2
    L   L   F   A   G   V   D   A   E   T   H   V   T   G   389
   CTG CTA TTT GCC GGC GTC GAC GCG GAA ACC CAC GTC ACC GGG 1508

G   N   A   G   R   T   T   A   G   L   V   G   L   L   403
   GGA AAT GCC GGC CGC ACC ACG GCT GGG CTT GTT GGT CTC CTT 1550

T   P   G   A   K   Q   N   I   Q   L   I   N   T   N   417
   ACA CCA GGC GCC AAG CAG AAC ATC CAA CTG ATC AAC ACC AAC 1592

G   S   W   H   I   N   S   T   A   L   N   C   N   E   431
   GGC AGT TGG CAC ATC AAT AGC ACG GCC TTG AAT TGC AAT GAA 1634

S   L   N   T   G   W   L   A   G   L   F   Y   Q   H   445
   AGC CTT AAC ACC GGC TGG TTA GCA GGG CTC TTC TAT CAA CAC 1676
```

FIGURE 5 CONT

```
      K   F   N   S   S   G   C   P   E   R   L   A   S   C   459
     AAA TTC AAC TCT TCA GGC TGT CCT GAG AGG TTG GCC AGC TGC 1718

R   R   L   T   D   F   A   Q   G   W   G   P   I   S   473
     CGA CGC CTT ACC GAT TTT GCC CAG GGC TGG GGT CCT ATC AGT 1760

Y   A   N   G   S   G   L   D   E   R   P   Y   C   W   487
     TAT GCC AAC GGA AGC GGC CTC GAC GAA CGC CCC TAC TGC TGG 1802

H   Y   P   P   R   P   C   G   I   V   P   A   K   S   501
     CAC TAC CCT CCA AGA CCT TGT GGC ATT GTG CCC GCA AAG AGC 1844

V   C   G   P   V   Y   C   F   T   P   S   P   V   V   515
     GTG TGT GGC CCG GTA TAT TGC TTC ACT CCC AGC CCC GTG GTG 1886

V   G   T   T   D   R   S   G   A   P   T   Y   S   W   529
     GTG GGA ACG ACC GAC AGG TCG GGC GCG CCT ACC TAC AGC TGG 1928

G   A   N   D   T   D   V   F   V   L   N   N   T   R   543
     GGT GCA AAT GAT ACG GAT GTC TTC GTC CTT AAC AAC ACC AGG 1970

P   P   L   G   N   W   F   G   C   T   W   M   N   S   557
     CCA CCG CTG GGC AAT TGG TTC GGT TGT ACC TGG ATG AAC TCA 2012

T   G   F   T   K   V   C   G   A   P   P   C   V   I   571
     ACT GGA TTC ACC AAA GTG TGC GGA GCG CCC CCT TGT GTC ATC 2054

G   G   V   G   N   N   T   L   L   C   P   T   D   C   585
     GGA GGG GTG GGC AAC AAC ACC TTG CTC TGC CCC ACT GAT TGC 2096

F   R   K   H   P   E   A   T   Y   S   R   C   G   S   599
     TTC CGC AAA CAT CCG GAA GCC ACA TAC TCT CGG TGC GGC TCC 2138

G   P   W   I   T   P   R   C   M   V   D   Y   P   Y   613
     GGT CCC TGG ATT ACA CCC AGG TGC ATG GTC GAC TAC CCG TAT 2180

R   L   W   H   Y   P   C   T   I   N   Y   T   I   F   627
     AGG CTT TGG CAC TAT CCT TGT ACC ATC AAT TAC ACC ATA TTC 2222

K   V   R   M   Y   V   G   G   V   E   H   R   L   E   641
     AAA GTC AGG ATG TAC GTG GGA GGG GTC GAG CAC AGG CTG GAA 2264

A   A   C   N   W   T   R   G   E   R   C   D   L   E   655
     GCG GCC TGC AAC TGG ACG CGG GGC GAA CGC TGT GAT CTG GAA 2306

D   R   D   R   S   E   L   S   P   L   L   L   S   T   669
     GAC AGG GAC AGG TCC GAG CTC AGC CCG TTG CTG CTG TCC ACC 2348

T   Q   W   Q   V   L   P   C   S   F   T   T   L   P   683
     ACA CAG TGG CAG GTC CTT CCG TGT TCT TTC ACG ACC CTG CCA 2390

A   L   S   T   G   L   I   H   L   H   Q   N   I   V   697
     GCC TTG TCC ACC GGC CTC ATC CAC CTC CAC CAG AAC ATT GTG 2432
```

```
  D   V   Q   Y   L   Y   G   V   G   S   S   I   A   S   711
 GAC GTG CAG TAC TTG TAC GGG GTA GGG TCA AGC ATC GCG TCC 2474

W   A   I   K   W   E   Y   V   V   L   L   F   L   L   725
 TGG GCC ATT AAG TGG GAG TAC GTC GTT CTC CTG TTC CTT CTG 2516

L   A   D   A   R   V   C   S   C   L   W   M   M   L   739
 CTT GCA GAC GCG CGC GTC TGC TCC TGC TTG TGG ATG ATG TTA 2558
                              ┌──►P7
  L   I   S   Q   A   E   A   A   L   E   N   L   V   I   753
 CTC ATA TCC CAA GCG GAG GCG GCT TTG GAG AAC CTC GTA ATA 2600
```

IgG     F(ab')₂     Fab'     Fab     Fv     "r IgG"     Fc

- WT (IQLINTNGSWHINS)
- W420R (IQLINTNGSRHINS)

ANTI-HEPATITIS C ANTIBODIES AND ANTIGEN BINDING FRAGMENTS THEREOF

CROSS-REFERENCE TO RELATED APPLICATIONS

This application is a national stage under 35 U.S.C. 371 of International Application PCT/GB2015/052558, filed on Sep. 4, 2015 (currently published). International Application no. PCT/GB2015/052558 cites the priority of Great Britain patent application no. 1415714.3, filed Sep. 5, 2014, currently expired.

FIELD OF THE INVENTION

The invention relates to antibodies or fragments thereof capable of generating an immune response against the Hepatitis C Virus (HCV) E2 protein.

BACKGROUND TO THE INVENTION

There is an urgent need for a vaccine that will protect from infection with hepatitis C virus (HCV), which is a leading cause of liver cirrhosis and liver cancer. At present no such vaccine exists, and HCV infection is a major global public health problem. One of the obstacles to vaccine development is the high genetic diversity of the viral envelope glycoproteins.

HCV vaccine development has been thwarted by the high genetic diversity of the envelope glycoproteins and the presence of immunodominant, hypervariable regions within them. To elicit protective antibodies, the immune response needs to be focused on conserved, functionally important regions. The epitopes of broadly neutralizing antibodies (bnAbs) are therefore attractive leads for vaccine design.

One such bnAb is known antibody AP33, which binds to a conserved linear epitope (residues 412-423) on the HCV E2 envelope glycoprotein and potently neutralizes all genotypes of HCV.

The AP33 epitope, which spans residues 412 to 423 of HCV E2, is linear and highly conserved and encompasses a tryptophan residue that plays a critical role in CD81 recognition. The antibody has been shown to be capable of neutralising HCV across all the major genotypes. The rational development of immunogens that might mimic such epitopes and elicit AP33-like antibodies has been stymied by a range of factors in the art including the lack of detailed structural information available for the viral glycoproteins. Moreover, vaccination with peptides representing the epitope did not elicit antibodies that recognise E2.

It is a problem in the art to elicit antibodies that recognise E2.

The present invention seeks to overcome problem(s) associated with the prior art.

SUMMARY OF THE INVENTION

The generation of broadly neutralising antibodies for Hepatitis C virus (HCV) has been a problem in the art. Conventional approaches such as immunisation with peptides representing the key epitope of HCV E2 (residues 412 to 423 of E2) has failed to elicit antibodies that recognise E2.

The inventors rejected conventional approaches based on E2 peptide immunisations. The inventors instead pursued an anti-idiotypic approach. More specifically, the inventors have generated anti-idiotype antibodies against the established AP33 broadly neutralising antibody. Even this approach initially failed, until the inventors applied insights from a structural analysis of the epitope binding pocket of the AP33 antibody in order to design a radical selection technique allowing them to obtain the B2.1A anti-idiotypic antibody having remarkable properties.

The present invention is based upon the B2.1A antibody and its unique characteristics.

Thus, in one aspect the invention provides an antibody or antigen binding fragment thereof capable of binding to the antigen binding pocket of the AP33 antibody, wherein said antibody or antigen binding fragment thereof comprises VL CDR1 (L1), VL CDR2 (L2), and VL CDR3 (L3) consisting of the amino acid sequences of SEQ ID NO:1, SEQ ID NO:2 and SEQ ID NO:23 respectively, and comprises VH CDR1 (H1), VH CDR2 (H2), and VH CDR3 (H3) consisting of the amino acid sequences of SEQ ID NO:24, SEQ ID NO:25, and SEQ ID NO:26 respectively.

Suitably said antibody or antigen binding fragment thereof comprises VL amino acid sequence consisting of the amino acid sequence of SEQ ID NO:20.

Suitably said antibody or antigen binding fragment thereof comprises VH amino acid sequence consisting of the amino acid sequence of SEQ ID NO:22.

Suitably said antibody or antigen binding fragment thereof comprises VL amino acid sequence consisting of the amino acid sequence of SEQ ID NO:20 and said antibody or antigen binding fragment thereof comprises VH amino acid sequence consisting of the amino acid sequence of SEQ ID NO:22.

In another aspect, the invention relates to an antibody or antigen binding fragment thereof as described above, wherein the antigen binding fragment thereof is selected from the group consisting of a Fab fragment, a Fab' fragment, a F(ab')2 fragment, a scFv, a Fv, a rIgG, and a diabody.

Suitably said antigen binding fragment is a scFv and wherein said scFv comprises the amino acid sequence of SEQ ID NO:11 or SEQ ID NO:12 or SEQ ID NO:13.

In another aspect, the invention relates to a nucleic acid comprising a nucleotide sequence encoding the variable heavy chain domain and/or the variable light chain domain of the antibody or antigen binding fragment as described above.

Suitably the nucleic acid comprises one or more nucleotide sequences selected from the group consisting of SEQ ID NO:19 and SEQ ID NO:21.

In another aspect, the invention relates to a nucleic acid comprising a nucleotide sequence complementary to the nucleotide sequence as described above.

In another aspect, the invention relates to a vector comprising the nucleic acid as described above.

Suitably the vector further comprises an expression control sequence operatively linked to the nucleic acid encoding the variable heavy chain domain and/or the variable light chain domain.

In another aspect, the invention relates to a host cell containing the vector as described above.

Suitably the cell is a eukaryotic cell.

Suitably the eukaryotic cell is a Chinese Hamster Ovary (CHO) cell or a human embryonic kidney (HEK) cell.

In another aspect, the invention relates to a method of producing an antibody or antigen binding fragment thereof, comprising incubating a host cell as described above such that the encoded variable heavy chain domain and/or variable light chain domain is expressed by the cell; and recovering the expressed the antibody or antigen binding fragment thereof.

Suitably the method further comprises isolating and/or purifying the recovered antibody or antigen binding fragment thereof.

In another aspect, the invention relates to a composition comprising the antibody or antigen binding fragment thereof as described above and a pharmaceutically acceptable carrier or excipient.

In another aspect, the invention relates to a composition as described above further comprising a carrier protein, the carrier protein preferably selected from the group consisting of tetanus toxoid and CRM 197 mutant diphtheria toxin.

Suitably said composition further comprises an adjuvant.

In another aspect, the invention relates to a composition as described above formulated for use in humans.

In another aspect, the invention relates to an antibody or antigen binding fragment thereof capable of inducing in a mammal an immune response against the hepatitis C virus E2 protein, wherein said antibody or antigen binding fragment thereof is capable of binding to the antigen binding pocket of the monoclonal AP33 antibody.

In another aspect, the invention relates to an antibody or antigen binding fragment thereof capable of inducing in a mammal an immune response against the hepatitis C virus E2 protein, wherein said antibody or antigen binding fragment thereof comprises VL CDR1 (L1), VL CDR2 (L2), and VL CDR3 (L3) consisting of the amino acid sequences of SEQ ID NO:1, SEQ ID NO:2 and SEQ ID NO:23 respectively, and comprises VH CDR1 (H1), VH CDR2 (H2), and VH CDR3 (H3) consisting of the amino acid sequences of SEQ ID NO:24, SEQ ID NO:25, and SEQ ID NO:26 respectively.

In another aspect, the invention relates to an antibody or antigen binding fragment thereof capable of binding to the AP33 antibody wherein said antibody or antigen binding fragment thereof exhibits binding to AP33 antibody mutants $FL_{32}A$, NL91A, WL96A, YH33A, YH50A, YH58A, IH95A and YH100A of less than 50% of its binding to the AP33 antibody.

In another aspect, the invention relates to an antibody that binds to an antibody or antigen binding fragment thereof as described above, which is not AP33 antibody or a fragment thereof.

Suitably said antibody is obtained by immunisation of a mammal with an antibody or antigen binding fragment thereof as described above.

In another aspect, the invention relates to a method of inducing in a mammal an immune response against the hepatitis C virus E2 protein, the method comprising administering to said mammal an antibody as described above, a nucleic acid as described above, a vector as described above, or a composition as described above.

In another aspect, the invention relates to an antibody as described above, a nucleic acid as described above, a vector as described above, or a composition as described above for inducing in a mammal an immune response against the hepatitis C virus E2 protein.

In one aspect, the invention relates to an antibody, a nucleic acid, a vector, or a composition as described above for use in manufacture of a composition for immunising against HCV.

In one aspect, the invention relates to an antibody, a nucleic acid, a vector, or a composition as described above for inducing in a mammal an immune response against the hepatitis C virus E2 protein.

Suitably said immune response induced is a humoral or antibody immune response. Suitably said antibody induced binds HCV E2, suitably binding is at the 412-423 AP33 epitope. Suitably the antibodies induced bind HCV particles. Suitably the antibodies induced are neutralising antibodies.

DETAILED DESCRIPTION OF THE INVENTION

To obtain a molecule that correctly represents the 3-dimensional binding surface of the HCV E2 412-423 epitope, we pursued an anti-idiotype approach.

Mice were immunized with AP33 (Ab1) to generate a large number of anti-idiotypic (Ab2) monoclonal antibodies, all of which were able to potently inhibit AP33-E2 binding. The crystal structure of AP33 Fab complexed with its peptide epitope shows which amino acid residues comprise the antigen-binding pocket. By individually replacing these with alanine, we established exactly which residues are required for E2 binding. The AP33 mutants were then used to differentiate between the Ab2s. This screen identified one Ab2 with a binding profile very similar to that of E2. When used as an immunogen in mice, this Ab2 induced Ab3 antibodies that recognize the same epitope and the same residues within it as AP33. The affinity of the Ab3 antibodies for E2 is similar to that of AP33, and they neutralize infectivity of cell-culture infectious HCV with an $IC_{50}$ that is about twice that of AP33.

In one aspect the polypeptide of the invention comprises a B2.1A IgG molecule. A B2.1A IgG molecule is suitably an IgG molecule which comprises amino acid sequence of the CDRs of B2.1A e.g. the CDRs as shown in SEQ ID NO:s 1, 2, 23, 24, 25 and 26.

Suitably the polypeptide of the invention is a Fab fragment of the B2.1A IgG. The inventors have surprisingly discovered that the Fab fragment of the B2.1A antibody in fact performs better than the parent antibody itself. In addition, the Fab fragment is smaller and easier to handle. In addition, by removing sequences not required for antigen recognition the Fab fragment presents fewer irrelevant sequences to the immune system of the recipient, and therefore provides a more efficient antigen for immunisation.

Suitably the polypeptide of the invention may be a single chain variable fragment (scFv) derived from the B2.1A antibody sequence. This has the advantage of being of the smallest possible size whilst retaining the antigen binding activity. scFvs can also be cheap and efficient to produce by recombinant means.

The polypeptide or antibody or antigen binding fragment thereof of the invention may take any of the known forms. For example, the polypeptide may comprise an IgG. For example, the polypeptide may comprise a F(ab')2. For example, the polypeptide may comprise a Fab'. For example, the polypeptide may comprise a Fab. For example, the polypeptide may comprise a Fv. For example, the polypeptide may comprise a rIgG.

A person skilled in the art can make these or any other antibody variants according to their choice and/or the desired application. The production of each of these and any other antibody variants is enabled by the amino acid sequences of the variable regions of the B2.1A antibody provided herein, in particular the exact sequences of the CDRs. For example, in order to produce IgG, the variable region sequences such as the CDRs (i.e. nucleotide sequence encoding the CDRs or the larger variable regions) may be inserted into a standard heavy/light chain expression vector.

For example, B2.1A antibody chains may be produced using conventional antibody expression systems incorporating the CDRs of the B2.1A as disclosed herein. Suitably a conventional expression system such as the 'antibody generation' system which is commercially available from InvivoGen at 5, rue Jean Rodier, F-31400 Toulouse, France may be used.

This vector may then be transfected into any suitable host cell. Suitably the host cell is eukaryotic such as mammalian. For example, suitable host cells may include CHO cells, 293T cells, HEK cells or any other suitable cell line. Following transfection, the host cells are incubated to allow expression of the antibody chains. These are the collected, for example from the supernatant in which the cells are incubated.

Purification of the antibody chains from that supernatant may be carried out. Purification may be by any known means such as chromatography, for example affinity chromatography (e.g. Protein A, Protein G, Protein L, Peptide M etc) or any other suitable means known in the art.

Thus, when a full IgG is desired, then the expression vector is so chosen so as to express the chains for a full IgG. If it is desired to produce a Fab fragment from that IgG, then any standard method known in the art such as papain digestion, pepsin digestion or ficin digestion may be used to generate that Fab. Most suitably, papain digestion of IgG is used to generate Fab.

Generation of antibodies or antigen binding fragments thereof, for example via antibody fragmentation, is well known in the art using commercially available reagents such as from Pierce (Pierce Protein Biology Products also known as ThermoScientific (ThermoFisher Scientific) of 3747 N Meridian Rd, Rockford, Ill. 61101, USA.

Suitably the antibody or antigen binding fragment thereof of the invention may be administered in conjunction with, or formulated into a composition with, a carrier that is suitable for use in humans.

Suitably the antibody or antigen binding fragment thereof of the invention may be administered in conjunction with, or formulated into a composition with, an adjuvant that is suitable for use in humans Alum is a most commonly used adjuvant in human vaccination. It is found in numerous vaccines, including diphtheria-tetanus-pertussis, human papillomavirus and hepatitis vaccines. Alum provokes a strong Th2 response. Suitably the adjuvant comprises Alum. Suitably alum means aluminium hydroxide, such as in the form of a wet gel suspension.

The adjuvant suitably induces both Th1 and Th2 responses.

Further guidance on adjuvants is provided by the European Medicines Agency's (EMEA) committee for medicinal products for human use. In particular, reference is made to their guideline on adjuvants in vaccines for human use document, which is incorporated herein by reference.

Suitably the antibody or antigen binding fragment thereof of the invention may be administered as, or provided as, a formulation that is suitable for use in humans.

Known carrier proteins include Keyhole Limpet Haemocyanin (KLH), self assembling carrier proteins such as Ferritin or luminaze synthase. There are numerous carrier proteins that are commonly used in compositions such as human vaccines: suitably the carrier protein is tetanus toxoid or CRM 197 mutant diphtheria toxin. As will be apparent to the skilled person, these are vaccines in their own right, against tetanus and diphtheria, respectively. They are also effective as immunogenic carrier proteins for molecules such as bacterial polysaccharides, which on their own are poorly immunogenic.

In principle, any protein molecule that is used in approved human vaccines could be a suitable carrier. The choice of carrier may be made by the skilled worker and confirmed either experimentally and/or through clinical trials.

The same principles apply to a suitable adjuvant. There is a limited number of adjuvants approved for human use, although there are a lot of candidate adjuvants and ongoing research into better human adjuvants, especially within the pharmaceutical industry. In principle, any adjuvant approved for use in human vaccines could be suitable. The choice of adjuvant may be made by the skilled worker and confirmed either experimentally and/or through clinical trials.

The same principles apply to a suitable vaccination regimen. Suitably a first administration of the of the antibody or fragment thereof (or nucleic acid or vector or composition) is provided. This may be referred to as a primary (or 'prime') injection. This is day 0. The immune response, for example as measured by antibody titer, can be maintained or enhanced ('boosted') in a mammal by providing one or more further or booster injections of the of the antibody or fragment thereof (or nucleic acid or vector or composition) at 2 weeks, 1 month, 2 months, 3 months, 4 months, 5 months, 6 months, 1 year, or more after the primary injection. The primary and further or booster injections need not be the same. Formulations may be different between injections such as carrier proteins may change, or nucleic acid may be alternated with peptide components as the operator chooses.

The same principles apply to a suitable formulation. In principle, any formulation suitable for use in human vaccines could be used. The choice of formulation may be made by the skilled worker and confirmed either experimentally and/or through clinical trials.

The composition may be a pharmaceutical composition.

The composition is suitably a composition suitable for generating an immune response to the antibody such as B2.1A antibody or fragment thereof as described herein. Suitably said immune response induced is a humoral or antibody immune response. Suitably said antibody induced binds HCV E2, suitably binding is at the 412-423 AP33 epitope. Suitably the antibodies induced bind HCV particles. Suitably the antibodies induced are neutralising antibodies.

Suitably the composition is a vaccine composition, suitably a vaccine composition for use in humans. Suitably the antibodies induced are protective against HCV infection.

Pharmaceutical compositions useful in the present invention may comprise an amount of the antibody or fragment thereof effective to induce an immune response in a subject and a pharmaceutically acceptable carrier, dilutent or excipient (including combinations thereof).

Pharmaceutical compositions may be for human or animal usage in human and veterinary medicine and will typically comprise any one or more of a pharmaceutically acceptable dilutent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The choice of pharmaceutical carrier, excipient or diluent may be selected with regard to the intended route of administration and standard pharmaceutical practice.

Pharmaceutical compositions may comprise as—or in addition to—the carrier, excipient or diluent any suitable binder(s), lubricant(s), suspending agent(s), coating agent(s) or solubilizing agent(s).

Preservatives, stabilizers, dyes and even flavoring agents may be provided in pharmaceutical compositions. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, pharmaceutical compositions useful in the present invention may be formulated to be administered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be administered by a number of routes. Most suitably the formulation is designed to be administered by injection via a route effective in inducing an immune response such as subcutaneously or intramuscularly.

The formulations to be used for in vivo administration must be sterile. This is readily accomplished by filtration through sterile filtration membranes.

The antibody or fragment thereof may even be prepared in situ in the subject being treated. In this respect, nucleotide sequences encoding said antibody or fragment thereof may be delivered by use of non-viral techniques (e.g., by use of liposomes) and/or viral techniques (e.g., by use of retroviral vectors) such that the said protein is expressed from said nucleotide sequence.

The pharmaceutical compositions may be used in any of the methods described herein.

The pharmaceutical composition may be used among those subjects (e.g., humans) susceptible to infection with HCV i.e. to prevent or reduce/decrease the onset of HCV infection, such as by inducing an immune reaction against HCV.

The pharmaceutical composition may be used among those subjects (e.g., humans) already infected with HCV i.e. to treat HCV infection. Such treatment may facilitate clearance of the virus from those subjects who are acutely or chronically infected including infected patients undergoing liver transplantation.

Thus, in a further aspect the invention provides a method for the treatment and/or prevention of hepatitis C virus infection, comprising the use of the antibody or the antibody fragment or the pharmaceutical composition. Suitably, an effective amount of the antibody or fragment thereof or the pharmaceutical composition is administered to the subject to induce an immune response.

There is also provided an antibody of a fragment thereof or the pharmaceutical composition for use in the treatment and/or prevention of hepatitis C virus infection in a subject.

Preferably the administered antibody/fragments thereof are substantially purified (e.g., preferably at least 95% homogeneity, more preferably at least 97% homogeneity, and most preferably at least 98% homogeneity, as judged by SDS-PAGE).

The active immunisation methods of the invention should allow for the protection or treatment of individuals against infection with viruses of a range of HCV genotypes, more suitably any of genotypes 1-6 of HCV, except for very occasional mutant isolates which contain several amino acid differences to that of the consensus peptide epitope 412-423 of E2.

Construction and operation of standard antibody expression systems as outlined above is well within the ambit of the skilled reader. Such systems are widely commercially available and are used as a matter of routine in order to produce antibody molecules having the desired CDRs.

In one aspect the polypeptide of the invention is a polypeptide comprising at least the six CDRs of the B2.1A antibody.

Unless otherwise indicated, all discussion of nucleotide and/or amino acid numbering herein follows the usual conventions. Numbering for polypeptide or polynucleotide sequences follows the numbering of the wild type version or the version apparent from the context. Numbering for antibody polypeptides/residues/mutants etc follows the established Kabat numbering (Kabat E A, Wu T T, Perry H M, Gottesman K S, Foeller C. 1991. Sequences of proteins of immunological interest, 5th ed. U.S. Department of Health and Human Services/NIH, Bethesda, Md.).

The polypeptide of the invention may be fused to another polypeptide such as a carrier polypeptide, a scaffold polypeptide or any other polypeptide.

It is further surprising that the Fab fragment of B2.1A performed better than the scFv of B2.1A. It is further surprising that the Fab fragment of B2.1A performed so well, especially since Fab fragments lose their divalence, but that did not appear to adversely affect performance.

The inventors took an unusual approach in selection of B2.1A. Firstly, they tried the conventional approach of immunising with target antibody (AP33) and generating anti-AP33 anti-idiotypic sera. However, those sera repeatedly failed. In order to address this problem, the inventors studied the crystal structure of AP33 complexed with its target, the linear E2 peptide. Based on this crystal structure, the inventors generated alanine mutants at fifteen different carefully selected sites on the AP33 antibody. In this manner, the inventors generated a panel of fifteen mutated antibodies based closely on AP33, each bearing a separate single alanine mutation in the key antigen binding pocket. The inventors tested the binding of these AP33 mutants to the E2 polypeptide. The inventors found that a single mutation at each of these carefully chosen sites was enough to abrogate the binding of the AP33 mutants to the AP33 epitope on the E2 polypeptide. In a remarkable new approach, the inventors then took this panel of mutant antibodies and analysed their binding to a panel of candidate anti-idiotype antibodies generated by immunisation with AP33. The results from this analysis varied widely. All of the anti-idiotype antibodies studied inhibited E2 binding to AP33. However, the anti-idiotype antibodies varied widely in their binding to the panel of fifteen mutant AP33 antibodies. Through a careful analysis of the binding of the anti-idiotype candidate antibodies to the fifteen alanine mutant AP33 antibodies, the inventors were able to select the remarkable B2.1A anti-idiotype antibody. This was the only anti-idiotype antibody in the analysis which showed a binding which was negatively affected by each of the individual alanine mutated AP33 mutant antibodies. This striking result is illustrated in Table 1. The key mutated residues in the AP33 light and heavy chains are highlighted in the "E2" row of the table. These correspond to eight alanine substitutions that reduce binding to E2 by more than 90%. These residues were therefore considered crucial to the AP33-E2 interaction. As can be seen in the row entitled "B2.1A", this anti-idiotypic antibody also showed a drastically reduced binding to each of the AP33 alanine mutants bearing substitutions at those crucial residues. In sharp contrast, all of the other candidate anti-idiotype antibodies shown in Table 1 maintained a high level of binding to at least one of those AP33-derived antibodies bearing alanine substitutions at crucial residues. For example, L1.1A shows 85% binding even to a N91A AP33 mutant antibody. Therefore, B2.1A was unique amongst all of the candidate anti-idiotypic antibodies analysed in that it showed a pattern of depressed binding to all of the AP33 mutant antibodies bearing alanine substitutions at the crucial residues for the AP33-E2 interaction. This was interpreted by the inventors as the strongest possible evidence that they had created an anti-idiotypic antibody whose 3-dimensional structure most closely mimicked the 3-dimensional structure of the crucial epitope on the E2 polypeptide itself.

For all of these reasons, it is clear that the B2.1A antibody has unique and valuable characteristics which could not be expected, and which are not shown by any other known antibody, nor any other candidate antibody studied by the inventors.

A more conventional approach might have been to use all of the candidate anti-idiotype antibodies to immunise. Resulting sera (anti-Ab2 or anti-(anti-idiotype) sera) which show antibodies recognising E2 would then be selected. However, when the inventors followed this approach they experienced problematic rates of failure. In fact, the inventors did this for 25 candidate anti-Ab2 sera. Although the anti-Ab2 sera showed inhibition of binding of AP33 to E2 (indicating that they contained anti-Ab2 antibodies), the anti-Ab2 sera did not bind E2, nor did they inhibit HCV in cell culture. The inventors therefore rethought their approach as described above.

For illustrative/comparative purposes, a selection of the failed sera results are presented in a comparative example (see below).

It should be noted that the B2.1A antibody was very challenging to produce. For example, as described above, the inventors initially tried to obtain this antibody using twenty five separate immune sera generated by immunisation with AP33 antibodies.

As explained above, none of those yielded the successful anti-idiotypic antibody having the features of B2.1A. In addition, prior attempts to induce anti-HCV E2 412 to 423 antibodies by immunising with E2 peptides, such as peptides comprising the 412 to 423 E2 antigen were unsuccessful. In view of these robust attempts to generate a successful immunogenic anti-idiotype antibody, the expectation would have been that such an antibody could not be produced. However, even in the face of this stark scientific situation, the inventors were able to adapt and make progress over a long period of arduous research as described herein. The result was the B2.1A antibody which is both structurally novel in terms of its sequence, in particular the unique and novel sequences of the CDRs and/or of the VL and/or of the VH chains, and also provides striking and unique characteristics which are beneficial and render it susceptible of industrial application/utility. These properties are discussed in more detail below.

More specifically, the fact that the inventors were able to produce an antibody capable of replicating the key binding characteristics between the broadly neutralising AP33 antibody and its target epitope of residues 412 to 423 of E2 is an unexpected and extremely valuable achievement.

With reference to Table 1 showing the binding properties of E2 and anti-idiotypic antibodies to wild-type and mutant AP33, by "high" binding is meant binding of the test polypeptide to AP33 mutants at scores of 50% or higher of the binding of E2 to wild-type AP33. In particular, the key mutants under consideration are $F_L32A$, $N_L91A$, $W_L96A$; $Y_H33A$, $Y_H50A$, $Y_H58A$, $I_H95A$ and $Y_H100A$.

Antibodies

Antibodies are naturally occurring immunoglobulin molecules which have varying structures, all based upon the immunoglobulin fold. For example, IgG antibodies such as AP33 have two 'heavy' chains and two 'light' chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody or fragment thereof to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC). In some embodiments, the hypervariable regions are the amino acid residues of an antibody which are responsible for antigen-binding. The hypervariable region may comprise amino acid residues from a "complementarity determining region" or "CDR" (e.g., around about residues 24-34 (L1), 50-56 (L2) and 89-97 (L3) in the VL, and around about 31-35B (H1), 50-65 (H2) and 95-102 (H3) in the VH (Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2)

and 91-96 (L3) in the VL, and 26-32 (H1), 52A-55 (H2) and 96-101 (H3) in the VH (Chothia and Lesk J. Mol. Biol. 196:901-917 (1987)).

Each V region typically comprises three complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies, such as AP33, have antigen binding sites which are defined by VH and VL domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between VH and VL. Throughout the present specification and claims, unless otherwise indicated, the numbering of the residues in the constant domains of an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody. The residues in the V region are numbered according to Kabat numbering unless sequential or other numbering system is specifically indicated.

The antibody or antibody fragment described herein may be isolated or purified to any degree. As used herein, "isolated" means that that antibody or antibody fragment has been removed from its natural environment. In some embodiments, contaminant components of its natural environment are materials which would interfere with diagnostic or therapeutic or immunisation uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Purified" means that the antibody or antibody fragment has been increased in purity, such that it exists in a form that is more pure than it exists in its natural environment and/or when initially synthesized and/or amplified under laboratory conditions. Purity is a relative term and does not necessarily mean absolute purity.

AP33 Antibody

AP33 is a mouse monoclonal antibody (MAb) that can strongly inhibit the interaction between E2 (in various forms, including soluble E2, E1E2, and virus-like particles) and CD81 (Clayton R F, et al. 2002. Analysis of antigenicity and topology of E2 glycoprotein present on recombinant hepatitis C virus-like particles. J. Virol. 76:7672-7682, Owsianka A, Clayton R F, Loomis-Price L D, McKeating J A, Patel A H. 2001. Functional analysis of hepatitis C virus E2 glycoproteins and viruslike particles reveals structural dissimilarities between different forms of E2. J. Gen. Virol. 82:1877-1883, Owsianka A, et al. 2005. Monoclonal antibody AP33 defines a broadlyneutralizing epitope on the hepatitis C virus E2 envelope glycoprotein. J. Gen. Virol. 79:11095-11104).

The AP33 epitope, which spans residues 412 to 423 of HCV E2, is linear and highly conserved and encompasses a tryptophan residue that plays a critical role in CD81 recognition. Indeed, the antibody has been shown to be capable of potently neutralizing infection across all the major genotypes.

Any known AP33 antibody may be used in the methods and techniques described herein. AP33 has been humanised, for example as in WO2009/081285. Suitably references herein to 'AP33 antibody' refer to the wild type mouse monoclonal AP33 antibody. Most suitably 'AP33 antibody' means an antibody or antigen binding fragment thereof comprising the AP33 CDRs, more suitably comprising the AP33 VL and/or VH sequences as described below.

```
AP33 (WT) vh and vL coding sequences
AP33 WTV_H seq
The sequence is arranged Leader-vH.
The Leader sequence is boxed.

(SEQ ID NO: 14)
ATG GTG TTA AGT CTT CTG TAC CTG TTG ACA GCC CTT CCG GGT ATC CTG TCA GAG GTG

CAG CTT CAG GAG TCA GGA CCT AGC CTC GTG AAA CCT TCT CAG ACT CTG TCC CTC ACC

TGT TCT GTC ACT GGC GAC TCC ATC ACC AGT GGT TAC TGG AAC TGG ATC CGG AAA TTC

CCA GGG AAT AAA CTT GAG TAC ATG GGA TAC ATA AGT TAC AGT GGT AGC ACT TAC TAC

AAT CTA TCT CTC AGA AGT CGC ATC TCC ATC ACT CGA GAC ACA TCC AAG AAT CAG TAC

TAC CTG CAG TTG AAT TCT GTG ACT ACT GAG GAC ACA GCC ACA TAT TAC TGT GCG CTC
```

-continued

```
ATT ACT ACG ACT ACC TAT GCT ATG GAC TAC TGG GGT CAA GGA ACC TCA GTC ACC GTC

TCC
```
The amino acid sequence is disclosed by virtue of the above coding sequence
which may be translated into the amino acid sequence using the universal
genetic code.
AP33 WTV$_L$ seq
The sequence is arranged Leader-vL
The Leader sequence is boxed.

SEQ ID NO: (15)
```
ATG GAG ACA GAC ACA CTC CTG CTA TGG GTG CTG CTG CTC TGG GTT CCA GGT

TCC ACA GGT AAC ATT GTG CTG ACC CAA TCT CCA GTT TCT TTG GCT GTG TCT

CTG GGG CAG AGG GCC ACC ATT TCC TGC AGA GCC AGT GAA AGT GTT GAT GGT

TAT GGC AAT AGT TTT CTG CAC TGG TTC CAG CAG AAA CCA GGA CAG CCA CCC

AAA CTC CTC ATC TAT CTT GCA TCC AAC CTA AAC TCT GGG GTC CCT GCC AGG

TTC AGT GGC AGT GGG TCT AGG ACA GAC TTC ACC CTC ACC ATT GAT CCT GTG

GAG GCT GAT GAT GCT GCA ACC TAT TAC TGT CAG CAA AAT AAT GTG GAC CCG

TGG ACG TTC GGT GGA GGC ACC AAG CTG GAA ATC AAA
```
The amino acid sequence is disclosed by virtue of the above coding sequence
which may be translated into the amino acid sequence using the universal
genetic code.

The sequences of the CDRs of AP33 are suitably as disclosed by the above nucleotide coding sequence of the VL and VH regions of AP33 antibody since it is a routine matter for the skilled worker to identify the CDRs given the VL/VH sequences.

The 'antigen binding pocket of the monoclonal AP33 antibody' is defined as known in the art, for example in Potter et al 2012 (J. Virol. vol 86 No 23 pages 12923-12932 "Toward a Hepatitis C Virus Vaccine: the Structural Basis of HepatitisC Virus Neutralization by AP33, a Broadly Neutralizing Antibody") which is incorporated 50 herein by reference for the specific disclosure of the antigen binding pocket, with particular reference to FIG. 3 of Potter et al 2012.

In case any further guidance is required, reference is made to the examples section herein.

Suitably the 'antigen binding pocket of the monoclonal AP33 antibody' is that part of AP33 which comprises the AP33 residues shown in Table 1.

Most suitably the 'antigen binding pocket of the monoclonal AP33 antibody' is that part of AP33 which comprises the AP33 residues highlighted in Table 1 (double underlined and bold in the head of the table in the 'WT AP33' row).

HCV E2 Protein

The HCV E2 protein is known in the art. For ease of reference representative HCV E2 sequences (both amino acid and nucleotide sequences) are provided in FIG. 5.

The sequences presented are translation of: HCV strain H77c The sequence shown is from HCV nucleotides 1 to 2600 encoding viral proteins core, E1 and E2 as annotated. The E2 sequence from amino acid residue 384-746 is underlined.

B2.1A Antibody

The sequence of B2.1A light and heavy chain variable regions is shown below.

Following convention, the vL CDRs are described as CDR1, CDR2 and CDR3. Alternatively, the light chain CDRs may be referred to as L1, L2, L3 and heavy chain CDRs as H1, H2, H3.

The CDRs are shown in boxed type on the amino acid sequence (the three sections of boxed type are CDR1, 2 and 3, respectively). These are also shown separately for ease of reference. Where there is underlining in a particular sequence, any non-underlined sequences are nucleotides/residues at the beginning of the sequence that did not appear in our sequencing, i.e. they were missing from the sequence because they were too close to the primer. They are therefore taken from the germline sequence that matches the rest of the obtained sequence.

In the preferred sequences:
CDRs defined by Kabat analysis are in bold
CDRs Defined by Chothia Analysis are Underlined

|  | Example Sequence | Preferred Sequence |
|---|---|---|
| B2.1A Light chain | | |
| B2.1A Light chain nucleotide sequence | TGTGATGACCCAGTCTCCAA<br>AATTCATGTCCACATCAGTAG<br>GAGACAGGGTCAGCATCACC<br>TGCAAGGCCAGTCAGAATGT<br>TCGTACTGCTGTAGCCTGGT<br>ATCAACAGAAACCAGGGCAG<br>TCTCCTAAAGCACTGATTTAC<br>TTGGCATCCAGCCGGCACAC<br>TGGAGTCCCTGATCGCTTCA<br>CAGGCAGTGGATCTGGGACA | GATATAGTGATGACCCAGTCT<br>CCAAAATTCATGTCCACATCAG<br>TAGGAGACAGGGTCAGCATCA<br>CCTGCAAGGCCAGTCAGAATG<br>TTCGTACTGCTGTAGCCTGGT<br>ATCAACAGAAACCAGGGCAGT<br>CTCCTAAAGCACTGATTTACTT<br>GGCATCCAGCCGGCACACTGG<br>AGTCCCTGATCGCTTCACAGG<br>CAGTGGATCTGGGACAGATTT |

|  | Example Sequence | Preferred Sequence |
|---|---|---|
|  | GATTTCACTCTCACCATTAGC AATGTGCAATCTGAAGACCT GGCAGATTATTTCTGTCTGCA ACATTGGAATTATCCGTACAC GTTCGGAGGGGGGACCAAGC TGGAAATAAAACGGGCTGAT GCTGCACCAACTG (SEQ ID NO: 9) | CACTCTCACCATTAGCAATGTG CAATCTGAAGACCTGGCAGAT TATTTCTGTCTGCAACATTGGA ATTATCCGTACACGTTCGGAG GGGGACCAAGCTGGAAATAA AACGG (SEQ ID NO: 19) |
| B2.1A Light chain amino acid sequence | DIVMTQSPKFMSTSVGDRVSI TCKASQNVRTAVAWYQQKP GQSPKALIYLASSRHTGVPDR FTGSGSGTDFTLTISNVQSED LADYFCLQHWNYPYTFGGGT KLEIKRA (SEQ ID NO: 7) | DIVMTQSPKFMSTSVGDRVSIT CKASQNVRTAVAWYQQKPG QSPKALIYLASSRHTGVPDRF TGSGSGTDFTLTISNVQSEDLA DYFCLQHWNYPYTFGGGTK LEIKR (SEQ ID NO: 20) |
| VL CDR1 (L1) | KASQNVRTAVA (SEQ ID NO: 1) | KASQNVRTAVA (SEQ ID NO: 1) |
| VL CDR2 (L2) | LASSRHT (SEQ ID NO: 2) | LASSRHT (SEQ ID NO: 2) |
| VL CDR3 (L3) | LQHWNYPY (SEQ ID NO: 3) | LQHWNYPYT (SEQ ID NO: 23) |

| B2.1A Heavy chain | | |
|---|---|---|
| B2.1A Heavy chain nucleotide sequence | CTTCCGGAATTNCAGGTNCA GCTGCAGGAGTCTGGGGCTG AGCTGGTGAAGCCTGGGGCT TCAGTGAAGCTGTCCTGCAA GGCTTCTGGCTACACCTTCAC CAACTACTGGATGCACTGGG TTAAGGCAGAGGCCTGGACAA GGCCTTGAGTGGATTGGAGA GATTAATCCTAGCGACGGTC ATACTAACTACAATGAGAAG TTCAAGAGCAAGGCCACACT GACTGTAGACAAATCCTCCA GCACAGCCTACATGCAACTC AGCAGCCTGACATCTGAGGA CTCTGCGGTCTATTACTGTGC AAGACCTTGGGCGTTTGGTA ACTACGGGGCCTGGTTTGCT TACTGGGGCCAAGGGACTCT GGTCACTGTCTCTGCAGCCA AAACGACACCCCCATCT (SEQ ID NO: 10) | CAGGTTCAGCTGCAGGAGTC TGGGACTGAGCTGGTGAAGC CTGGGGCTTCAGTGAAGCTG TCCTGCAAGGCTTCTGGCTA CACCTTCACCAACTACTGGAT GCACTGGGTTAAGCAGAGGC CTGGACAAGGCCTTGAGTGG ATTGGAGAGATTAATCCTAG CGACGGTCATACTAACTACA ATGAGAAGTTCAAGAGCAAG GCCACACTGACTGTAGACAA ATCCTCCAGCACAGCCTACAT GCAACTCAGCAGCCTGACAT CTGAGGACTCTGCGGTCTAT TACTGTGCAAGACCTTGGGC GTTTGGTAACTACGGGGCCT GGTTTGCTTACTGGGGCCAA GGGACTCTGGTCACTGTCTC TGCA (SEQ ID NO: 21) |

-continued

| | Example Sequence | Preferred Sequence |
|---|---|---|
| B2.1A Heavy chain amine acid sequence | QVQLQESGAELVKPGASVKLS CKASGYTFT[NYWMH]WVKQR PGQGLEWIG[EINPSDGHTNY] [NEKFKS]KATLTVDKSSSTAY MQLSSLTSEDSAVYYCAR[PW] [AFGNYGAWFA]YWGQGTLVT VSA (SEQ ID NO: 8) | QVQLQESGTELVKPGASVKLS CKAS[GYTFTNYW]MHWVKQ RPGQGLEWIGE[INPSDGHT] NYNEKFKSKATLTVDKSSST AYMQLSSLTSEDSAVYYCAR[P] [WAFGNYGAWFA]YWGQGT LVTVSA (SEQ ID NO: 22) |
| VH CDR1 (H1) | [NYWMH] (SEQ ID NO: 4) | [GYTFTNYW] (SEQ ID NO: 24) |
| VH CDR2 (H2) | [EINPSDGHTNYNEKFKS] (SEQ ID NO: 5) | [NPSDGH] (SEQ ID NO: 25) |
| VH CDR3 (H3) | [PWAFGNYGAWFA] (SEQ ID NO: 6) | [PWAFGNYGAWFAY] (SEQ ID NO: 26) |

Preferred CDRs based on crystal structure are [boxed.] In all instances, unless otherwise apparent from the context, reference to the CDRs of the B2.1A antibody (or derivative thereof) refers to the preferred CDRs as boxed above. In the heavy chain preferred sequences, the T in italics was originally sequenced as A but corrected to T. Corresponding codon is ACT.

Regarding the Preferred Sequences compared to the Example Sequences, there are some minor differences: (1) There are three extra codons at the beginning of the LC sequence, which code for DIV; (2) extra nucleotides at the 3' end of the LC sequence that do not code for the aa sequence of the LC variable region have been deleted; (3) Extra nucleotides at the 5' end of the HC sequence that do not code for the aa sequence of the HC variable region have been deleted; (4) The nucleotide given as N within the coding sequence of the HC is actually a T, i.e. the first two codons are CAG GTT (coding for aa's QV); (5) The ninth aa of the HC is T, not A. The corresponding codon is ACT, not GCT.

Regarding the preferred CDR sequences, as the skilled worker will appreciate, there are various models for assigning/identifying the CDR sequences in antibody VL/VH chains. The most popular/widely accepted versions are the Chothia and Kabat models, although others also exist such as the ABM and CONTACT models. The 'Example Sequence' CDR sequences were determined using the Kabat model as is conventional in the art. Therefore, whilst the Kabat determined CDRs represent a robust determination, they are in fact only modelled/predicted CDRs. The absolute/correct CDR sequences are those which are experimentally determined. The inventors have carried out this labour intensive analysis by creating a crystal structure. The experimentally determined CDRs are the 'Preferred Sequences'.

Expression of Recombinant Antibodies

Also provided are isolated nucleic acids encoding the antibodies and fragments thereof described herein such as the B2.1A antibodies, vectors and host cells comprising the nucleic acid, and recombinant techniques for the production of the antibody. The antibodies described herein may be produced by recombinant expression.

Nucleic acids encoding light and heavy chain variable regions as described herein optionally linked to constant regions, and inserted into an expression vector(s). The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences.

Suitably, the expression control sequences are eukaryotic promoter systems in vectors capable of transforming or transfecting eukaryotic host cells (e.g., COS cells—such as COS 7 cells—or CHO cells). Once the vector has been incorporated into the appropriate host, the host is maintained under conditions suitable for high level expression of the nucleotide sequences, and the collection and purification of the cross-reacting antibodies.

These expression vectors are typically replicable in the host organisms either as episomes or as an integral part of the host chromosomal DNA.

Selection Gene Component—Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362). In some embodiments, selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the nucleic acid encoding antibodies or fragments thereof described herein such as the B2.1A antibodies, such as DHFR, thymidine kinase, metallothionein-I and -III, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody described herein, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trpl gene present in the yeast plasmid YRp7 (Stinchcomb et al., *Nature*, 282:39 (1979)). The trpl gene provides a selection marker for a mutant strain of yeast lacking the ability to grow in tryptophan, for example, ATCC No. 44076 or PEP4-1. Jones, *Genetics*, 85:12 (1977). The presence of the trpl lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of Kluyverom yces have also been disclosed. Fleer et al., *Bio/Technology*, 9:968-975 (1991).

Signal Sequence Component—The antibodies described herein such as the B2.1A antibodies may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. A signal sequence can be substituted with a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibodies described herein such as the B2.1A antibodies.

Origin of Replication—Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Promoter Component—Expression and cloning vectors usually contain a promoter that is recognized by the host organism and is operably linked to the nucleic acid encoding an antibody described herein such as a B2.1A antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

The transcription of an antibody described herein such as the B2.1A antibody from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human .beta.-interferon cDNA in mouse cells under the control of a thymidine kinase promoter from herpes simplex virus. Alternatively, the Rous Sarcoma Virus long terminal repeat can be used as the promoter.

Enhancer Element Component—Transcription of a DNA encoding the antibody described herein such as the B2.1A antibody by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the HCV binding antibody-encoding sequence, but is preferably located at a site 5' from the promoter.

Transcription Termination Component—Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. One useful transcription termination component is the bovine growth hormone polyadenylation region. See WO94/11026 and the expression vector disclosed therein.

The vectors containing the polynucleotide sequences (e.g., the variable heavy and/or variable light chain encoding sequences and optional expression control sequences) can be transferred into a host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection (see generally, Sambrook et al., sup ra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity is most preferred, for pharmaceutical uses.

Constructs

The invention further provides a nucleic acid construct comprising a polynucleotide as described herein.

Typically the construct will be an expression vector allowing expression, in a suitable host, of the polypeptide(s) encoded by the polynucleotide. The construct may comprise, for example, one or more of the following: a promoter active in the host; one or more regulatory sequences, such as enhancers; an origin of replication; and a marker, preferably a selectable marker. The host may be a eukaryotic or prokaryotic host, although eukaryotic (and especially mammalian) hosts may be preferred. The selection of suitable promoters will obviously depend to some extent on the host cell used, but may include promoters from human viruses such as HSV, SV40, RSV and the like. Numerous promoters are known to those skilled in the art.

The construct may comprise a polynucleotide which encodes a polypeptide comprising three light chain hypervariable loops or three heavy chain hypervariable loops. Alternatively the polynucleotide may encode a polypeptide comprising three heavy chain hypervariable loops and three light chain hypervariable loops joined by a suitably flexible linker of appropriate length. Another possibility is that a single construct may comprise a polynucleotide encoding two separate polypeptides—one comprising the light chain loops and one comprising the heavy chain loops. The separate polypeptides may be independently expressed or may form part of a single common operon.

The construct may comprise one or more regulatory features, such as an enhancer, an origin of replication, and one or more markers (selectable or otherwise). The construct may take the form of a plasmid, a yeast artificial chromosome, a yeast mini-chromosome, or be integrated into all or part of the genome of a virus, especially an attenuated virus or similar which is non-pathogenic for humans.

The construct may be conveniently formulated for safe administration to a mammalian, preferably human, subject. Typically, they will be provided in a plurality of aliquots, each aliquot containing sufficient construct for effective immunization of at least one normal adult human subject.

The construct may be provided in liquid or solid form, preferably as a freeze-dried powder which, typically, is rehydrated with a sterile aqueous liquid prior to use.

The construct may be formulated with an adjuvant or other component which has the effect of increasing the immune response of the subject (e.g., as measured by specific antibody titer) in response to administration of the construct.

Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *Escherichia coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

Vectors may be transformed into a suitable host cell as described below to provide for expression of a polypeptide encompassed in the present invention. Thus, in a further aspect the invention provides a process for preparing polypeptides for use in the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter.

Vectors may contain one or more selectable marker genes which are well known in the art.

There are many known heavy and light chain expression vectors commercially available. The skilled operator may choose vectors expressing the same constant region subtype as the original antibody. The sequence of the heavy and light chain variable regions is then easily placed into the vector accordingly.

Suitably InvivoGen (of 5, rue Jean Rodier, F-31400 Toulouse, France) vectors may be used for heterologous expression of antibodies or antigen binding fragments of the invention. For example, B2.1A may be expressed using pFUSE2ss-CLIg-mk for the K light chain and pFUSEss-CHIg-mG1 for the IgG1 heavy chain variable region. Similarly, there is a wide range of known vectors commercially available for scFV expression. To make the B2.1A scFv's, suitably vector(s) such as pDisplay or derivatives thereof may be used.

Host Cells

The invention further provides a host cell—such as a host cell in vitro—comprising the polynucleotide or construct described herein. The host cell may be a bacterium, a yeast or other fungal cell, insect cell, a plant cell, or a mammalian cell, for example. The invention also provides a transgenic multicellular host organism which has been genetically manipulated so as to produce a polypeptide in accordance with the invention. The organism may be, for example, a transgenic mammalian organism (e.g., a transgenic goat or mouse line).

*E. coli* is one prokaryotic host that may be of use. Other microbial hosts include bacilli, such as *Bacillus subtilis*, and other enterobacteriaceae, such as *Salmonella, Serratia*, and various *Pseudomonas* species. In these prokaryotic hosts, one can make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may be used for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the antibodies or fragments thereof as described herein and in some instances are preferred (See Winnacker, From Genes to Clones, VCH Publishers, N.Y., N.Y. (1987). For some embodiments, eukaryotic cells (e.g., COS7 cells) may be preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas.

In some embodiments, the host cell is a vertebrate host cell. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR(CHO, Urlaub et al., *Proc. Natl. Acad. Sci. USA* 77:4216 (1980)) or CHO-DP-12 line; mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT o60562, ATCC CCL51); TRI cells (Mather et al., *Annals N. Y. Acad. Sci.* 383:44-68 (1982)); MRC 5 cells; FS4 cells; and a human hepatoma line (Hep G2).

Alternatively, antibody-coding sequences can be incorporated into transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Alternatively, the antibodies described herein can be produced in transgenic plants (e.g., tobacco, maize, soybean and alfalfa). Improved 'plantibody' vectors (Hendy et al. (1999) *J. Immunol. Methods* 231:137-146) and purification strategies coupled with an increase in transformable crop species render such methods a practical and efficient means of producing recombinant immunoglobulins not only for human and animal therapy, but for industrial applications as well (e.g., catalytic antibodies). Moreover, plant produced antibodies have been shown to be safe and effective and avoid the use of animal-derived materials. Further, the differences in glycosylation patterns of plant and mammalian cell-produced antibodies have little or no effect on antigen binding or specificity. In addition, no evidence of toxicity or HAMA has been observed in patients receiving topical oral application of a plant-derived secretory dimeric IgA antibody (see Larrick et al. (1998) *Res. Imm unol.* 149:603-608).

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells. Suitable host cells for the expression of glycosylated antibodies such as a glycosylated B2.1A antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bomrnbyxmori* have been identified. A variety of viral strains for transfection are publicly available, e.g., the L-1 variant of *Autographa californica* NPV and the Bm-5 strain of *Bomnbyxmori* NPV, and such viruses may be used as the virus herein according to the present invention, particularly for transfection of *Spodoptera frugiperda* cells.

Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a C.sub.H3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Antibody Fragments

F(ab')2 (110,000 daltons) fragments contain two antigen-binding regions joined at the hinge through disulfides. This fragment is void of most, but not all, of the Fc region.

Fab' (55,000 daltons) fragments can be formed by the reduction of F(ab')2 fragments.

The Fab' fragment contains a free sulfhydryl group that may be alkylated or utilised in conjugation with an enzyme, toxin or other protein of interest. Fab' is derived from F(ab')2; therefore, it may contain a small portion of Fc.

Fab (50,000 daltons) is a monovalent fragment that can be produced from IgG and/or IgM, consisting of the VH, CH1 and VL, CL regions, linked by an intramolecular disulfide bond.

Fv (25,000 daltons) is the smallest fragment produced from IgG and/or IgM that contains a complete antigen-binding site. Fv fragments have the same binding properties and similar three-dimensional binding characteristics as Fab. The VH and VL chains of the Fv fragments are held together by non-covalent interactions. These chains tend to dissociate upon dilution, so methods have been developed to cross-link the chains through glutaraldehyde, intermolecular disulfides or a peptide linker. scFv are single chain Fvs and can be conveniently made recombinantly.

"rIgG" Fragments or "rIgG" refers to reduced IgG (75,000 daltons) or half-IgG. It is the product of selectively reducing just the hinge-region disulfide bonds. Although several disulfide bonds occur in IgG, those in the hinge-region are most accessible and easiest to reduce, especially with mild reducing agents like 2-mercaptoethylamine (2-MEA). Half-IgG are frequently prepared for the purpose of targeting the exposing hinge-region sulfhydryl groups that can be targeted for conjugation, either antibody immobilization or enzyme labeling.

Techniques for producing these different fragments are well known in the art. Examples of production and reagents needed are provided below such as in the examples section in case any further guidance is needed.

Immunisation and Challenge Studies

The immunocompetent Cre-lox mouse model developed by Marcus Dorner is the most appropriate model for testing HCV vaccines (Dorner et al 2011; Dorner et al 2013). Commercially available transgenic mice, strain FVB.129S6 (B6)-Gt(ROSA)26Sor$^{tm1(Luc)Kael}$/J, contain a LoxP-flanked STOP cassette restricting firefly luciferase expression. Expression of cyclization recombination (CRE) recombinase catalyses recombination between the two loxP sites, which removes the STOP cassette and activates the luciferase reporter gene, leading to intracellular luciferase expression.

The mice are made permissive for HCV entry by infection with adenoviruses encoding essential cell surface receptors (human CD81, occludin, claudin 1 and SR-BI), and then infected with recombinant bicistronic HCVcc expressing cyclization recombination (CRE) recombinase. Upon entry into mouse hepatocytes, the recombinant viral genome is translated and the CRE protein is expressed. The CRE recombinase excises the STOP cassette and activates the luciferase reporter, leading to expression of luciferase. Subsequent injection ofluciferin results in bioluminescence that can be measured using a using a whole body bioluminescence imager. The HCV-CRE virus does not undergo a full infectious cycle because mouse cells do not support HCV replication and assembly. Therefore infection does not proceed beyond the entry step. Given that they have a normal immune system, the Rosa26-Fluc mice can be immunised with a potential vaccine, for example B2.1A Fab-KLH. The mice are given a primary vaccination followed by several booster vaccinations. A test bleed is taken after each booster, to monitor the induction of anti-E2 antibodies. If the vaccination induces anti-E2 antibodies, vaccinated and unvaccinated mice are made permissive for HCV infection by administering adenovirus vectors as described above, and then challenged with HCV-CRE. Entry of HCV into hepatocytes is detected as bioluminescence, as described herein. An inverse correlation between HCV entry and anti-E2 titre indicates that the vaccine protects against HCV challenge. Further details are provided in the Examples section.

Properties of B2.1A

B2.1A is an anti-idiotype antibody.

B2.1A binds AP33 monoclonal antibody.

B2.1A inhibits the binding of AP33 monoclonal antibody to the E2 412 to 423 epitope.

B2.1A does not bind (or has low binding i.e. binding less than 50% compared to binding to wild-type AP33) to mutant AP33 antibodies such as $F_L32A$, $N_L91A$, $W_L96A$; $Y_H33A$, $Y_H50A$, $Y_H58A$, $I_H95A$ and/or $Y_H100A$.

Advantages

It is an advantage of the invention the B2.1A antibodies and derivatives are provided in spite of various failures during the intensive research carried out.

It is an advantage of the invention that a complex structure based selection procedure was devised in order to obtain the antibodies of the invention.

It is an advantage of the invention that a structurally novel antibody/antibody derivatives is/are provided in the form of B2.1A and the CDRs of B2.1A.

It is an advantage of the invention that the antibody and antibody derivatives described herein have not been able to be obtained by conventional routes.

It is an advantage of the antibody and antibody derivatives described herein that they exhibit a pattern of binding to AP33 mutants which closely emulates the binding pattern of E2 to those AP33 mutants.

It is an advantage that the invention provides an anti-idiotypic antibody useful for inducing an immune response capable of recognising E2 polypeptide.

It is an advantage of the invention that it enables the induction of an immune response targeting HCV E2 polypeptide.

It is an advantage of the invention that it enables the induction of an immune response against HCV E2 polypeptide.

It is an advantage of the invention that the paratope presented by B2.1A and its derivatives is an excellent mimic of the 3-dimensional structure of a key broadly neutralising epitope of the HCV E2 polypeptide.

It is an advantage of the invention that the paratope presented by B2.1A and its derivatives induce antibodies that recognise the same epitope as AP33. It is a further advantage that the induced antibodies recognise the same residues within that epitope it as AP33 recognises.

It is an advantage of the invention that the affinity of the Ab3 antibodies (i.e. the antibodies induced by the B2.1A antibodies or derivatives of the invention) for E2 is similar to that of AP33. It is a further advantage that the induced antibodies neutralize infectivity of cell-culture infectious HCV. They neutralise infectivity with an IC50 that is about twice that of AP33.

It is an advantage of the invention that fewer animals were required in order to obtain the B2.1A antibody.

It is a feature of the approach that the structural data available for the AP33-E2 interaction were extensively used in the rational design of the selection scheme.

The invention is now further described by way of numbered paragraphs:

paragraph 1. An antibody or antigen binding fragment thereof capable of binding to the antigen binding pocket of the AP33 antibody, wherein said antibody or antigen binding fragment thereof comprises VL CDR1 (L1), VL CDR2 (L2), and VL CDR3 (L3) consisting of the amino acid sequences of SEQ ID NO:1, SEQ ID NO:2 and SEQ ID NO:3 respectively, and comprises VH CDR1 (H1), VH CDR2 (H2), and VH CDR3 (H3) consisting of the amino acid sequences of SEQ ID NO:4, SEQ ID NO:5, and SEQ ID NO:6 respectively.

paragraph 2. An antibody according to paragraph 1 wherein said antibody or antigen binding fragment thereof comprises VL amino acid sequence consisting of the amino acid sequence of SEQ ID NO:7.

paragraph 3. An antibody according to paragraph 1 wherein said antibody or antigen binding fragment thereof comprises VH amino acid sequence consisting of the amino acid sequence of SEQ ID NO:8.

paragraph 4. An antibody according to paragraph 1 wherein said antibody or antigen binding fragment thereof comprises VL amino acid sequence consisting of the amino acid sequence of SEQ ID NO:7 and wherein said antibody or antigen binding fragment thereof comprises VH amino acid sequence consisting of the amino acid sequence of SEQ ID NO:8.

paragraph 5. An antibody or antigen binding fragment thereof according to any preceding paragraph, wherein the antigen binding fragment thereof is selected from the group consisting of a Fab fragment, a Fab' fragment, a F(ab')2 fragment, a scFv, a Fv, a rIgG, and a diabody.

paragraph 6. An antibody or antigen binding fragment thereof according to paragraph 5 wherein said antigen binding fragment is a scFv and wherein said scFv comprises the amino acid sequence of SEQ ID NO:11 or SEQ ID NO:12 or SEQ ID NO:13.

paragraph 7. A nucleic acid comprising a nucleotide sequence encoding the variable heavy chain domain and/or the variable light chain domain of the antibody or antigen binding fragment according to any preceding paragraph.

paragraph 8. The nucleic acid of paragraph 7, wherein the nucleic acid comprises one or more nucleotide sequences selected from the group consisting of SEQ ID NO:9 and SEQ ID NO:10.

paragraph 9. A nucleic acid comprising a nucleotide sequence complementary to the nucleotide sequence of paragraph 7 or paragraph 8.

paragraph 10. A vector comprising the nucleic acid of paragraph 7 or paragraph 8.

paragraph 11. The vector of paragraph 10, wherein the vector further comprises an expression control sequence operatively linked to the nucleic acid encoding the variable heavy chain domain and/or the variable light chain domain.

paragraph 12. A host cell containing the vector of paragraph 10 or paragraph 11.

paragraph 13. The host cell of paragraph 12, wherein the cell is a eukaryotic cell.

paragraph 14. The host cell of paragraph 13, wherein the eukaryotic cell is a Chinese Hamster Ovary (CHO) cell or a human embryonic kidney (HEK) cell.

paragraph 15. A method of producing an antibody or antigen binding fragment thereof, comprising incubating a host cell according to any of paragraphs 12 to 14 such that the encoded variable heavy chain domain and/or variable light chain domain is expressed by the cell; and recovering the expressed the antibody or antigen binding fragment thereof.

paragraph 16. The method of paragraph 15, which further comprises isolating and/or purifying the recovered antibody or antigen binding fragment thereof.

paragraph 17. A composition comprising the antibody or antigen binding fragment thereof according to any of paragraphs 1 to 6 and a pharmaceutically acceptable carrier or excipient.

paragraph 18. A composition according to paragraph 17 further comprising a carrier protein, the carrier protein preferably selected from the group consisting of tetanus toxoid and CRM 197 mutant diphtheria toxin.

paragraph 19. A composition according to paragraph 17 or paragraph 18 further comprising an adjuvant.

paragraph 20. A composition according to any of paragraphs 17 to 19 formulated for use in humans.

paragraph 21. An antibody or antigen binding fragment thereof capable of inducing in a mammal an immune response against the hepatitis C virus E2 protein, wherein said antibody or antigen binding fragment thereof is capable of binding to the antigen binding pocket of the monoclonal AP33 antibody.

paragraph 22. An antibody or antigen binding fragment thereof capable of inducing in a mammal an immune response against the hepatitis C virus E2 protein, wherein said antibody or antigen binding fragment thereof comprises VL CDR1 (L1), VL CDR2 (L2), and VL CDR3 (L3) consisting of the amino acid sequences of SEQ ID NO:1, SEQ ID NO:2 and SEQ ID NO:3 respectively, and comprises VH CDR1 (H1), VH CDR2 (H2), and VH CDR3 (H3) consisting of the amino acid sequences of SEQ ID NO:4, SEQ ID NO:5, and SEQ ID NO:6 respectively.

paragraph 23. An antibody or antigen binding fragment thereof capable of binding to the AP33 antibody wherein said antibody or antigen binding fragment thereof exhibits binding to AP33 antibody mutants FL32A, NL91A, WL96A, YH33A, YH50A, YH58A, IH95A and YH100A of less than 50% of its binding to the AP33 antibody.

paragraph 24. An antibody that binds to an antibody or antigen binding fragment thereof according to any of paragraphs 1 to 6, which is not AP33 antibody or a fragment thereof.

paragraph 25. An antibody according to paragraph 24 which is obtained by immunisation of a mammal with an antibody or antigen binding fragment thereof according to any of paragraphs 1 to 6.

paragraph 26. A method of inducing in a mammal an immune response against the hepatitis C virus E2 protein, the method comprising administering to said mammal an antibody according to any of paragraphs 1 to 6 or 21 to 25, a nucleic acid according to any of paragraphs 7 to 9, a vector according to paragraph 10 or paragraph 11, or a composition according to any of paragraphs 17 to 20.

paragraph 27. An antibody according to any of paragraphs 1 to 6 or 21 to 25, a nucleic acid according to any of paragraphs 7 to 9, a vector according to paragraph 10 or paragraph 11, or a composition according to any of paragraphs 17 to 20 for inducing in a mammal an immune response against the hepatitis C virus E2 protein.

Further Aspects and Applications

In a broad aspect, the invention relates to an antibody or antigen binding fragment thereof capable of binding to the monoclonal AP33 antibody.

In a broad aspect, the invention relates to an antibody or antigen binding fragment thereof as described above which comprises at least one of the $V_L$ CDR1 (L1), $V_L$ CDR2 (L2), $V_L$ CDR3 (L3), $V_H$ CDR1 (H1), $V_H$ CDR2 (H2), and $V_H$ CDR3 (H3) consisting of the amino acid sequences of SEQ ID NO:1, SEQ ID NO:2, SEQ ID NO:23, SEQ ID NO:24, SEQ ID NO:25, and SEQ ID NO:26 respectively. Suitably said antibody or antigen binding fragment thereof comprises at least two of said sequences, suitably said antibody or antigen binding fragment thereof comprises at least three of said sequences, suitably said antibody or antigen binding fragment thereof comprises at least four of said sequences, suitably said antibody or antigen binding fragment thereof comprises at least five of said sequences, suitably said antibody or antigen binding fragment thereof comprises all six of said sequences. When said antibody or antigen binding fragment thereof comprises at least three of said sequences, suitably it comprises each of the three $V_L$ sequences or the each of the three $V_H$ sequences.

In one aspect, the invention relates to a method of identifying a polypeptide having, or comprising a region or domain having, essentially the same three dimensional structure as the AP33 epitope residues 412 to 423 HCV E2, the method comprising (i) assaying the binding of said polypeptide to the AP33 antibody, and (ii) assaying the binding of said polypeptide to AP33 antibody mutants $F_L32A$, $N_L91A$, $W_L96A$, $Y_H33A$, $Y_H50A$, $Y_H58A$, $I_H95A$ and $Y_H100A$, wherein if the polypeptide exhibits binding to AP33 antibody mutants $F_L32A$, $N_L91A$, $W_L96A$, $Y_H33A$, $Y_H50A$, $Y_H58A$, $I_H95A$ and $Y_H100A$ of less than 50% of its binding to the AP33 antibody, said polypeptide is identified as having essentially the same three dimensional structure as the AP33 epitope residues 412 to 423 HCV E2.

Suitably the polypeptide is an antibody or antigen binding fragment thereof.

Suitably the polypeptide is an antibody or antigen binding fragment thereof generated by immunisation of a mammal with AP33 antibody.

Suitably binding is assayed by ELISA.

Suitably binding to AP33 antibody mutants is less than 60% of binding to the AP33 antibody.

In one aspect, the invention relates to a method of producing an antibody or antigen binding fragment thereof having, or comprising a region or domain having, essentially the same three dimensional structure as the AP33 epitope residues 412 to 423 HCV E2, said method comprising identifying a polypeptide having, or comprising a region or domain having, essentially the same three dimensional structure as the AP33 epitope residues 412 to 423 HCV E2 as described above, and expressing said antibody or antigen binding fragment thereof in vitro, and optionally purifying same.

In one aspect, the invention relates to a kit comprising the antibody or antigen binding fragment thereof as described above and instructions for administering said antibody or antigen binding fragment thereof.

In one aspect, the invention relates to a method for treating or preventing a hepatitis C virus infection in a human, comprising administering an effective amount of the antibody or antigen binding fragment thereof as described above. Suitably the antigen binding fragment thereof is selected from the group consisting of a Fab fragment, a Fab' fragment, a F(ab')2 fragment, a scFv, a Fv, a rIgG and a diabody.

Suitably the hepatitis C virus infection is an acute hepatitis C virus infection.

Suitably the hepatitis C virus infection is a chronic hepatitis C virus infection.

Suitably treating the hepatitis C virus infection comprises reducing viral load.

Suitably treating or preventing the hepatitis C virus infection comprises inducing an immune response against the hepatitis C virus, suitably against the E2 protein of the hepatitis C virus, most suitably against the AP33 epitope 412 to 423 of the E2 protein of the hepatitis C virus.

In some embodiments, suitably the method for treating or preventing a hepatitis C virus infection comprises administering a second therapeutic agent.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which.

Figure 1:
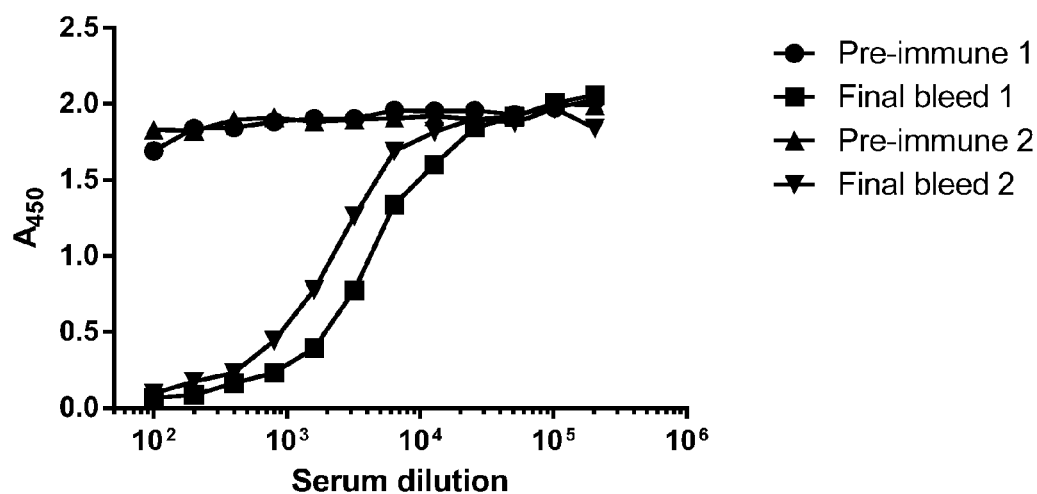
FIG. 1 shows a graph.

| | Vaccination[a] | | Binding to AP33[b] | | | Sequenced[c] |
|---|---|---|---|---|---|---|
| Ab2 | Tested | Outcome | IgG | LC | HC hybrid | $V_L$ & $V_H$ |
| A31B | No | | Positive | Negative | Negative | Yes |
| A31C | No | | Positive | Negative | Negative | Yes |
| A31D | Yes | Negative | Positive | Negative | Negative | Yes |
| A31E | No | | Positive | Negative | Negative | |
| A31F | No | | Positive | Negative | Negative | |
| A31G | No | | Positive | Negative | Negative | |
| A34A | No | | Positive | Negative | Negative | Yes |
| A34B | No | | Positive | Negative | Negative | |
| A34C | No | | Positive | Negative | Negative | Yes |
| A46A | No | | Positive | Negative | Negative | |
| A46B | Yes | Negative | Positive | Negative | Negative | Yes |
| A46C | No | | Positive | Negative | Negative | Yes |
| A46D | No | | Positive | Negative | Negative | |
| A49A | No | | Positive | Negative | Negative | |
| A49B | No | | Positive | Negative | Negative | |
| A49C | No | | Positive | Negative | Negative | |
| A49D | No | | Positive | Negative | Negative | |
| A49E | No | | Positive | Negative | Negative | |
| A49F | No | | Positive | Negative | Negative | Yes |
| A52B | No | | Positive | Negative | Negative | |
| A52C | No | | Positive | Negative | Negative | Yes |
| A52D | No | | Positive | Negative | Negative | |
| A52E | No | | Positive | Negative | Negative | |
| A52F | No | | Positive | Negative | Negative | |
| A52G | No | | Positive | Negative | Negative | |
| A52H | No | | Positive | Negative | Negative | Yes |
| A52I | No | | Positive | Negative | Negative | |
| A52O | No | | Positive | Negative | Negative | |
| A52P | No | | Positive | Negative | Negative | |
| A53B | No | | Positive | Negative | Negative | |
| A53C | No | | Positive | Negative | Negative | |
| A53D | Yes | Negative | Positive | Negative | Negative | |
| A53E | No | | Positive | Negative | Negative | |
| A53I | No | | Positive | Negative | Negative | |
| A53J | No | | Positive | Negative | Negative | |
| A53K | No | | Positive | Negative | Negative | |
| A53M | No | | Positive | Negative | Negative | Yes |
| A53N | No | | Positive | Negative | Negative | |
| A53O | No | | Positive | Negative | Negative | Yes |
| A53P | No | | Positive | Negative | Negative | |
| A57B | No | | Positive | Negative | Negative | |
| A57C | No | | Positive | Negative | Negative | |
| A57D | No | | Positive | Negative | Negative | Yes |
| A57F | No | | Positive | Negative | Negative | |
| A57G | No | | Positive | Negative | Negative | Yes |
| A57H | No | | Positive | Negative | Negative | |
| A57J | No | | Positive | Negative | Negative | |
| A57O | No | | Positive | Negative | Negative | |
| A71.2 | No | | Positive | Negative | Negative | |
| A71.5 | No | | Positive | Negative | Negative | |
| A71.9 | No | | Positive | Negative | Negative | |
| B2.1A | No | | Positive | Negative | Negative | Yes |
| B2.1B | No | | Positive | Negative | Negative | |
| B4.1A | No | | Positive | Negative | Negative | |
| B4.1D | Yes | Negative | Positive | Negative | Negative | Yes |
| B4.1E | Yes | Negative | Positive | Negative | Negative | Yes |
| B4.1F | Yes | Negative | Positive | Negative | Negative | Yes |
| B4.1G | No | | Positive | Negative | Negative | Yes |
| K201 | Yes | Negative | Positive | Negative | Negative | Yes |
| K271 | No | | Positive | Negative | Negative | |
| K391 | Yes | Negative | Positive | Negative | Negative | Yes |
| 2K19 | Yes | Negative | Positive | Negative | Negative | Yes |
| 2K49 | Yes | Negative | Positive | Negative | Negative | |
| 2K55 | Yes | Negative | Positive | Negative | Negative | Yes |
| 2K56 | Yes | Negative | Positive | Negative | Negative | Yes |
| 2K160 | Yes | Negative | Positive | Negative | Negative | Yes |
| L1.1A | No | | Positive | Negative | Negative | Yes |
| L1.1D | Yes | Negative | Positive | Negative | Negative | |
| L1.2A | Yes | Negative | Positive | Negative | Negative | Yes |
| L1.2B | No | | Positive | Negative | Negative | |
| L1.2C | No | | Positive | Negative | Negative | Yes |
| L1.2D | No | | Positive | Negative | Negative | Yes |
| L1.2E | No | | Positive | Negative | Negative | Yes |
| L1.2F | No | | Positive | Negative | Negative | Yes |
| L1.2H | No | | Positive | Negative | Negative | |
| L1.2I | No | | Positive | Negative | Negative | Yes |
| L1.2K | No | | Positive | Negative | Negative | Yes |
| L1.2L | No | | Positive | Negative | Negative | |
| L1.2M | No | | Positive | Negative | Negative | |
| L1.2N | No | | Positive | Negative | Negative | |
| L1.2O | No | | Positive | Negative | Negative | |
| L1.2P | No | | Positive | Negative | Negative | Yes |
| P1.52 | Yes | Negative | Positive | Negative | Negative | Yes |
| P1.T | Yes | Negative | Positive | Negative | Negative | Yes |

[a] Balb/c mice were vaccinated with purified antibody coupled to KLH and the immune sera were tested for reactivity with E2. A negative result denotes lack of reactivity. An example of negative ELISA data is shown separately
[b] Binding of the Ab2s to (a) AP33 whole IgG, (b) AP33 light-chain alone and (c) a hybrid comprising AP33 heavy-chain and an irrelevant κ-light-chain. None of the Ab2s bound AP33 LC or HC hybrid.
[c] Sequencing of Ab2 variable regions.

Over the course of 18 months, twenty-five Ab2s were picked at random and used to vaccinate mice (Table A), in order to identify one or more internal-image antibodies (Ab23) that would be capable of eliciting an immune response to HCV E2. The immune sera were tested by ELISA for:
1. Blocking of AP33-Ab2 interaction.
2. Binding to E2.
3. Inhibition of HCV infection in cell culture RESULTS: The immune sera strongly inhibited binding of AP33 to Ab2, indicating that they contained anti-Ab2 antibodies. However, the anti-Ab2 antibodies did not bind to E2, nor did they inhibit HCV in cell culture. This was a significant problem. See FIGS. 2 and 3 for an example of these negative results.

FIG. 1 shows inhibition of AP33 binding to A164 by immune sera

Six Balb/c mice were vaccinated with A164 conjugated to KLH. Primary vaccination was followed by 4 boosters at 14-day intervals, and a final bleed taken 5 days after the last booster.

Serial dilutions of pre-immune and immune sera were co-incubated with biotinylated AP33 (b-AP33) on A164-coated microtitre plates. Binding of b-AP33 was detected with streptavidin-HRP and TMB. A decreased signal indicates blocking of b-AP33-A164 interaction by competing serum antibodies. The graph represents the response of two mice (No 1 & 2) within the group. All other animals showed the same response.

RESULT: The immune sera contain A164-specific antibodies that block AP33 binding to E2, whereas the pre-immune bleeds have no effect on the interaction.

Figure 2:
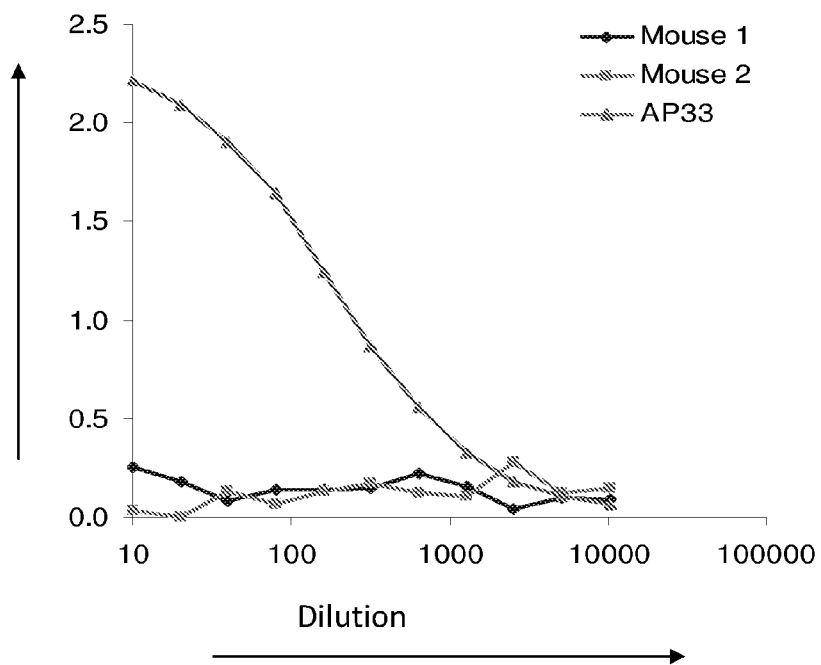
FIG. 2 shows a graph.

FIG. 2 shows binding of serum antibodies to E2—example of negative result Six Balb/c mice were vaccinated with A164 conjugated to KLH. Primary vaccination was followed by 4 boosters at 14-day intervals, and a final bleed taken 5 days after the last booster.

Serial dilutions of immune sera were incubated on E2-coated microtitre plates. Binding of serum antibodies was detected with anti-mouse-HRP and TMB. An increased signal indicates the presence of E2-specific antibodies. AP33 served as a positive control. The graph represents the response of two mice (No 1 & 2) within the group. All other animals showed the same response.

RESULT: The immune sera from mice immunized with A164 do not contain antibodies that recognize E2.

Figure 3:
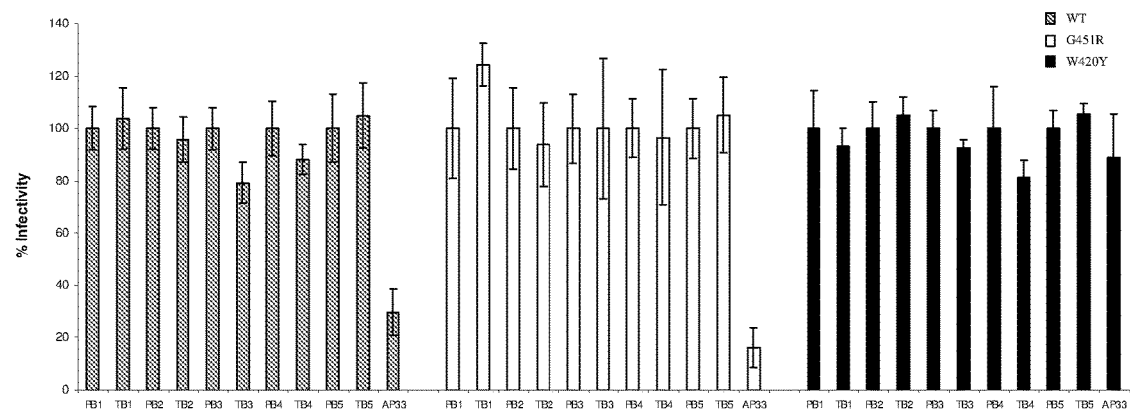
FIG. 3 shows a bar chart.

FIG. 3 shows virus neutralization by immune sera—example of negative result Wild type JFH1 virus (WT) and two E2 mutant viruses, G451R and W420Y were incubated with sera (1/100 dilution) obtained from mice immunized with the Ab2 P1T (TB=terminal bleed). Serum was taken from the same mice prior to immunization and served as controls (PB=pre-bleed). After 1 hour at 37° C., the virus/serum mixture was used to infect Huh7-J20 cells. The Huh7-J20 cell-line is engineered to release secreted alkaline phosphatase (SEAP) reporter into the medium following HCV infection, thus enabling a rapid and sensitive quantification of virus infectivity. At 3 hours post-infection, the inoculum was replaced with fresh medium and incubated for 72 hours. The virus infectivity levels were determined by measurement of SEAP released into the medium. The percent infectivity was calculated by quantifying viral infectivity in the presence of mouse immune serum (TB) relative to its respective control non-immune serum (PB). Error bars indicate standard deviation from the mean. A33 is included as a control. The G451R virus is more sensitive than WT to neutralization by AP33. The W420Y virus is resistant to neutralization by AP33.

RESULT: Infectivity of WT and G451R virus is significantly reduced by pre-incubation with AP33, but not by any of the mouse sera, indicating that the immune sera from mice immunized with P1T do not contain neutralizing antibodies.

Obtaining B2.1A Antibody

Figure 4:
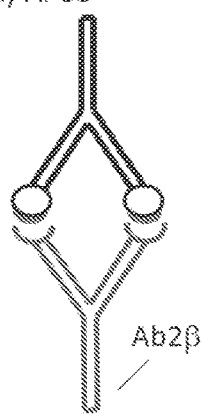
FIG. 4 shows a diagram.
Figure 4:
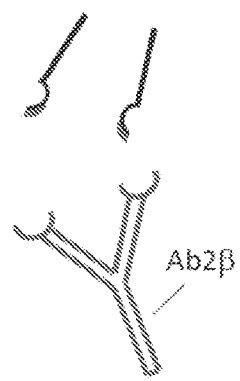
Figure 4:
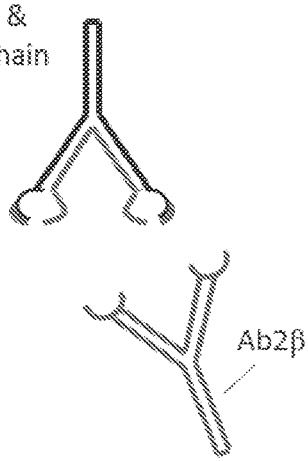
Figures 5, 6:
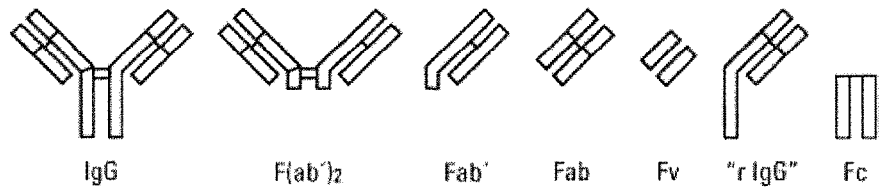
FIG. 5 shows HCV E2 sequence.
FIG. 6 shows examples of antibodies and antigen binding fragments of the invention.

These results presented a significant challenge: how to identify the Ab2βs?
By immunisation to produce Ab3
By testing for binding to AP33 light chain and heavy chain
This is illustrated in FIG. 4.
Result: all 120 Ab2s behave like Ab2β
We realised that there were problems in screening 122 antibodies by vaccination, for example time constraints and/or the number of animals that would be required, so we did the following:

1. We compared the binding of the Ab2s to (a) AP33 whole IgG, (b) AP33 light-chain alone and (c) a hybrid comprising AP33 heavy-chain and an irrelevant κ-light-chain. This approach is illustrated in FIG. 4., and is based on the expectation that an Ab2β would bind to the entire antigen-binding pocket present in (a) but it would not bind to (b) or (c), whereas an Ab2 that did not represent an internal-image of the antigen-binding pocket would bind to either (b) or (c) In fact, all the Ab2s behaved as Ab2βs and bound only to (a), so this assay failed to differentiate between them.
2. We sequenced the variable regions of all the Ab2s, to remove any duplicates. This reduced the panel to 18 unique antibodies.

Our crystal structure of AP33 Fab complexed with a peptide corresponding to its epitope allowed us to identify the amino acid residues that make up the antigen-binding pocket of AP33. Using a panel of mutant AP33 antibodies in which these residues were individually replaced by alanine, we established which amino acid residues are involved in E2 binding and which are not (Potter et al. 2012 and Table 1 below).

The same panel of mutant AP33 antibodies was used to differentiate between the Ab2s. This approach proved to be a real breakthrough, because it revealed striking differences between the Ab2s. Some were unaffected by the mutations, whereas others shared binding characteristics with E2. The binding profile of B2.1A most closely resembled that of E2 (Table 1).

TABLE 1

Binding of Ab2s to wild-type and mutant AP33, data obtained November 2011-January 2012

| | | | | | Relative strength of binding (%) | | | | | | | | | | | Score[d] = binding reduced by | |
|---|---|---|---|---|---|---|---|---|---|---|---|---|---|---|---|---|---|
| | WT | AP33 light chain mutants[a] | | | | | | | AP33 heavy chain mutants[a] | | | | | | | | |
| | AP33 | $Y_L28A$ | $N_L30A$ | $F_L32A$ | $N_L91A$ | $N_L92A$ | $V_L93A$ | $D_L94A$ | $W_L96A$ | $Y_H33A$ | $Y_H50A$ | $Y_H53A$ | $Y_H58A$ | $I_H95A$ | $T_H97A$ | $Y_H100A$ | >50% | >80% |
| E2[b] | 100 | 111.9 | 88.8 | -3.5 | 6.6 | 59.8 | 79 | 74.4 | -0.4 | 2.5 | -1 | 100.4 | 0.7 | 9.9 | 100.6 | 4.9 | 8 | 8 |
| Anti-Id[c] | | | | | | | | | | | | | | | | | | |
| B.2.1A | 100 | 82 | 73 | 21 | 36 | 36 | 49 | 41 | 1 | 10 | 4 | 68 | 5 | 29 | 89 | 8 | 8 | 5 |
| L.1.1A | 100 | 5 | 88 | 3 | 85 | 83 | 88 | 86 | 1 | 26 | 9 | 85 | 9 | 26 | 84 | 13 | 7 | 5 |
| P1.T | 100 | 20 | 88 | 54 | 18 | 48 | 72 | 50 | 4 | 67 | 15 | 90 | 13 | 15 | 86 | 11 | 6 | 6 |
| L.1.2A | 100 | 76 | 90 | 52 | 31 | 63 | 83 | 88 | 1 | 30 | 24 | 88 | 9 | 41 | 86 | 54 | 6 | 2 |
| A16A | 100 | 93 | 92 | 64 | 57 | 66 | 82 | 70 | 7 | 15 | 35 | 46 | 40 | 63 | 75 | 10 | 5 | 3 |
| K391 | 100 | 112 | 74 | 45 | 66 | 82 | 77 | 82 | 14 | 91 | 37 | 82 | 41 | 35 | 98 | 54 | 5 | 1 |
| A53M | 100 | 80 | 85 | 55 | 21 | 86 | 77 | 89 | 11 | 94 | 88 | 104 | 59 | 54 | 98 | 17 | 3 | 2 |
| 2K55 | 100 | 87 | 69 | 23 | 81 | 83 | 84 | 88 | 1 | 50 | 27 | 77 | 61 | 60 | 92 | 89 | 3 | 1 |
| 2K49 | 100 | 21 | 93 | 43 | 94 | 105 | 94 | 97 | 70 | 29 | 90 | 88 | 91 | 84 | 93 | 25 | 3 | 0 |
| B4.1F | 100 | 79 | 95 | 49 | 75 | 78 | 100 | 92 | 10 | 76 | 79 | 94 | 62 | 74 | 97 | 57 | 2 | 1 |
| K201 | 100 | 79 | 90 | 68 | 89 | 115 | 96 | 90 | 3 | 55 | 34 | 79 | 67 | 57 | 104 | 82 | 2 | 1 |
| 2K56 | 100 | 89 | 84 | 61 | 88 | 90 | 86 | 94 | 1 | 57 | 39 | 74 | 67 | 66 | 90 | 83 | 2 | 1 |
| A5 | 100 | 90 | 98 | 53 | 98 | 105 | 98 | 100 | 4 | 81 | 54 | 89 | 71 | 74 | 98 | 88 | 1 | 1 |
| 2K19 | 100 | 96 | 88 | 75 | 90 | 94 | 88 | 97 | 2 | 72 | 54 | 79 | 73 | 75 | 96 | 88 | 1 | 1 |
| A1.5 | 100 | 82 | 98 | 94 | 94 | 100 | 96 | 98 | 55 | 93 | 86 | 69 | 85 | 65 | 96 | 78 | 0 | 0 |
| A164 | 100 | 60 | 100 | 66 | 83 | 106 | 98 | 106 | 70 | 73 | 68 | 65 | 93 | 72 | 95 | 59 | 0 | 0 |
| 2K160 | 100 | 78 | 100 | 82 | 86 | 82 | 90 | 104 | 96 | 90 | 91 | 80 | 94 | 91 | 97 | 75 | 0 | 0 |
| P1.52 | 100 | 96 | 103 | 79 | 95 | 105 | 106 | 107 | 64 | 84 | 79 | 102 | 71 | 89 | 94 | 80 | 0 | 0 |

[a]The amino acid residues that comprise the antigen-binding pocket were identified from the crystal structure of AP33 Fab complexed with a peptide corresponding to its epitope. Mutant AP33 antibodies were made in which these residues were individually replaced by alanine. The mutants were named according to the identity and position of the wild type (WT) amino acid, eg $Y_L28A$ has tyrosine at position 28 in the light chain changed to alanine.
[b]The reactivity of HCV E2 with each mutant was determined by ELISA and expressed as a percentage of reactivity with WT AP33.
[c]The reactivity of each anti-idiotype (anti-Id) with each mutant was determined by ELISA and expressed as a percentage of reactivity with WT AP33.
[d]The score is the number of mutants to which binding was reduced by >50% and >80% relative to WT AP33. Values contributing to the score are highlighted.

RESULT: AP33 binding to E2 was reduced by >90% by mutation of light chain residues F32, N91 and W96, and of heavy chain residues Y33, Y50, Y58, I95 and Y100 (values highlighted in bold, double underlined). The same eight mutations reduced AP33 binding to anti-Id B2.1A (top line, values highlighted in bold and boxed), whereas binding to other anti-Ids was affected by fewer, or none of the mutations, which shows that B2.1A most closely resembles E2. Binding to some anti-Ids was reduced by mutations that did not affect E2 binding (eg $Y_L28A$), therefore these reduced values are not highlighted or included in the score.

Figure 7:
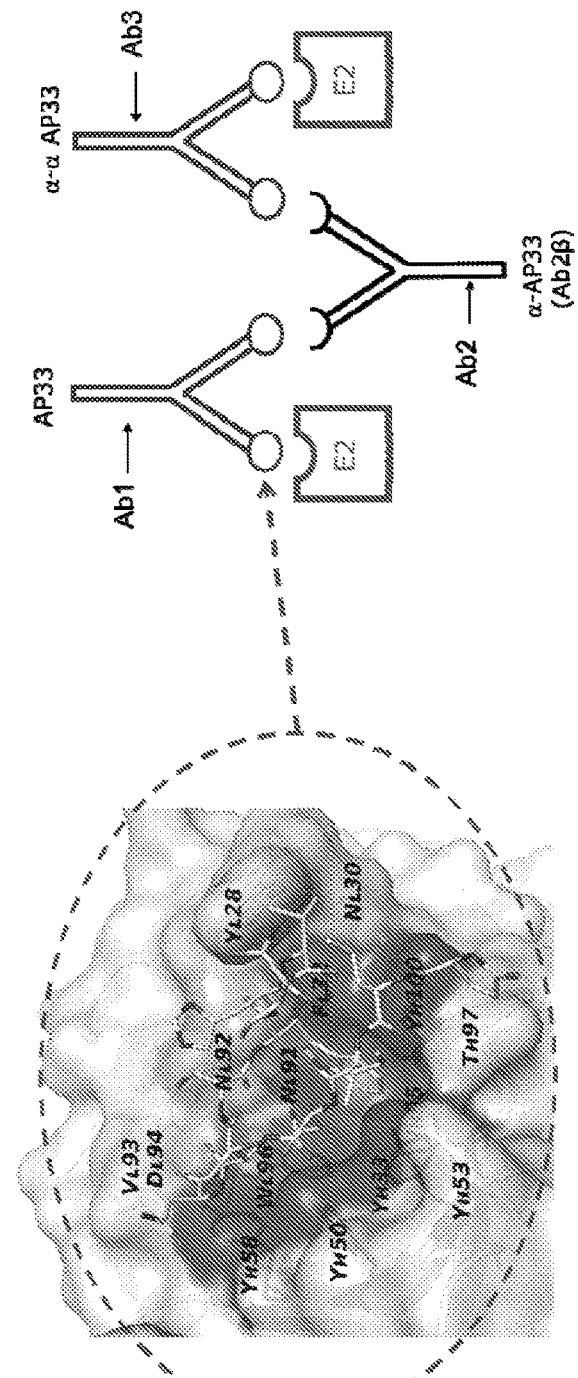
FIG. 7 shows The molecular surface of the AP33 binding pocket.

Example 2.1: Selection of an Anti-idiotypic Antibody that Represents an Internal Image of the AP33 Paratope FIG. 7 shows the molecular surface of the AP33 binding pocket. The positions of eight alanine substitutions that reduced binding by >90% are colored purple, while those that had little or no effect on E2 binding are colored cyan. The epitope peptide is shown as sticks with yellow carbon atoms.

FIG. 7 also shows a schematic diagram to illustrate the principles of the anti-idiotype network theory. Exposure to antigen induces the production of antibodies, termed Ab1. The specificity of an Ab1 antibody is determined by the sequence and structure of its hypervariable regions, and this unique antigen-binding site is also recognised as a set of idiotypic epitopes, or idiotopes, by the immune system. Anti-idiotypic (anti-Id) antibodies generated against the Ab1 are termed Ab2, and a subset of these, termed Ab2β, fit into the antigen-binding site (paratope) of the Ab1 precisely enough to be an "internal image" of it, and, by the same token, an effective mimic of the original antigen. An Ab2β antibody can therefore be used as a surrogate antigen to elicit anti-anti-Id antibodies (Ab3), which have the same binding properties as the Ab1.

Balb/c mice were vaccinated with AP33 to generate a large number of hybridomas. These were screened for the production of Ab2 antibodies that were able to block the AP33-E2 interaction by binding to the hypervariable region of AP33.

To identify, from this panel of various anti-idiotypes, the desired Ab2β that represents an "internal image" of the AP33 paratope, we used a panel of AP33 antibody mutants, in which each residue within the antigen-binding pocket was individually mutated to alanine. Eight residues in the centre of the pocket were essential for E2 recognition, and the same eight residues were also required for binding of one of the Ab2s, designated B2.1A. This indicates that the molecular surface of B2.1A closely resembles that of the AP33 epitope on E2.

Example 2.2: Vaccination with B2.1A Elicits Ab3 Antibodies that Recognise HCV E2

Balb/c mice were vaccinated with B2.1A conjugated to KLH. A different adjuvant was used for each group of four mice: (A) Complete Freunds/Incomplete Freunds (CFA/IFA); (B) Alum; (C) Alum & lipopolysaccharide (LPS); (D) Quil-A. The immune and pre-immune sera were tested by ELISA for
1. Blocking of AP33-B2.1A interaction: Sera at 1:300 dilution were co-incubated with biotinylated AP33 (b-AP33) on B2.1A-coated microtitre plates. Decreased binding of b-AP33 to B2.1A indicates blocking of the interaction by competing serum antibodies.
2. Binding to E2: Sera at 1:300 dilution were incubated on E2-coated microtitre plates. Binding of serum antibodies indicates the presence of E2-specific Ab3 antibodies.

Result

Figure 8:
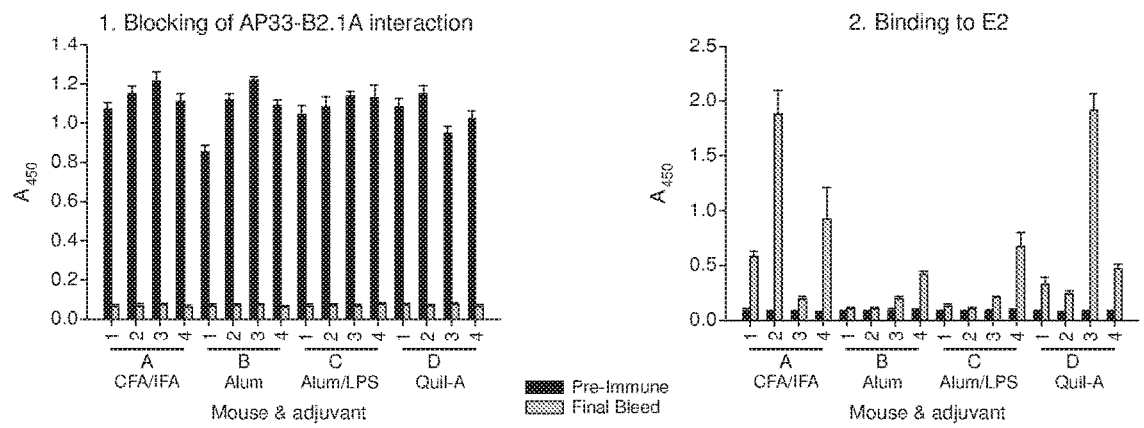
FIG. 8 shows bar charts.

All the immune sera strongly inhibited binding of b-AP33 to B2.1A, indicating that they contain B2.1A-specific antibodies. However, not all of them contain E2-specific antibodies. Immune sera A2 and D3 show the strongest E2 reactivity, with an anti-E2 titre of over 300. As expected, the pre-immune sera are uniformly negative. These results show that B2.1A is able to elicit an E2-specific response. See FIG. 8.

Example 2.3: Vaccination with B2.1A Elicits Ab3 Antibodies that Bind to the Same Epitope as AP33

A) Peptide Inhibition

Immune sera A2 and D3 and anti-E2 monoclonal antibodies (MAbs) AP33 and ALP98 were pre-incubated with peptide, transferred to E2-coated microtitre plates and bound antibodies were detected with anti-mouse-HRP.

Result

The binding to E2 of Ab1 (AP33) and of Ab3 in the immune sera is specifically inhibited by a peptide that corresponds to the AP33 epitope. There is no inhibition by a peptide in which W420, an essential contact residue for AP33, has been replaced by R, nor by an unrelated control sequence. As expected, ALP98, which binds to a different linear epitope on E2, is not inhibited.

Figure 9:
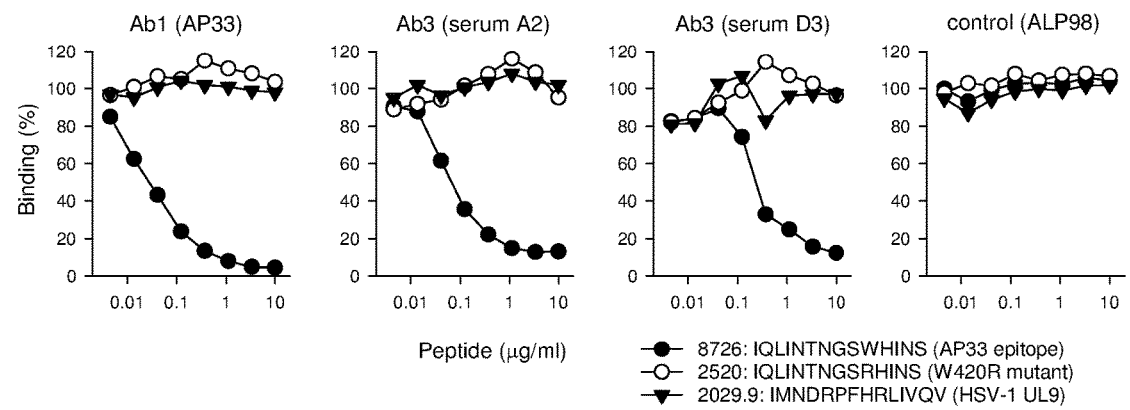
FIG. 9 shows graphs.

See FIG. 9.

B) Alanine Scanning Across AP33 the Epitope

ELISA was used to test the reactivity of Ab3 antibodies in immune sera A2 and D3 with a panel of E2 mutants, in which each residue across the AP33 epitope was individually replaced by alanine. MAbs AP33 and ALP98 served as positive and negative controls, respectively.

Result

The binding of AP33 to E2 was reduced by alanine substitution of L413, N415, G418 or W420. This agrees with our previous data[2] and with the crystal structure of the AP33-peptide complex, in which these four residues are buried at the molecular interface[1]. The binding profile of the Ab3 antibodies was very similar to that of AP33: Their binding to E2 was reduced or abrogated by the same four mutations, and also by alanine substitution of I414. As expected, the binding of ALP98 was not affected by any of the substitutions.

Figure 10:
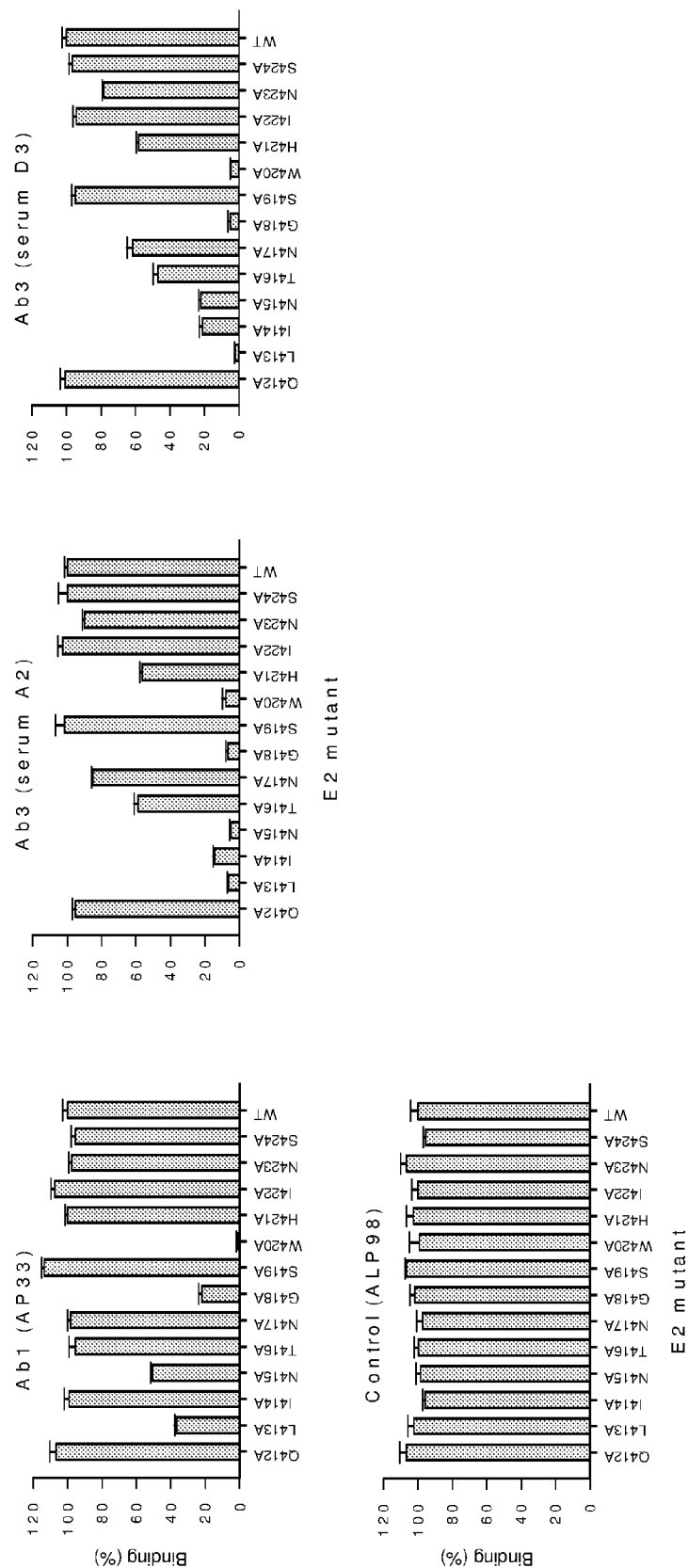
FIG. 10 shows bar charts.

This is compelling evidence that vaccination with B2.1A elicits AP33-like antibodies. See FIG. 10

Example 2.4. The Titre of E2-specific Ab3 Antibodies in Immune Sera

Figure 11:
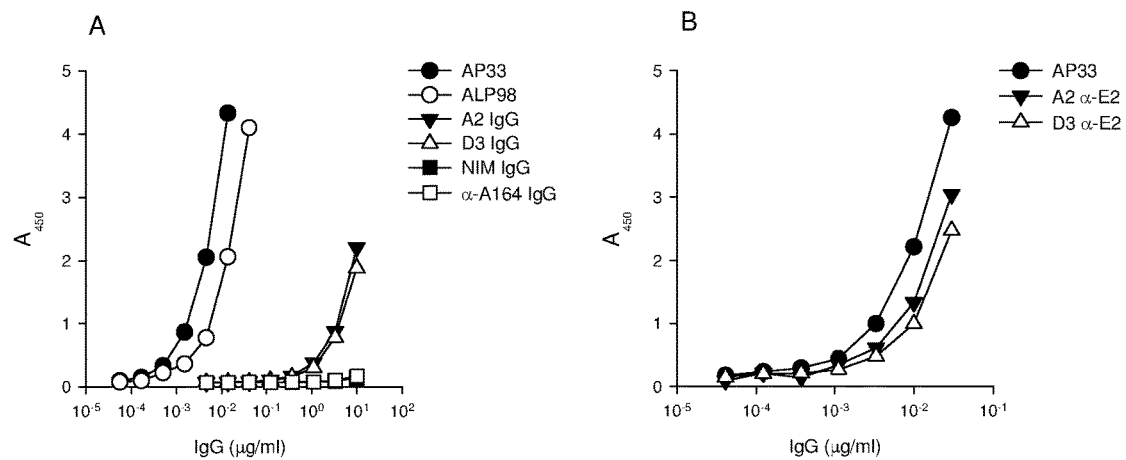
FIG. 11 shows graphs.
Figure 12:
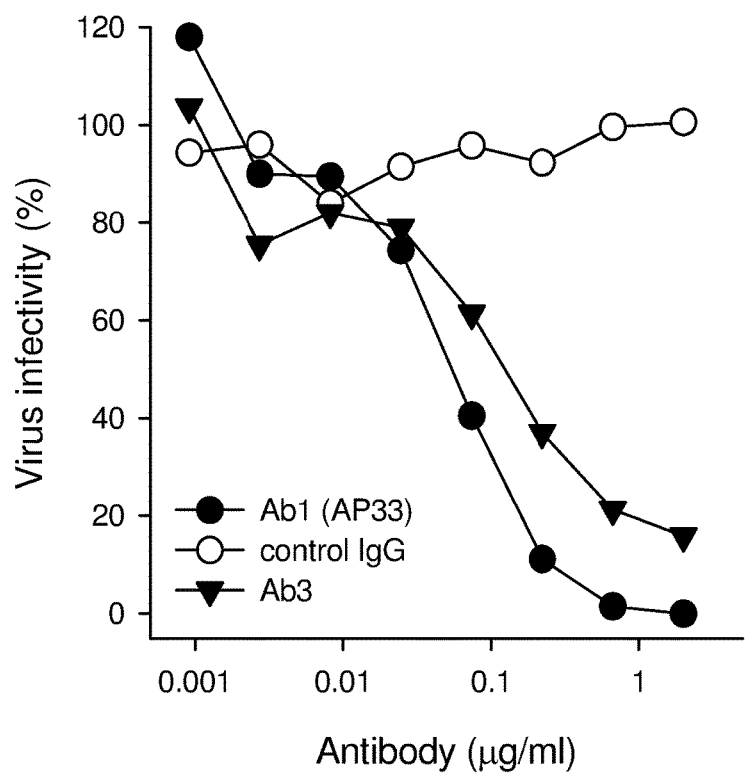
FIG. 12 shows a graph.

FIG. 11A shows Serial dilutions of purified total IgG from immune sera A2 and D3, from non-immune mouse serum (NIM) and from a mouse vaccinated with anti-Id A164 were tested for E2 binding by ELISA. MAbs AP33 and ALP98 served as positive controls.

FIG. 11B shows E2-specific Ab3 antibodies from immune sera A2 and D3 were affinity-purified on immobilized E2. Serial dilutions of the purified Ab3 antibodies and of AP33 were tested for E2 binding by ELISA.

Result

The anti-E2 titre of total IgG from sera A2 and D3 was about 1000-fold lower than that of AP33, whereas the anti-E2 titre of the E2-specific affinity-purified IgG was only 2- to 3-fold lower than that of AP33. Taken together, these data indicate that the proportion of E2-specific antibody to total IgG in the immune sera is in the range of 1/500-1/2000.

Example 2.5. Vaccination with B2.1A Elicits Ab3 Antibodies that Neutralize Virus HCVcc were pre-incubated for 1 h with serial dilutions of E2-specific IgG affinity-purified from the serum of a mouse vaccinated with B2.1A. The virus-IgG mix was used to infect Huh7-J20 reporter cells[3]. Virus growth was measured by the level of secreted alkaline phosphatase (SEAP) reporter present in the cell culture medium after 3 days. MAb AP33 and IgG purified from a mouse vaccinated with another anti-Id served as positive and negative controls, respectively.

Result

The Ab3 antibodies elicited by B2.1A neutralize virus infectivity very effectively, with an $IC_{50}$ that is about twice that of AP33.

Summary

We have used a broadly neutralizing antibody, AP33, as a template to reverse engineer an immunogen that induces similar antibodies upon vaccination. This has been achieved by isolating an anti-idiotypic antibody that represents the internal image of the AP33 binding pocket and thus mimics the protective epitope. We demonstrate, for the first time in the HCV vaccine field, the success of such a focused, structure-based approach.

REFERENCES TO EXAMPLE 2

1. Potter, J. A. et. al (2012). Towards a hepatitis C virus vaccine: the structural basis of hepatitis C virus neutralization by AP33, a broadly neutralizing antibody. *J. Virol.* 86, 12923-12932.

2. Tarr, A. W. et. al (2006). Characterization of the hepatitis C virus E2 epitope defined by the broadly neutralizing monoclonal antibody AP33. *Hepatology* 43, 592-601.

3. Iro, M. et. al (2009). A reporter cell line for rapid and sensitive evaluation of hepatitis C virus infectivity and replication. *Antivir. Res.* 83, 148-155.

Example 3: scFv's scFv's were produced from B2.1A. scFv amino acid sequences for eukaryotic such as mammalian expression and for prokaryotic such as bacterial expression are shown below.

Mammalian Expression Construct.

A mammalian expression construct containing the B2.1A scFv sequence was generated. This sequence was expressed in CHO cells and purified. The purified product was shown to interact with AP33 in ELISA. The B2.1A scFv protein sequence is shown below.

(SEQ ID NO: 11)

```
METDTLLLWVLLLWVPGSTGDANSQVQLQESGTELVKPGASVKLSCKASGYTFTNYWMHWVKQRPGQG

LEWIGEINPSDGHTNYNEKFKSKATLTVDKSSSTAYMQLSSLTSEDSAVYYCARPWAFGNYGAWFAYWGQ

GTLVTVSAGGSGGSGGGGSGGGGSGGGASDIVMTQSPKFMSTSVGDRVSITCKASQNVRTAVAWYQQ

KPGQSPKALIYLASSRHTGVPDRFTGSGSGTDFTLTISNVQSEDLADYFCLQHWNYPYTFGGGTKLEIKSR

HHHHHH
```

Text in underlined in dots = IgK leader sequence allowing secretion of the ScFv into cell culture medium
Boxed Text = vH sequence; CDRs underlined; predicted CDRs shaded
Text in bold = vL sequence; CDRs underlined; predicted CDRs shaded
Text underlined in dashes = linker sequence
Text double underlined = 6-his tag for affinity purification of scFv Bacterial Expression Construct.

The above B2.1A scFv mammalian expression construct was used as a template to provide the scFv-encoding sequence and this was sub-cloned in-frame to the maltose-binding protein (MBP) into the bacterial expression vector pMBP. The MBP-B2.1A scFv amino acid sequence is shown below. The scFv was expressed in bacteria and purified following cleavage of the MBP domain and tested in mouse immunization experiments. The bacterial scFv was effective in eliciting AP33-like antibodies, but less effective than the mammalian scFv.

The MBP-B2.1A scFv fusion protein sequence is shown below:

(SEQ ID NO: 12)

```
MKYYHHHHHHDYDHMKIEEGKLVIWINGDKGYNGLAEVGKKFEKDTGIKVTVEHPDKLEEKFPQVAATGD

GPDIIFWAHDRFGGYAQSGLLAEITPDKAFQDKLYPFTWDAVRYNGKLIAYPIAVEALSLIYNKDLLPNPPKT

WEEIPALDKELKAKGKSALMFNLQEPYFTWPLIAADGGYAFKYENGKYDIKDVGVDNAGAKAGLTFLVDLIK

NKHMNADTDYSIAEAAFNKGETAMTINGPWAWSNIDTSKVNYGVTVLPTFKGQPSKPFVGVLSAGINAAS
```

-continued

```
PNKELAKEFLENYLLTDEGLEAVNKDKPLGAVALKSYEEELAKDPRIAATMENAQKGEIMPNIPQMSAFWY

AVRTAVINAASGRQTVDEALKDAQTNSSSNNNNNNNNNNLGENLYFQGA/MAQVQLQESGTELVKPGA

SVKLSCKASGYTFTNYWMHWVKQRPGQGLEWIGEINPSDGHTNYNEKFKSKATLTVDKSSSTAYMQLSSL

TSEDSAVYYCARPWARGNYGAWFAYWGQGTLVTVSAGGSGGSGGGGSGGGGSGGGASDIVMTQSPKF

MSTSVGDRVSITCKASQNVRTAVAWYQQKPGQSPKALIYLASSRHTGVPDRFTGSGSGTDFTLTISNVQ

SEDLADYFCLQHWNYPYTFGGGTKLE
```

Cleaved Sequence:

(SEQ ID NO: 13)
```
MAQVQLQESGTELVKPGASVKLSCKASGYTFTNYWMHWVKQRPGQGLEWIGEINPSDGHTNYNEKFKS

KATLTVDKSSSTAYMQLSSLTSEDSAVYYCARPWARGNYGAWFAYWGQGTLVTVSAGGSGGSGGGGSG

GGGSGGGASDIVMTQSPKFMSTSVGDRVSITCKASQNVRTAVAWYQQKPGQSPKALIYLASSRHTGVP

DRFTGSGSGTDFTLTISNVQSEDLADYFCLQHWNYPYTFGGGTKLE
```

Text in underlined in dots = MBP sequence
/ = proteolytic cleavage site to remove MBP from the MBP-scFv fusion protein
boxed text = vH sequence; CDRs underlined; preferred CDRs shaded

Text in bold = vL sequence; CDRs underlined; preferred CDRs shaded

Text underlined in dashes = linker sequence

Nucleic Acid Constructs

In the exemplary sequences presented below, the coding sequence may be separately taken and placed into the vector of choice if the skilled worker desires.

pDisMod2-B2.1A-scFv—Example Sequence

A modified pDisplay vector carrying the B2.1A scFv sequence (the coding sequence is highlighted)
scFv coding sequence key as follows:
Leader sequence-vH-linker-vL-6his tag-STOP (SEQ ID NO: 16)
```
  1 GCGCGCGTTG ACATTGATTA TTGACTAGTT ATTAATAGTA ATCAATTACG GGTCATTAG

61 TTCATAGCCC ATATATGGAG TTCCGCGTTA CATAACTTAC GGTAAATGGC CCGCCTGGCT

121 GACCGCCCAA CGACCCCGC CCATTGACGT CAATAATGAC GTATGTTCCC ATAGTAACGC

181 CAATAGGGAC TTTCCATTGA CGTCAATGGG TGGACTATTT ACGGTAAACT GCCCACTTGG

241 CAGTACATCA AGTGTATCAT ATGCCAAGTA CGCCCCCTAT TGACGTCAAT GACGGTAAAT

301 GGCCCGCCTG GCATTATGCC CAGTACATGA CCTTATGGGA CTTTCCTACT TGGCAGTACA

361 TCTACGTATT AGTCATCGCT ATTACCATGG TGATGCGGTT TTGGCAGTAC ATCAATGGGC

421 GTGGATAGCG GTTTGACTCA CGGGGATTTC CAAGTCTCCA CCCCATTGAC GTCAATGGGA

481 GTTTGTTTTG GCACCAAAAT CAACGGGACT TTCCAAAATG TCGTAACAAC TCCGCCCCAT

541 TGACGCAAAT GGGCGGTAGG CGTGTACGGT GGGAGGTCTA TATAAGCAGA GCTCTCTGGC

601 TAACTAGAGA ACCCACTGCT TACTGGCTTA TCGAAATTAA TACGACTCAC TATAGGGAGA

661 CCCAAGCTTG GTACCGAGCT CGGATCTACT AGTAACGGCC GCCAGTGTGC TGGATTTCGG

721 CTTGGGGATA TCCACCATGG AGACAGACAC ACTCCTGCTA TGGGTACTGC TGCTCTGGGT
```

-continued

```
 781 TCCAGGTTCC ACTGGTGACG CGAATTCGCA GGTTCAGCTG CAGGAGTCTT GGGCTGAGCT

841 GGTGAAGCCT GGGGCTTCAG TGAAGCTGTC CTGCAAGGCT TCTGGCTACA CCTTCACCAA

901 CTACTGGATG CACTGGGTTA AGCAGAGGCC TGGACAAGGC CTTGAGTGGA TTGGAGAGAT

961 TAATCCTAGC GACGGTCATA CTAACTACAA TGAAGAGTTC AAGAGCAAGG CCACACTGAC

1021 TGTAGACAAA TCCTCCAGCA CAGCCTACAT GCAACTCAGC AGCCTGACAT CTGAGGACTC

1081 TGCGGTCTAT TACTGTGCAA GACCTTGGGC GTTTGGTAAC TACGGGGCCT GGTTTGCTTA

1141 CTGGGGCCAA GGGACTCTGG TCACTGTCTC TGCCGGGGGA TCCGGTGGAT CAGGAGGTGG

1201 CGGATCTGGT GGAGGCGGTT CAGGAGGAGG TGCTAGCGAT ATAGTGATGA CCCAGTCTCC

1261 AAAATTCATG TCCACATCAG TAGGAGACAG GGTCAGCATC ACCTGCAAGG CCAGTCAGAA

1321 TGTTCGTACT GCTGTAGCCT GGTATCAACA GAAACCAGGG CAGTCTCCTA AAGCACTGAT

1381 TTACTTGGCA TCCAGCCGGC ACACTGGAGT CCCTGATCGC TTCACAGGCA GTGGATCTGG

1441 GACAGATTTC ACTCTCACCA TTAGCAATGT GCAATCTGAA GACCTGGCAG ATTATTTCTG

1501 TCTGCAACAT TGGAATTATC CGTACACGTT CGGAGGGGGG ACCAAGTCTA GACATCACCA

1561 TCACCATCAC TAGGCTTCCG CTCGAGATCA GCCTCGACTG TGCCTTCTAG TTGCCAGCCA

1621 TCTGTTGTTT GCCCCTCCCC CGTGCCTTCC TTGACCCTGG AAGGTGCCAC TCCCACTGTC

1681 CTTTCCTAAT AAAATGAGGA AATTGCATCG CATTGTCTGA GTAGGTGTCA TTCTATTCTG

1741 GGGGGTGGGG TGGGGCAGGA CAGCAAGGGG GAGGATTGGG AAGACAATAG CAGGCATGCT

1801 GGGGATGCGG TGGGCTCTAT GGCTTCTGAG GCGGAAAGAA CCAGTGGCGG TAATACGGTT

1861 ATCCACAGAA TCAGGGGATA ACGCAGGAAA GAACATGTGA GCAAAAGGCC AGCAAAAGGC

1921 CAGGAACCGT AAAAAGGCCG CGTTGCTGGC GTTTTTCCAT AGGCTCCGCC CCCCTGACGA

1981 GCATCACAAA AATCGACGCT CAAGTCAGAG GTGGCGAAAC CCGACAGGAC TATAAAGATA

2041 CCAGGCGTTT CCCCCTGGAA GCTCCCTCGT GCGCTCTCCT GTTCCGACCC TGCCGCTTAC

2101 CGGATACCTG TCCGCCTTTC TCCCTTCGGG AAGCGTGGCG CTTTCTCATA GCTCACGCTG

2161 TAGGTATCTC AGTTCGGTGT AGGTCGTTCG CTCCAAGCTG GGCTGTGTGC ACGAACCCCC

2221 CGTTCAGCCC GACCGCTGCG CCTTATCCGG TAACTATCGT CTTGAGTCCA ACCCGGTAAG

2281 ACACGACTTA TCGCCACTGG CAGCAGCCAC TGGTAACAGG ATTAGCAGAG CGAGGTATGT

2341 AGGCGGTGCT ACAGAGTTCT TGAAGTGGTG GCCTAACTAC GGCTACACTA GAAGGACAGT

2401 ATTTGGTATC TGCGCTCTGC TGAAGCCAGT TACCTTCGGA AAAAGAGTTG GTAGCTCTTG

2461 ATCCGGCAAA CAAACCACCG CTGGTAGCGG TGGTTTTTTT GTTTGCAAGC AGCAGATTAC

2521 GCGCAGAAAA AAAGGATCTC AAGAAGATCC TTTGATCTTT TCTACGGGGT CTGACGCTCA

2581 GTGGAACGAA AACTCACGTT AAGGGATTTT GGTCATGAGA TTATCAAAAA GGATCTTCAC

2641 CTAGATCCTT TTAAATTAAA AATGAAGTTT TAAATCAATC TAAAGTATAT ATGAGTAACC

2701 TGAGGCTATG GCAGGGCCTG CCGCCCCGAC GTTGGCTGCG AGCCCTGGGC CTTCACCCGA

2761 ACTTGGGGGG TGGGGTGGGG AAAAGGAAGA AACGCGGGCG TATTGGCCCC AATGGGGTCT

2821 CGGTGGGGTA TCGACAGAGT GCCAGCCCTG GGACCGAACC CCGCGTTTAT GAACAAACGA

2881 CCCAACACCG TGCGTTTTAT TCTGTCTTTT TATTGCCGTC ATAGCGCGGG TTCCTTCCGG

2941 TATTGTCTCC TTCCGTGTTT CAGTTAGCCT CCCCCTAGGG TGGGCGAAGA ACTCCAGCAT
```

-continued

```
3001 GAGATCCCCG CGCTGGAGGA TCATCCAGCC GGCGTCCCGG AAAACGATTC CGAAGCCCAA

3061 CCTTTCATAG AAGGCGGCGG TGGAATCGAA ATCTCGTGAT GGCAGGTTGG GCGTCGCTTG

3121 GTCGGTCATT TCGAACCCCA GAGTCCCGCT CAGAAGAACT CGTCAAGAAG GCGATAGAAG

3181 GCGATGCGCT GCGAATCGGG AGCGGCGATA CCGTAAAGCA CGAGGAAGCG GTCAGCCCAT

3241 TCGCCGCCAA GCTCTTCAGC AATATCACGG GTAGCCAACG CTATGTCCTG ATAGCGGTCC

3301 GCCACACCCA GCCGGCCACA GTCGATGAAT CCAGAAAAGC GGCCATTTTC CACCATGATA

3361 TTCGGCAAGC AGGCATCGCC ATGGGTCACG ACGAGATCCT CGCCGTCGGG CATGCTCGCC

3421 TTGAGCCTGG CGAACAGTTC GGCTGGCGCG AGCCCCTGAT GCTCTTGATC ATCCTGATCG

3481 ACAAGACCGG CTTCCATCCG AGTACGTGCT CGCTCGATGC GATGTTTCGC TTGGTGGTCG

3541 AATGGGCAGG TAGCCGGATC AAGCGTATGC AGCCGCCGCA TTGCATCAGC CATGATGGAT

3601 ACTTTCTCGG CAGGAGCAAG GTGAGATGAC AGGAGATCCT GCCCCGGCAC TTCGCCCAAT

3661 AGCAGCCAGT CCCTTCCCGC TTCAGTGACA ACGTCGAGCA CAGCTGCGCA AGGAACGCCC

3721 GTCGTGGCCA GCCACGATAG CCGCGCTGCC TCGTCTTGCA GTTCATTCAG GCACCGGAC

3781 AGGTCGGTCT TGACAAAAAG AACCGGGCGC CCCTGCGCTG ACAGCCGGAA CACGGCGGCA

3841 TCAGAGCAGC CGATTGTCTG TTGTGCCCAG TCATAGCCGA ATAGCCTCTC CACCCAAGCG

3901 GCCGGAGAAC CTGCGTGCAA TCCATCTTGT TCAATCATGC GAAACGATCC TCATCCTGTC

3961 TCTTGATCGA TCTTTGCAAA AGCCTAGGCC TCCAAAAAAG CCTCCTCACT ACTTCTGGAA

4021 TAGCTCAGAG GCCGAGGAGG CGGCCTCGGC CTCTGCATAA ATAAAAAAAA TTAGTCAGCC

4081 ATGGGGCGGA GAATGGGCGG AACTGGGCGG AGTTAGGGGC GGGATGGGCG GAGTTAGGGG

4141 CGGGACTATG GTTGCTGACT AATTGAGATG CATGCTTTGC ATACTTCTGC CTGCTGGGGA

4201 GCCTGGGGAC TTTCCACACC TGGTTGCTGA CTAATTGAGA TGCATGCTTT GCATACTTCT

4261 GCCTGCTGGG GAGCCTGGGG ACTTTCCACA CCCTAACTGA CACACATTCC ACAGCTGGTT

4321 CTTTCCGCCT CAGGACTCTT CCTTTTTCAA TAAATCAATC TAAAGTATAT ATGAGTAAAC

4381 TTGGTCTGAC AGTTACCAAT GCTTAATCAG TGAGGCACCT ATCTCAGCGA TCTGTCTATT

4441 TCGTTCATCC ATAGTTGCCT GACTCCCCGT CGTGTAGATA ACTACGATAC GGGAGGGCTT

4501 ACCATCTGGC CCCAGTGCTG CAATGATACC GCGAGACCCA CGCTCACCGG CTCCAGATTT

4561 ATCAGCAATA AACCAGCCAG CCGGAAGGGC CGAGCGCAGA AGTGGTCCTG CAACTTTATC

4621 CGCCTCCATC CAGTCTATTA ATTGTTGCCG GGAAGCTAGA GTAAGTAGTT CGCCAGTTAA

4681 TAGTTTGCGC AACGTTGTTG CCATTGCTAC AGGCATCGTG GTGTCACGCT CGTCGTTTGG

4741 TATGGCTTCA TTCAGCTCCG GTTCCCAACG ATCAAGGCGA GTTACATGAT CCCCCATGTT

4801 GTGCAAAAAA GCGGTTAGCT CCTTCGGTCC TCCGATCGTT GTCAGAAGTA AGTTGGCCGC

4861 AGTGTTATCA CTCATGGTTA TGGCAGCACT GCATAATTCT CTTACTGTCA TGCCATCCGT

4921 AAGATGCTTT TCTGTGACTG GTGAGTACTC AACCAAGTCA TTCTGAGAAT AGTGTATGCG

4981 GCGACCGAGT TGCTCTTGCC CGGCGTCAAT ACGGGATAAT ACCGCGCCAC ATAGCAGAAC

5041 TTTAAAAGTG CTCATCATTG GAAAACGTTC TTCGGGGCGA AAACTCTCAA GGATCTTACC

5101 GCTGTTGAGA TCCAGTTCGA TGTAACCCAC TCGTGCACCC AACTGATCTT CAGCATCTTT

5161 TACTTTCACC AGCGTTTCTG GGTGAGCAAA AACAGGAAGG CAAATGCCG CAAAAAGGG

5221 AATAAGGGCG ACACGGAAAT GTTGAATACT CATACTCTTC CTTTTTCAAT ATTATTGAAG

5281 CATTTATCAG GGTTATTGTC TCATGAGCGG ATACATATTT GAATGTATTT AGAAAAATAA

5341 ACAAATAGGG GTTCCGCGCA CATTTCCCCG AAAAGTGCCA CCTGACGCGC CCTGTAGCGG

5401 CGCATTAAGC GCGGCGGGTG TGGTGGTTAC GCGCAGCGTG ACCGCTACAC TTGCCAGCGC
```

-continued

```
5461 CCTAGCGCCC GCTCCTTTCG CTTTCTTCCC TTCCTTTCTC GCCACGTTCG CCGGCTTTCC

5521 CCGTCAAGCT CTAAATCGGG GGCTCCCTTT AGGGTTCCGA TTTAGTGCTT TACGGCACCT

5581 CGACCCCAAA AAACTTGATT AGGGTGATGG TTCACGTAGT GGGCCATCGC CCTGATAGAC

5641 GGTTTTTCGC CCTTTGACGT TGGAGTCCAC GTTCTTTAAT AGTGGACTCT TGTTCCAAAC

5701 TGGAACAACA CTCAACCCTA TCTCGGTCTA TTCTTTTGAT TTATAAGGGA TTTTGCCGAT

5761 TTCGGCCTAT TGGTTAAAAA ATGAGCTGAT TTAACAAAAA TTTAACGCGA ATTTTAACAA

5821 AATATTAACG CTTACAATTT AC
``` pDisMod2-B2.1A-scFv—Preferred Sequence

A modified pDisplay vector carrying the B2.1A scFv sequence (the coding
sequence is highlighted). There are TWO changes relative to Example Sequence
(SEQ ID NO: 16) above - these are in line 781 and are marked in bold.
scFv coding sequence key as follows:
Leader sequence-vH-linker-vL-6his tag-STOP (SEQ ID NO: 27)

```
   1 GCGCGCGTTG ACATTGATTA TTGACTAGTT ATTAATAGTA ATCAATTACG GGTCATTAG

61 TTCATAGCCC ATATATGGAG TTCCGCGTTA CATAACTTAC GGTAAATGGC CCGCCTGGCT

121 GACCGCCCAA CGACCCCCGC CCATTGACGT CAATAATGAC GTATGTTCCC ATAGTAACGC

181 CAATAGGGAC TTTCCATTGA CGTCAATGGG TGGACTATTT ACGGTAAACT GCCCACTTGG

241 CAGTACATCA AGTGTATCAT ATGCCAAGTA CGCCCCCTAT TGACGTCAAT GACGTAAAT

301 GGCCCGCCTG GCATTATGCC CAGTACATGA CCTTATGGGA CTTTCCTACT TGGCAGTACA

361 TCTACGTATT AGTCATCGCT ATTACCATGG TGATGCGGTT TTGGCAGTAC ATCAATGGGC

421 GTGGATAGCG GTTTGACTCA CGGGGATTTC CAAGTCTCCA CCCCATTGAC GTCAATGGGA

481 GTTTGTTTTG GCACCAAAAT CAACGGGACT TTCCAAAATG TCGTAACAAC TCCGCCCCAT

541 TGACGCAAAT GGGCGGTAGG CGTGTACGGT GGGAGGTCTA TATAAGCAGA GCTCTCTGGC

601 TAACTAGAGA ACCCACTGCT TACTGGCTTA TCGAAATTAA TACGACTCAC TATAGGGAGA

661 CCCAAGCTTG GTACCGAGCT CGGATCTACT AGTAACGGCC GCCAGTGTGC TGGATTTCGG

721 CTTGGGGATA TCCACCATGG AGACAGACAC ACTCCTGCTA TGGGTACTGC TGCTCTGGGT

781 TCCAGGTTCC ACTGGTGACG CGAATTCGCA GGTTCAGCTG CAGGAGTCTG GACTGAGCT

841 GGTGAAGCCT GGGGCTTCAG TGAAGCTGTC CTGCAAGGCT TCTGGCTACA CCTTCACCAA

901 CTACTGGATG CACTGGGTTA AGCAGAGGCC TGGACAAGGC CTTGAGTGGA TTGGAGAGAT

961 TAATCCTAGC GACGGTCATA CTAACTACAA TGAGAAGTTC AAGAGCAAGG CCACACTGAC

1021 TGTAGACAAA TCCTCCAGCA CAGCCTACAT GCAACTCAGC AGCCTGACAT CTGAGGACTC

1081 TGCGGTCTAT TACTGTGCAA GACCTTGGGC GTTTGGTAAC TACGGGGCCT GGTTTGCTTA

1141 CTGGGGCCAA GGGACTCTGG TCACTGTCTC TGCCGGGGGA TCCGGTGGAT CAGGAGGTGG

1201 CGGATCTGGT GGAGGCGGTT CAGGAGGAGG TGCTAGCGAT ATAGTGATGA CCCAGTCTCC

1261 AAAATTCATG TCCACATCAG TAGGAGACAG GGTCAGCATC ACCTGCAAGG CCAGTCAGAA

1321 TGTTCGTACT GCTGTAGCCT GGTATCAACA GAAACCAGGG CAGTCTCCTA AAGCACTGAT

1381 TTACTTGGCA TCCAGCCGGC ACACTGGAGT CCCTGATCGC TTCACAGGCA GTGGATCTGG

1441 GACAGATTTC ACTCTCACCA TTAGCAATGT GCAATCTGAA GACCTGGCAG ATTATTTCTG
```

-continued

```
1501 TCTGCAACAT TGGAATTATC CGTACACGTT CGGAGGGGGG ACCAAGTCTA GACATCACCA

1561 TCACCATCAC TAGGCTTCCG CTCGAGATCA GCCTCGACTG TGCCTTCTAG TTGCCAGCCA

1621 TCTGTTGTTT GCCCCTCCCC CGTGCCTTCC TTGACCCTGG AAGGTGCCAC TCCCACTGTC

1681 CTTTCCTAAT AAAATGAGGA AATTGCATCG CATTGTCTGA GTAGGTGTCA TTCTATTCTG

1741 GGGGGTGGGG TGGGGCAGGA CAGCAAGGGG GAGGATTGGG AAGACAATAG CAGGCATGCT

1801 GGGGATGCGG TGGGCTCTAT GGCTTCTGAG GCGGAAAGAA CCAGTGGCGG TAATACGGTT

1861 ATCCACAGAA TCAGGGGATA ACGCAGGAAA GAACATGTGA GCAAAAGGCC AGCAAAAGGC

1921 CAGGAACCGT AAAAAGGCCG CGTTGCTGGC GTTTTTCCAT AGGCTCCGCC CCCTGACGA

1981 GCATCACAAA AATCGACGCT CAAGTCAGAG GTGGCGAAAC CCGACAGGAC TATAAAGATA

2041 CCAGGCGTTT CCCCCTGGAA GCTCCCTCGT GCGCTCTCCT GTTCCGACCC TGCCGCTTAC

2101 CGGATACCTG TCCGCCTTTC TCCCTTCGGG AAGCGTGGCG CTTTCTCATA GCTCACGCTG

2161 TAGGTATCTC AGTTCGGTGT AGGTCGTTCG CTCCAAGCTG GGCTGTGTGC ACGAACCCCC

2221 CGTTCAGCCC GACCGCTGCG CCTTATCCGG TAACTATCGT CTTGAGTCCA ACCCGGTAAG

2281 ACACGACTTA TCGCCACTGG CAGCAGCCAC TGGTAACAGG ATTAGCAGAG CGAGGTATGT

2341 AGGCGGTGCT ACAGAGTTCT TGAAGTGGTG GCCTAACTAC GGCTACACTA GAAGGACAGT

2401 ATTTGGTATC TGCGCTCTGC TGAAGCCAGT TACCTTCGGA AAAAGAGTTG GTAGCTCTTG

2461 ATCCGGCAAA CAAACCACCG CTGGTAGCGG TGGTTTTTTT GTTTGCAAGC AGCAGATTAC

2521 GCGCAGAAAA AAAGGATCTC AAGAAGATCC TTTGATCTTT TCTACGGGGT CTGACGCTCA

2581 GTGGAACGAA AACTCACGTT AAGGGATTTT GGTCATGAGA TTATCAAAAA GGATCTTCAC

2641 CTAGATCCTT TTAAATTAAA AATGAAGTTT TAAATCAATC TAAAGTATAT ATGAGTAACC

2701 TGAGGCTATG GCAGGGCCTG CCGCCCCGAC GTTGGCTGCG AGCCCTGGGC CTTCACCCGA

2761 ACTTGGGGGG TGGGGTGGGG AAAAGGAAGA AACGCGGGCG TATTGGCCCC AATGGGGTCT

2821 CGGTGGGGTA TCGACAGAGT GCCAGCCCTG GGACCGAACC CCGCGTTTAT GAACAAACGA

2881 CCCAACACCG TGCGTTTTAT TCTGTCTTTT TATTGCCGTC ATAGCGCGGG TTCCTTCCGG

2941 TATTGTCTCC TTCCGTGTTT CAGTTAGCCT CCCCCTAGGG TGGGCGAAGA ACTCCAGCAT

3001 GAGATCCCCG CGCTGGAGGA TCATCCAGCC GGCGTCCCGG AAAACGATTC CGAAGCCCAA

3061 CCTTTCATAG AAGGCGGCGG TGGAATCGAA ATCTCGTGAT GGCAGGTTGG GCGTCGCTTG

3121 GTCGGTCATT TCGAACCCCA GAGTCCCGCT CAGAAGAACT CGTCAAGAAG GCGATAGAAG

3181 GCGATGCGCT GCGAATCGGG AGCGGCGATA CCGTAAAGCA CGAGGAAGCG GTCAGCCCAT

3241 TCGCCGCCAA GCTCTTCAGC AATATCACGG GTAGCCAACG CTATGTCCTG ATAGCGGTCC

3301 GCCACACCCA GCCGGCCACA GTCGATGAAT CCAGAAAAGC GGCCATTTTC CACCATGATA

3361 TTCGGCAAGC AGGCATCGCC ATGGGTCACG ACGAGATCCT CGCCGTCGGG CATGCTCGCC

3421 TTGAGCCTGG CGAACAGTTC GGCTGGCGCG AGCCCCTGAT GCTCTTGATC ATCCTGATCG

3481 ACAAGACCGG CTTCCATCCG AGTACGTGCT CGCTCGATGC GATGTTTCGC TTGGTGGTCG

3541 AATGGGCAGG TAGCCGGATC AAGCGTATGC AGCCGCCGCA TTGCATCAGC CATGATGGAT

3601 ACTTTCTCGG CAGGAGCAAG GTGAGATGAC AGGAGATCCT GCCCCGGCAC TTCGCCCAAT

3661 AGCAGCCAGT CCCTTCCCGC TTCAGTGACA ACGTCGAGCA CAGCTGCGCA AGGAACGCCC

3721 GTCGTGGCCA GCCACGATAG CCGCGCTGCC TCGTCTTGCA GTTCATTCAG GCACCGGAC

3781 AGGTCGGTCT TGACAAAAAG AACCGGGCGC CCCTGCGCTG ACAGCCGGAA CACGGCGGCA

3841 TCAGAGCAGC CGATTGTCTG TTGTGCCCAG TCATAGCCGA ATAGCCTCTC CACCCAAGCG
```

```
3901 GCCGGAGAAC CTGCGTGCAA TCCATCTTGT TCAATCATGC GAAACGATCC TCATCCTGTC

3961 TCTTGATCGA TCTTTGCAAA AGCCTAGGCC TCCAAAAAAG CCTCCTCACT ACTTCTGGAA

4021 TAGCTCAGAG GCCGAGGAGG CGGCCTCGGC CTCTGCATAA ATAAAAAAAA TTAGTCAGCC

4081 ATGGGGCGGA GAATGGGCGG AACTGGGCGG AGTTAGGGGC GGGATGGGCG GAGTTAGGGG

4141 CGGGACTATG GTTGCTGACT AATTGAGATG CATGCTTTGC ATACTTCTGC CTGCTGGGGA

4201 GCCTGGGGAC TTTCCACACC TGGTTGCTGA CTAATTGAGA TGCATGCTTT GCATACTTCT

4261 GCCTGCTGGG GAGCCTGGGG ACTTTCCACA CCCTAACTGA CACACATTCC ACAGCTGGTT

4321 CTTTCCGCCT CAGGACTCTT CCTTTTTCAA TAAATCAATC TAAAGTATAT ATGAGTAAAC

4381 TTGGTCTGAC AGTTACCAAT GCTTAATCAG TGAGGCACCT ATCTCAGCGA TCTGTCTATT

4441 TCGTTCATCC ATAGTTGCCT GACTCCCCGT CGTGTAGATA ACTACGATAC GGGAGGGCTT

4501 ACCATCTGGC CCCAGTGCTG CAATGATACC GCGAGACCCA CGCTCACCGG CTCCAGATTT

4561 ATCAGCAATA AACCAGCCAG CCGGAAGGGC CGAGCGCAGA AGTGGTCCTG CAACTTTATC

4621 CGCCTCCATC CAGTCTATTA ATTGTTGCCG GGAAGCTAGA GTAAGTAGTT CGCCAGTTAA

4681 TAGTTTGCGC AACGTTGTTG CCATTGCTAC AGGCATCGTG GTGTCACGCT CGTCGTTTGG

4741 TATGGCTTCA TTCAGCTCCG GTTCCCAACG ATCAAGGCGA GTTACATGAT CCCCCATGTT

4801 GTGCAAAAAA GCGGTTAGCT CCTTCGGTCC TCCGATCGTT GTCAGAAGTA AGTTGGCCGC

4861 AGTGTTATCA CTCATGGTTA TGGCAGCACT GCATAATTCT CTTACTGTCA TGCCATCCGT

4921 AAGATGCTTT TCTGTGACTG GTGAGTACTC AACCAAGTCA TTCTGAGAAT AGTGTATGCG

4981 GCGACCGAGT TGCTCTTGCC CGGCGTCAAT ACGGGATAAT ACCGCGCCAC ATAGCAGAAC

5041 TTTAAAAGTG CTCATCATTG GAAAACGTTC TTCGGGGCGA AAACTCTCAA GGATCTTACC

5101 GCTGTTGAGA TCCAGTTCGA TGTAACCCAC TCGTGCACCC AACTGATCTT CAGCATCTTT

5161 TACTTTCACC AGCGTTTCTG GGTGAGCAAA AACAGGAAGG CAAAATGCCG CAAAAAAGGG

5221 AATAAGGGCG ACACGGAAAT GTTGAATACT CATACTCTTC CTTTTTCAAT ATTATTGAAG

5281 CATTTATCAG GGTTATTGTC TCATGAGCGG ATACATATTT GAATGTATTT AGAAAAATAA

5341 ACAAATAGGG GTTCCGCGCA CATTTCCCCG AAAAGTGCCA CCTGACGCGC CCTGTAGCGG

5401 CGCATTAAGC GCGGCGGGTG TGGTGGTTAC GCGCAGCGTG ACCGCTACAC TTGCCAGCGC

5461 CCTAGCGCCC GCTCCTTTCG CTTTCTTCCC TTCCTTTCTC GCCACGTTCG CCGGCTTTCC

5521 CCGTCAAGCT CTAAATCGGG GGCTCCCTTT AGGGTTCCGA TTTAGTGCTT TACGGCACCT

5581 CGACCCCAAA AAACTTGATT AGGGTGATGG TTCACGTAGT GGGCCATCGC CCTGATAGAC

5641 GGTTTTTCGC CCTTTGACGT TGGAGTCCAC GTTCTTTAAT AGTGGACTCT TGTTCCAAAC

5701 TGGAACAACA CTCAACCCTA TCTCGGTCTA TTCTTTTGAT TTATAAGGGA TTTTGCCGAT

5761 TTCGGCCTAT TGGTTAAAAA ATGAGCTGAT TTAACAAAAA TTTAACGCGA ATTTTAACAA

5821 AATATTAACG CTTACAATTT AC
```

Example 4: Production of B2.1A Antibody

B2.1A Antibody Chains are produced using conventional antibody expression systems incorporating the CDRs of the B2.1A as disclosed herein.

In this example the conventional expression system used is the 'antibody generation' system which is commercially available from InvivoGen at 5, rue Jean Rodier, F-31400 Toulouse, France.

```
pFUSEss-CHIg-mG1-B2.1a-vH - Example Sequence
B2.1A vH sequence cloned into pFUSEss-CHIg-Mg1 to generate a full heavy chain.
Coding sequences highlighted:
Leader sequence (vector-derived) -B2.1A vH-constant heavy (vector-derived) -STOP
                                                                (SEQ ID NO: 17)
   1 GGATCTGCGA TCGCTCCGGT GCCCGTCAGT GGGCAGAGCG CACATCGCCC ACAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCTG CTTGCTCAAC

481 TCTACGTCTT TGTTTCGTTT TCTGTTCTGC GCCGTTACAG ATCCAAGCTG TGACCGGCGC

541 CTACCTGAGA TCACCGGCGA AGGAGGGCCA CCATGTACAG GATGCAACTC CTGTCTTGCA

601 TTGCACTAAG TCTTGCACTT GTCACGAATT CGCAGGTTCA GCTGCAGGAG TCTGGGGCTG

661 AGCTGGTGAA GCCTGGGGCT TCAGTGAAGC TGTCCTGCAA GGCTTCTGGC TACACCTTCA

721 CCAACTACTG GATGCACTGG GTTAAGCAGA GGCCTGGACA AGGCCTTGAG TGGATTGGAG

781 AGATTAATCC TAGCGACGGT CATACTAACT ACAATGAGAA GTTCAAGAGC AAGGCCACAC

841 TGACTGTAGA CAAATCCTCC AGCACAGCCT ACATGCAACT CAGCAGCCTG ACATCTGAGG

901 ACTCTGCGGT CTATTACTGT GCAAGACCTT GGGCGTTTGG TAACTACGGG GCCTGGTTTG

961 CTTACTGGGG CCAAGGGACT CTGGTCACTG TCTCTGCCGC TAAAACGACA CCCCCATCTG

1021 TCTATCCACT GGCCCCTGGA TCTGCTGCCC AAACTAACTC CATGGTGACC CTGGGATGCC

1081 TGGTCAAGGG CTATTTCCCT GAGCCAGTGA CAGTGACCTG GAACTCTGGA TCCCTGTCCA

1141 GCGGTGTGCA CACCTTCCCA GCTGTCCTGC AGTCTGACCT CTACACTCTG AGCAGCTCAG

1201 TGACTGTCCC CTCCAGCACC TGGCCCAGCG AGACCGTCAC CTGCAACGTT GCCCACCCGG

1261 CCAGCAGGCA CAAGGTGGAC AAGAAAATTG TGCCCAGGGA TTGTGGTTGT AAGCCTTGCA

1321 TATGTACAGT CCCAGAAGTA TCATCTGTCT TCATCTTCCC CCCAAAGCCC AAGGATGTGC

1381 TCACCATTAC TCTGACTCCT AAGGTCACGT GTGTTGTGGT AGACATCAGC AAGGATGATC

1441 CCGAGGTCCA GTTCAGCTGG TTTGTAGATG ATGTGGAGGT GCACACAGCT CAGACGCAAC

1501 CCCGGGAGGA GCAGTTCAAC AGCACTTTCC GCTCAGTCAG TGAACTTCCC ATCATGCACC

1561 AGGACTGGCT CAATGGCAAG GAGTTCAAAT GCAGGGTCAA CAGTGCAGCT TTCCCTGCCC
```

-continued

```
1621 CCATCGAGAA AACCATCTCC AAAACCAAAG GCAGACCGAA GGCTCCACAG GTGTACACCA

1681 TTCCACCTCC CAAGGAGCAG ATGGCCAAGG ATAAAGTCAG TCTGACCTGC ATGATAACAG

1741 ACTTCTTCCC TGAAGACATT ACTGTGGAGT GGCAGTGGAA TGGGCAGCCA GCGGAGAACT

1801 ACAAGAACAC TCAGCCCATC ATGGACACAG ATGGCTCTTA CTTCGTCTAC AGCAAGCTCA

1861 ATGTGCAGAA GAGCAACTGG GAGGCAGGAA ATACTTTCAC CTGCTCTGTG TTACATGAGG

1921 GCCTGCACAA CCACCATACT GAGAAGAGCC TCTCCCACTC TCCTGGTAAA TGA TCCAGT

1981 GTCCCTAGCT GGCCAGACAT GATAAGATAC ATTGATGAGT TTGGACAAAC CACAACTAGA

2041 ATGCAGTGAA AAAATGCTT TATTTGTGAA ATTTGTGATG CTATTGCTTT ATTTGTAACC

2101 ATTATAAGCT GCAATAAACA AGTTAACAAC AACAATTGCA TTCATTTTAT GTTTCAGGTT

2161 CAGGGGGAGG TGTGGGAGGT TTTTTAAAGC AAGTAAAACC TCTACAAATG TGGTATGGAA

2221 TTAATTCTAA AATACAGCAT AGCAAAACTT AACCTCCAA ATCAAGCCTC TACTTGAATC

2281 CTTTTCTGAG GGATGAATAA GGCATAGGCA TCAGGGCTG TTGCCAATGT GCATTAGCTG

2341 TTTGCAGCCT CACCTTCTTT CATGGAGTTT AAGATATAGT GTATTTTCCC AAGGTTTGAA

2401 CTAGCTCTTC ATTTCTTTAT GTTTTAAATG CACTGACCTC CCACATTCCC TTTTTAGTAA

2461 AATATTCAGA AATAATTTAA ATACATCATT GCAATGAAAA TAAATGTTTT TTATTAGGCA

2521 GAATCCAGAT GCTCAAGGCC CTTCATAATA TCCCCCAGTT TAGTAGTTGG ACTTAGGGAA

2581 CAAAGGAACC TTTAATAGAA ATTGGACAGC AAGAAAGCGA GCTTCTAGCT TATCCTCAGT

2641 CCTGCTCCTC TGCCACAAAG TGCACGCAGT TGCCGGCCGG GTCGCGCAGG GCGAACTCCC

2701 GCCCCCACGG CTGCTCGCCG ATCTCGGTCA TGGCCGGCCC GGAGGCGTCC CGGAAGTTCG

2761 TGGACACGAC CTCCGACCAC TCGGCGTACA GCTCGTCCAG GCCGCGCACC CACACCCAGG

2821 CCAGGGTGTT GTCCGGCACC ACCTGGTCCT GGACCGCGCT GATGAACAGG GTCACGTCGT

2881 CCCGGACCAC ACCGGCGAAG TCGTCCTCCA CGAAGTCCCG GGAGAACCCG AGCCGGTCGG

2941 TCCAGAACTC GACCGCTCCG GCGACGTCGC GCGCGGTGAG CACCGGAACG GCACTGGTCA

3001 ACTTGGCCAT CATGGCTCCT Cctgtcagga gaggaaagag aagaaggtta gtacaattgC

3061 TATAGTGAGT TGTATTATAC TATGCAGATA TACTATGCCA ATGATTAATT GTCAAACTAG

3121 GGCTGCAggg ttcatagtgc acttttcct gcactgcccc atctcctgcc caccctttcc 3181 caggcataga cagtcagtga cttacCAAAC TCACAGGAGG GAGAAGGCAG AAGCTTGAGA

3241 CAGACCCGCG GGACCGCCGA ACTGCGAGGG GACGTGGCTA GGGCGGCTTC TTTTATGGTG

3301 CGCCGGCCCT CGGAGGCAGG GCGCTCGGGG AGGCCTAGCG GCCAATCTGC GGTGGCAGGA

3361 GGCGGGGCCG AAGGCCGTGC CTGACCAATC CGGAGCACAT AGGAGTCTCA GCCCCCCGCC

3421 CCAAAGCAAG GGGAAGTCAC GCGCCTGTAG CGCCAGCGTG TTGTGAAATG GGGGCTTGGG

3481 GGGGTTGGGG CCCTGACTAG TCAAAACAAA CTCCCATTGA CGTCAATGGG GTGGAGACTT

3541 GGAAATCCCG GTGAGTCAAA CCGCTATCCA CGCCCATTGA TGTACTGCCA AAACCGCATC

3601 ATCATGGTAA TAGCGATGAC TAATACGTAG ATGTACTGCC AAGTAGGAAA GTCCCATAAG

3661 GTCATGTACT GGGCATAATG CCAGGCGGGG CATTTACCGT CATTGACGTC AATAGGGGGC

3721 GTACTTGGCA TATGATACAC TTGATGTACT GCCAAGTGGG CAGTTTACCG TAAATACTCC

3781 ACCCATTGAC GTCAATGGAA AGTCCCTATT GGCGTTACTA TGGGAACATA CGTCATTATT

3841 GACGTCAATG GGCGGGGGTC GTTGGGCGGT CAGCCAGGCG GGCCATTTAC CGTAAGTTAT

3901 GTAACGCCTG CAGGTTAATT AAGAACATGT GAGCAAAAGG CCAGCAAAAG GCCAGGAACC
```

-continued

```
3961 GTAAAAAGGC CGCGTTGCTG GCGTTTTTCC ATAGGCTCCG CCCCCCTGAC GAGCATCACA

4021 AAAATCGACG CTCAAGTCAG AGGTGGCGAA ACCCGACAGG ACTATAAAGA TACCAGGCGT

4081 TTCCCCCTGG AAGCTCCCTC GTGCGCTCTC CTGTTCCGAC CCTGCCGCTT ACCGGATACC

4141 TGTCCGCCTT TCTCCCTTCG GGAAGCGTGG CGCTTTCTCA TAGCTCACGC TGTAGGTATC

4201 TCAGTTCGGT GTAGGTCGTT CGCTCCAAGC TGGGCTGTGT GCACGAACCC CCCGTTCAGC

4261 CCGACCGCTG CGCCTTATCC GGTAACTATC GTCTTGAGTC AACCCGGTA AGACACGACT

4321 TATCGCCACT GGCAGCAGCC ACTGGTAACA GGATTAGCAG AGCGAGGTAT GTAGGCGGTG

4381 CTACAGAGTT CTTGAAGTGG TGGCCTAACT ACGGCTACAC TAGAAGAACA GTATTTGGTA

4441 TCTGCGCTCT GCTGAAGCCA GTTACCTTCG GAAAAAGAGT TGGTAGCTCT TGATCCGGCA

4501 AACAAACCAC CGCTGGTAGC GGTGGTTTTT TTGTTTGCAA GCAGCAGATT ACGCGCAGAA

4561 AAAAAGGATC TCAAGAAGAT CCTTTGATCT TTTCTACGGG GTCTGACGCT CAGTGGAACG

4621 AAAACTCACG TTAAGGGATT TTGGTCATGC CTAGTTAATT AACATTTAAA TCAGCGGCCG

4681 CAATAAAATA TCTTTATTTT CATTACATCT GTGTGTTGGT TTTTTGTGTG AATCGTAACT

4741 AACATACGCT CTCCATCAAA ACAAAACGAA ACAAAACAAA CTAGCAAAAT AGGCTGTCCC

4801 CAGTGCAAGT GCAGGTGCCA GAACATTTCT CTATCGAA
``` pFUSEss-CHIg-mG1-B2.1a-vH—Preferred Sequence

B2.1A vH sequence cloned into pFUSEss-CHIg-Mg1 to generate a full heavy chain.
There is one change relative to Example Sequence (SEQ ID NO: 17) above - this
is in line 601 and is marked in bold.
Coding sequences highlighted:
Leader sequence (vector-derived)-B2.1A vH-constant heavy (vector-derived)-STOP (SEQ ID NO: 28)

```
   1 GGATCTGCGA TCGCTCCGGT GCCCGTCAGT GGGCAGAGCG CACATCGCCC ACAGTCCCCG

61 AGGAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCTG CTTGCTCAAC

481 TCTACGTCTT TGTTTCGTTT TCTGTTCTGC GCCGTTACAG ATCCAAGCTG TGACCGGCGC

541 CTACCTGAGA TCACCGGCGA AGGAGGGCCA CCATGTACAG GATGCAACTC CTGTCTTGCA

601 TTGCACTAAG TCTTGCACTT GTCACGAATT CGCAGGTTCA GCTGCAGGAG TCTGGACTG

661 AGCTGGTGAA GCCTGGGGCT TCAGTGAAGC TGTCCTGCAA GGCTTCTGGC TACACCTTCA

721 CCAACTACTG GATGCACTGG GTTAAGCAGA GGCCTGGACA AGGCCTTGAG TGGATTGGAG

781 AGATTAATCC TAGCGACGGT CATACTAACT ACAATGAGAA GTTCAAGAGC AAGGCCACAC

841 TGACTGTAGA CAAATCCTCC AGCACAGCCT ACATGCAACT CAGCAGCCTG ACATCTGAGG

901 ACTCTGCGGT CTATTACTGT GCAAGACCTT GGGCGTTTGG TAACTACGGG GCCTGGTTTG

961 CTTACTGGGGCCAAGGGACT CTGGTCACTG TCTCTGCCGC TAAAACGACA CCCCCATCIG

1021 TCTATCCACT GGCCCCTGGA TCTGCTGCCC AAACTAACTC CATGGTGACC CTGGGATGCC
```

-continued

```
1081 TGGTCAAGGG CTATTTCCCT GAGCCAGTGA CAGTGACCTG GAACTCTGGA TCCCTGTCCA

1141 GCGGTGTGCA CACCTTCCCA GCTGTCCTGC AGTCTGACCT CTACACTCTG AGCAGCTCAG

1201 TGACTGTCCC CTCCAGCACC TGGCCCAGCG AGACCGTCAC CTGCAACGTT GCCCACCCGG

1261 CCAGCAGCAC CAAGGTGGAC AAGAAAATTG TGCCCAGGGA TTGTGGTTGT AAGCCTTGCA

1321 TATGTACAGT CCCAGAAGTA TCATCTGTCT TCATCTTCCC CCCAAAGCCC AAGGATGTGC

1381 TCACCATTAC TCTGACTCCT AAGGTCACGT GTGTTGTGGT AGACATCAGC AAGGATGATC

1441 CCGAGGTCCA GTTCAGCTGG TTTGTAGATG ATGTGGAGGT GCACACAGCT CAGACGCAAC

1501 CCCGGGAGGA GCAGTTCAAC AGCACTTTCC GCTCAGTCAG TGAACTTCCC ATCATGCACC

1561 AGGACTGGCT CAATGGCAAG GAGTTCAAAT GCAGGGTCAA CAGTGCAGCT TTCCCTGCCC

1621 CCATCGAGAA AACCATCTCC AAACCAAAG GCAGACCGAA GGCTCCACAG GTGTACACCA

1681 TTCCACCTCC CAAGGAGCAG ATGGCCAAGG ATAAAGTCAG TCTGACCTGC ATGATAACAG

1741 ACTTCTTCCC TGAAGACATT ACTGTGGAGT GGCAGTGGAA TGGGCAGCCA GCGGAGAACT

1801 ACAAGAACAC TCAGCCCATC ATGGACACAG ATGGCTCTTA CTTCGTCTAC AGCAAGCTCA

1861 ATGTGCAGAA GAGCAACTGG GAGGCAGGAA ATACTTTCAC CTGCTCTGTG TTACATGAGG

1921 GCCTGCACAA CCACCATACT GAGAAGAGCC TCTCCCACTC TCCTGGTAAA TGA TCCCAGT

1981 GTCCCTAGCT GGCCAGACAT GATAAGATAC ATTGATGAGT TTGGACAAAC CACAACTAGA

2041 ATGCAGTGAA AAAATGCTT TATTTGTGAA ATTTGTGATG CTATTGCTTT ATTTGTAACC

2101 ATTATAAGCT GCAATAAACA AGTTAACAAC AACAATTGCA TTCATTTTAT GTTTCAGGTT

2161 CAGGGGGAGG TGTGGGAGGT TTTTTAAAGC AAGTAAAACC TCTACAAATG TGGTATGGAA

2221 TTAATTCTAA AATACAGCAT AGCAAAACTT TAACCTCCAA ATCAAGCCTC TACTTGAATC

2281 CTTTTCTGAG GGATGAATAA GGCATAGGCA TCAGGGGCTG TTGCCAATGT GCATTAGCTG

2341 TTTGCAGCCT CACCTTCTTT CATGGAGTTT AAGATATAGT GTATTTTCCC AAGGTTTGAA

2401 CTAGCTCTTC ATTTCTTTAT GTTTTAAATG CACTGACCTC CCACATTCCC TTTTTAGTAA

2461 AATATTCAGA AATAATTTAA ATACATCATT GCAATGAAAA TAAATGTTTT TTATTAGGCA

2521 GAATCCAGAT GCTCAAGGCC CTTCATAATA TCCCCCAGTT TAGTAGTTGG ACTTAGGGAA

2581 CAAAGGAACC TTTAATAGAA ATTGGACAGC AAGAAAGCGA GCTTCTAGCT TATCCTCAGT

2641 CCTGCTCCTC TGCCACAAAG TGCACGCAGT TGCCGGCCGG GTCGCGCAGG GCGAACTCCC

2701 GCCCCCACGG CTGCTCGCCG ATCTCGGTCA TGGCCGGCCC GGAGGCGTCC CGGAAGTTCG

2761 TGGACACGAC CTCCGACCAC TCGGCGTACA GCTCGTCCAG GCCGCGCACC CACACCCAGG

2821 CCAGGGTGTT GTCCGGCACC ACCTGGTCCT GGACCGCGCT GATGAACAGG GTCACGTCGT

2881 CCCGGACCAC ACCGGCGAAG TCGTCCTCCA CGAAGTCCCG GGAGACCCG AGCCGGTCGG

2941 TCCAGAACTC GACCGCTCCG GCGACGTCGC GCGCGGTGAG CACCGGAACG GCACTGGTCA

3001 ACTTGGCCAT GATGGCTCCT Cctgtcagga gaggaaagag aagaaggtta gtacaattgC

3061 TATAGTGAGT TGTATTATAC TATGCAGATA TACTATGCCA ATGATTAATT GTCAAACTAG

3121 GGCTGCAggg ttcatagtgc cactttttcct gcactgcccc atctcctgcc cacccttttcc 3181 caggcataga cagtcagtga cttacCAAAC TCACAGGAGG GAGAAGGCAG AAGCTTGAGA

3241 CAGACCCGCG GGACCGCCGA ACTGCGAGGG GACGTGGCTA GGGCGGCTTC TTTTATGGTG

3301 CGCCGGCCCT CGGAGGCAGG GCGCTCGGGG AGGCCTAGCG GCCAATCGC GGTGGCAGGA

3361 CCCCCCCCCC AAGGCCGTGC CTGACCAATC CGGAGCACAT AGGAGTCTCA GCCCCCCGCC
```

```
3421 CCAAAGCAAG GGGAAGTCAC GCGCCTGTAG CGCCAGCGTG TTGTGAAATG GGGGCTTGGG

3481 GGGGTTGGGG CCCTGACTAG TCAAAACAAA CTCCCATTGA CGTCAATGGG GTGGAGACTT

3541 GGAAATCCCC GTGAGTCAAA CCGCTATCCA CGCCCATTGA TGTACTGCCA AAACCGCATC

3601 ATCATGGTAA TAGCGATGAC TAATACGTAG ATGTACTGCC AAGTAGGAAA GTCCCATAAG

3661 GTCATGTACT GGGCATAATG CCAGGCGGGC CATTTACCGT CATTGACGTC AATAGGGGGC

3721 GTACTTGGCA TATGATACAC TTGATGTACT GCCAAGTGGG CAGTTTACCG TAAATACTCC

3781 ACCCATTGAC GTCAATGGAA AGTCCCTATT GGCGTTACTA TGGGAACATA CGTCATTATT

3841 GACGTCAATG GGCGGGGGTC GTTGGGCGGT CAGCCAGGCG GGCCATTTAC CGTAAGTTAT

3901 GTAACGCCTG CAGGTTAATT AAGAACATGT GAGCAAAAGG CCAGCAAAAG GCCAGGAACC

3961 GTAAAAAGGC CGCGTTGCTG GCGTTTTTCC ATAGGCTCCG CCCCCCTGAC GAGCATCACA

4021 AAAATCGACG CTCAAGTCAG AGGTGGCGAA ACCCGACAGG ACTATAAAGA TACCAGGCGT

4081 TTCCCCCTGG AAGCTCCCTC GTGCGCTCTC CTGTTCCGAC CCTGCCGCTT ACCGGATACC

4141 TGTCCGCCTT TCTCCCTTCG GGAAGCGTGG CGCTTTCTCA TAGCTCACGC TGTAGGTATC

4201 TCAGTTCGGT GTAGGTCGTT CGCTCCAAGC TGGGCTGTGT GCACGAACCC CCCGTTCAGC

4261 CCGACCGCTG CGCCTTATCC GGTAACTATC GTCTTGAGTC AACCCGGTA AGACACGACT

4321 TATCGCCACT GGCAGCAGCC ACTGGTAACA GGATTAGCAG AGCGAGGTAT GTAGGCGGTG

4381 CTACAGAGTT CTTGAAGTGG TGGCCTAACT ACGGCTACAC TAGAAGAACA GTATTTGGTA

4441 TCTGCGCTCT GCTGAAGCCA GTTACCTTGG GAAAAAGAGT TGGTAGCTCT TGATCCGGCA

4501 AACAAACCAC CGCTGGTAGC GGTGGTTTTT TTGTTTGCAA GCAGCAGATT ACGCGCAGAA

4561 AAAAGGATC TCAAGAAGAT CCTTTGATCT TTTCTACGGG GTCTGACGCT CAGTGGAACG

4621 AAAACTCACG TTAAGGGATT TTGGTCATGG CTAGTTAATT AACATTTAAA TCAGCGGCCG

4681 CAATAAAATA TCTTTATTTT CATTACATCT GTGTGTTGGT TTTTTGTGTG AATCGTAACT

4741 AACATACGCT CTCCATCAAA ACAAAACGAA ACAAACAAA CTAGCAAAAT AGGCTGTCCC

4801 CAGTGCAAGT GCAGGTGCCA GAACATTTCT CTATCGAA
``` pFUSE2ss-CLIg-mk-B2.1a-vL

B2.1A vL sequence cloned into pFUSEss-CLIg-MK to generate a full light chain.
Coding sequences highlighted:
Leader sequence (vector-derived)-B2.1A vL-constant light (vector-derived)-STOP (SEQ ID NO: 18)

```
  1 GGATCTGCGA TCGCTCCGGT GCCCGTCAGT GGGCAGAGCG CACATCGCCC AGAGTCCCCG

61 AGAAGTTGGG GGGAGGGGTC GGCAATTGAA CGGGTGCCTA GAGAAGGTGG CGCGGGGTAA

121 ACTGGGAAAG TGATGTCGTG TACTGGCTCC GCCTTTTTCC CGAGGGTGGG GGAGAACCGT

181 ATATAAGTGC AGTAGTCGCC GTGAACGTTC TTTTTCGCAA CGGGTTTGCC GCCAGAACAC

241 AGCTGAAGCT TCGAGGGGCT CGCATCTCTC CTTCACGCGC CCGCCGCCCT ACCTGAGGCC

301 GCCATCCACG CCGGTTGAGT CGCGTTCTGC CGCCTCCCGC CTGTGGTGCC TCCTGAACTG

361 CGTCCGCCGT CTAGGTAAGT TTAAAGCTCA GGTCGAGACC GGGCCTTTGT CCGGCGCTCC

421 CTTGGAGCCT ACCTAGACTC AGCCGGCTCT CCACGCTTTG CCTGACCCTG CTTGCTCAAC

481 TCTACGTCTT TGTTTCGTTT TCTGTTCTGC GCCGTTACAG ATCCAAGCTG TGACCGGCGC

541 CTACCTGAGA TCAACATGTA CAGGATGCAA CTCCTGTCTT GCATTGCACT AAGTCTTGCA

601 CTTGTCACGA ATTCAGATAT AGTGATGACC CAGTCTCCAA AATTCATGTC CACATCAGTA
```

```
 661 GGAGACAGGG TCAGCATCAC CTGCAAGGCC AGTCAGAATG TTCGTACTGC TGTAGCCTGG

721 TATCAACAGA AACCAGGGCA GTCTCCTAAA GCACTGATTT ACTTGGCATC CAGCCGGCAC

781 ACTGGAGTCC CTGATCGCTT CACAGGCAGT GGATCTGGGA CAGATTTCAC TCTCACCATT

841 AGCAATGTGC AATCTGAAGA CCTGGCAGAT TATTTCTGTC TGCAACATTG GAATTATCCG

901 TACACGTTCG GAGGGGGGAC CAAGCTCGAG ATCAAACGGG CAGATGCTGC ACCAACTGTA

961 TCCATCTTCC CACCATCCAG TGAGCAGTTA ACATCTGGAG GTGCCTCAGT CGTGTGCTTC

1021 TTGAACAACT TCTACCCCAA AGACATCAAT GTCAAGTGGA AGATTGATGG CAGTGAACGA

1081 CAAAATGGCG TCCTGAACAG TTGGACTGAT CAGGACAGCA AGACAGCAC CTACAGCATG

1141 AGCAGCACCC TCACGTTGAC CAAGGACGAG TATGAACGAC ATAACAGCTA TACCTGTGAG

1201 GCCACTCACA AGACATCAAC TTCACCCATT GTCAAGAGCT TCAACAGGAA TGAGTGTTAG

1261 AGACAAAGGT CCTGAGAGCT AGCTGGCCAG ACATGATAAG ATACATTGAT GAGTTTGGAC

1321 AAACCACAAC TAGAATGCAG TGAAAAAAAT GCTTTATTTG TGAAATTTGT GATGCTATTG

1381 CTTTATTTGT AACCATTATA AGCTGCAATA ACAAGTTAA CAACAACAAT TGCATTCATT

1441 TTATGTTTCA GGTTCAGGGG GAGGTGTGGG AGGTTTTTTA AAGCAAGTAA AACCTCTACA

1501 AATGTGGTAT GGAATTAATT CTAAAATACA GCATAGCAAA ACTTTAACCT CCAAATCAAG

1561 CCTCTACTTG AATCCTTTTC TGAGGGATGA ATAAGGCATA GGCATCAGGG GCTGTTGCCA

1621 ATGTGCATTA GCTGTTTGCA GCCTCACCTT CTTTCATGGA GTTTAAGATA TAGTGTATTT

1681 TCCCAAGGTT TGAACTAGCT CTTCATTTCT TTATGTTTTA AATGCACTGA CCTCCCACAT

1741 TCCCTTTTTA GTAAAATATT CAGAAATAAT TTAAATACAT CATTGCAATG AAAATAAATG

1801 TTTTTTATTA GGCAGAATCC AGATGCTCAA GGCCCTTCAT AATATCCCCC AGTTTAGTAG

1861 TTGGACTTAG GGAACAAAGG AACCTTTAAT AGAAATTGGA CAGCAAGAAA GCGAGCTTCT

1921 AGCTTTAGTT CCTGGTGTAC TTGAGGGGGA TGAGTTCCTC AATGGTGGTT TTGACCAGCT

1981 TGCCATTCAT CTCAATGAGC ACAAAGCAGT CAGGAGCATA GTCAGAGATG AGCTCTCTGC

2041 ACATGCCACA GGGGCTGACC ACCCTGATGG ATCTGTCCAC CTCATCAGAG TAGGGGTGCC

2101 TGACAGCCAC AATGGTGTCA AGTCCTTCT GCCCGTTGCT CACAGCAGAC CCAATGGCAA

2161 TGGCTTCAGC ACAGACAGTG ACCCTGCCAA TGTAGGCCTC AATGTGGACA GCAGAGATGA

2221 TCTCCCCAGT CTTGGTCCTG ATGGCCGCCC CGACATGGTG CTTGTTGTCC TCATAGAGCA

2281 TGGTGATCTT CTCAGTGGCG ACCTCCACCA GCTCCAGATC CTGCTGAGAG ATGTTGAAGG

2341 TCTTCATGAT GGCTCCTCct gtcaggagag gaaagagaag aaggttagta caattgCTAT

2401 AGTGAGTTGT ATTATACTAT GCTTATGATT AATTGTCAAA CTAGGGCTGC Agggttcata 2461 gtgccacttt tcctgcactg ccccatctcc tgcccaccct ttcccaggca tagacagtca 2521 gtgacttacC AAACTCACAG GAGGGAGAAG GCAGAAGCTT GAGACAGACC CGCGGGACCG

2581 CCGAACTGCG AGGGGACGTG GCTAGGGCGG CTTCTTTTAT GGTGCGCCGG CCCTCGGAGG

2641 CAGGGCGCTC GGGGAGGCCT AGCGGCCAAT CTGCGGTGGC AGGAGGCGGG GCCGAAGGCC

2701 GTGCCTGACC AATCCGGAGC ACATAGGAGT CTCAGCCCCC CGCCCAAAG CAAGGGGAAG

2761 TCACGCGCCT GTAGCGCCAG CGTGTTGTGA ATGGGGGCT TGGGGGGGTT GGGGCCCTGA

2821 CTAGTCAAAA CAAACTCCCA TTGACGTCAA TGGGGTGGAG ACTTGGAAAT CCCCGTGAGT

2881 CAAACCGCTA TCCACGCCCA TTGATGTACT GCCAAAACCG CATCATCATG GTAATAGCGA

2941 TGACTAATAC GTAGATGTAC TGCCAAGTAG GAAAGTCCCA TAAGGTCATG TACTGGGCAT
```

```
-continued
3001 AATGCCAGGC GGGCCATTTA CCGTCATTGA CGTCAATAGG GGGCGTACTT GGCATATGAT

3061 ACACTTGATG TACTGCCAAG TGGGCAGTTT ACCGTAAATA CTCCACCCAT TGACGTCAAT

3121 GGAAAGTCCC TATTGGCGTT ACTATGGGAA CATACGTCAT TATTGACGTC AATGGGCGGG

3181 GGTCGTTGGG CGGTCAGCCA GGCGGGCCAT TTACCGTAAG TTATGTAACG CCTGCAGGTT

3241 AATTAAGAAC ATGTGAGCAA AAGGCCAGCA AAAGGCCAGG AACCGTAAAA AGGCCGCGTT

3301 GCTGGCGTTT TTCCATAGGC TCCGCCCCCC TGACGAGCAT CACAAAAATC GACGCTCAAG

3361 TCAGAGGTGG CGAAACCCGA CAGGACTATA AAGATACCAG GCGTTTCCCC CTGGAAGCTC

3421 CCTCGTGCGC TCTCCTGTTC CGACCCTGCC GCTTACCGGA TACCTGTCCG CCTTTCTCCC

3481 TTCGGGAAGC GTGGCGCTTT CTCATAGCTC ACGCTGTAGG TATCTCAGTT CGGTGTAGGT

3541 CGTTCGCTCC AAGCTGGGCT GTGTGCACGA ACCCCCCGTT CAGCCCGACC GCTGCGCCTT

3601 ATCCGGTAAC TATCGTCTTG AGTCCAACCC GGTAAGACAC GACTTATCGC CACTGGCAGC

3661 AGCCACTGGT AACAGGATTA GCAGAGCGAG GTATGTAGGC GGTGCTACAG AGTTCTTGAA

3721 GTGGTGGCCT AACTACGGCT ACACTAGAAG AACAGTATTT GGTATCTGCG CTCTGCTGAA

3781 GCCAGTTACC TTCGGAAAAA GAGTTGGTAG CTCTTGATCC GGCAAACAAA CCACCGCTGG

3841 TAGCGGTGGT TTTTTTGTTT GCAAGCAGCA GATTACGCGC AGAAAAAAAG GATCTCAAGA

3901 AGATCCTTTG ATCTTTTCTA CGGGGTCTGA CGCTCAGTGG AACGAAAACT CACGTTAAGG

3961 GATTTTGGTC ATGGCTAGTT AATTAACATT TAAATCAGCG GCCGCAATAA AATATCTTTA

4021 TTTTCATTAC ATCTGTGTGT TGGTTTTTTG TGTGAATCGT AACTAACATA CGCTCTCCAT

4081 CAAAACAAAA CGAAACAAAA CAAACTAGCA AAATAGGCTG TCCCCAGTGC AAGTGCAGGT

4141 GCCAGAACAT TTCTCTATCG AA
```

Example 5: Challenge Studies in Mice

Mouse Model

We use the immunocompetent mouse model developed by Dorner et al (Dorner et al 2011 Hepatology Vol 54 No 5 pages 1873-1875; Dorner et al 2011 Nature Vol 474 pages 208-211; Dorner et al 2013 Methods Vol 59 pages 249-257; Zeisel et al 2011). This is the most appropriate model for testing HCV vaccines.

Commercially available transgenic Gt(ROSA)26Sortml (Luc)Kaelin mice (Rosa26-Fluc) contain a LoxP-flanked STOP cassette restricting firefly luciferase expression. They are made permissive for HCV entry by infection with adenoviruses encoding essential cell surface receptors (human CD81, occludin, claudin 1 and SR-BI), and then infected with recombinant bicistronic HCVcc expressing cyclization recombination (CRE) recombinase. Upon HCV entry into mouse hepatocytes, the recombinant viral genome is translated and the CRE protein is expressed. The CRE recombinase excises the STOP cassette and activates the luciferase reporter, leading to bioluminescence that can be measured using a using a whole body bioluminescence imager.

Experimental Details
1. Establish a small colony (~30) of the commercially-available transgenic (Rosa26-Fluc CRE reporter mice.
2. Carry out a small-scale vaccination (6-8 animals) with B2.1A Fab-KLH and check the anti-E2 serum titre after each vaccination by ELISA. (Primary vaccination with immunogen in Freund's Complete Adjuvant, followed by 5 boosts with immunogen in Freund's Incomplete Adjuvant).
3. If adequate anti-E2 serum titres are obtained, vaccinate a larger number (24) as above.
4. Genetically humanise the immunised mice by administering adenovirus vectors encoding human CD81 and OCLN, and human or murine SR-BI and CLDN1.
5. After 24 hours administer $2\times10^7$ TCID50 of HCV-CRE. Use 4 different HCV viruses representing a range of genotypes.
6. After 72 hours measure bioluminescence using a whole body imager, and correlate anti-E2 titre with HCV infection. An inverse correlation indicates that the vaccine protects against HCV challenge

Example 6: B2.1A Structure

A Fab fragment of AP33 was co-crystallised in complex with a single-chain variable fragment (scFv) of B2.1A, and the structure determined to a resolution of 1.8 Å, which unambiguously shows the positions of all the amino acid side-chains and of water molecules at the interface between the two antibodies. The asymmetric unit of this $Ab_1$-$Ab_2$ complex was composed of one molecule of AP33 Fab and one molecule of B2.1A scFv. The structural coordinates were determined.

Figure 13:
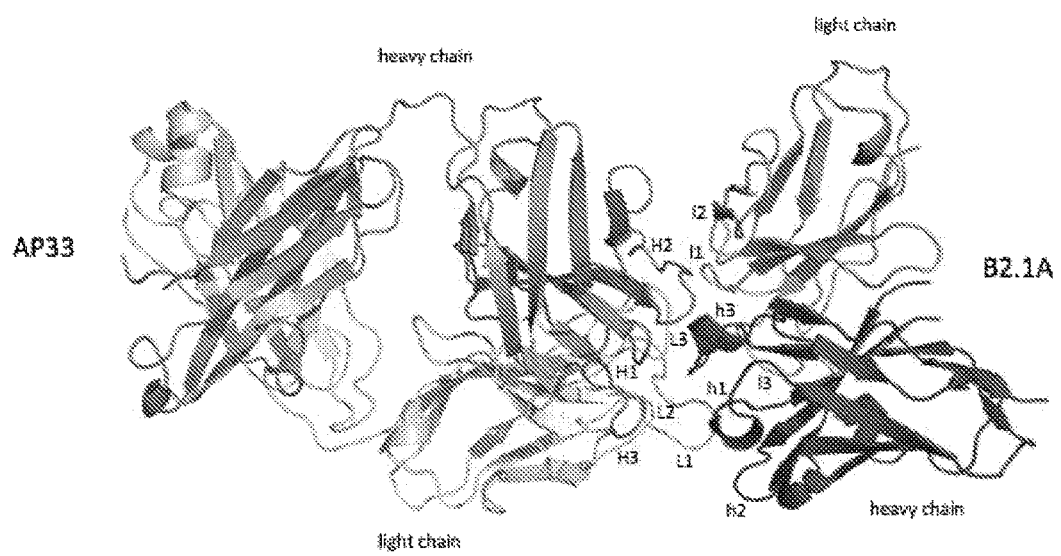
FIG. 13 shows a ribbon diagram.

The structure (FIG. 13) shows that the CDR loops of B2.1A correspond more closely to the definition of IgG regions described by Chothia et al. than by Kabat et al.

The combining site of B2.1A has an overall concave surface from which the CDR-L1 and CDR-H3 loops protrude outwards, towards the groove formed between the CDR-L2, CDR-L3 and CDR-H3 loops of AP33. The groove on AP33 has an overall negative charge, while the L1 loop on B2.1A has a complementary positive charge. Overall, both combining sites have a hydrophobic nature, due to the presence of numerous aromatic residues. All the heavy and light chain CDRs of B2.1A are involved in interactions with AP33 via hydrogen bonds and other hydrophilic interactions, hydrophobic interactions and van der Waals contacts. The area of the interface is 1069 Å, which is approximately 9% of the total surface of the B2.1a scFv.

Example 7: Antigen Mimicry by B2.1A

Figure 14:
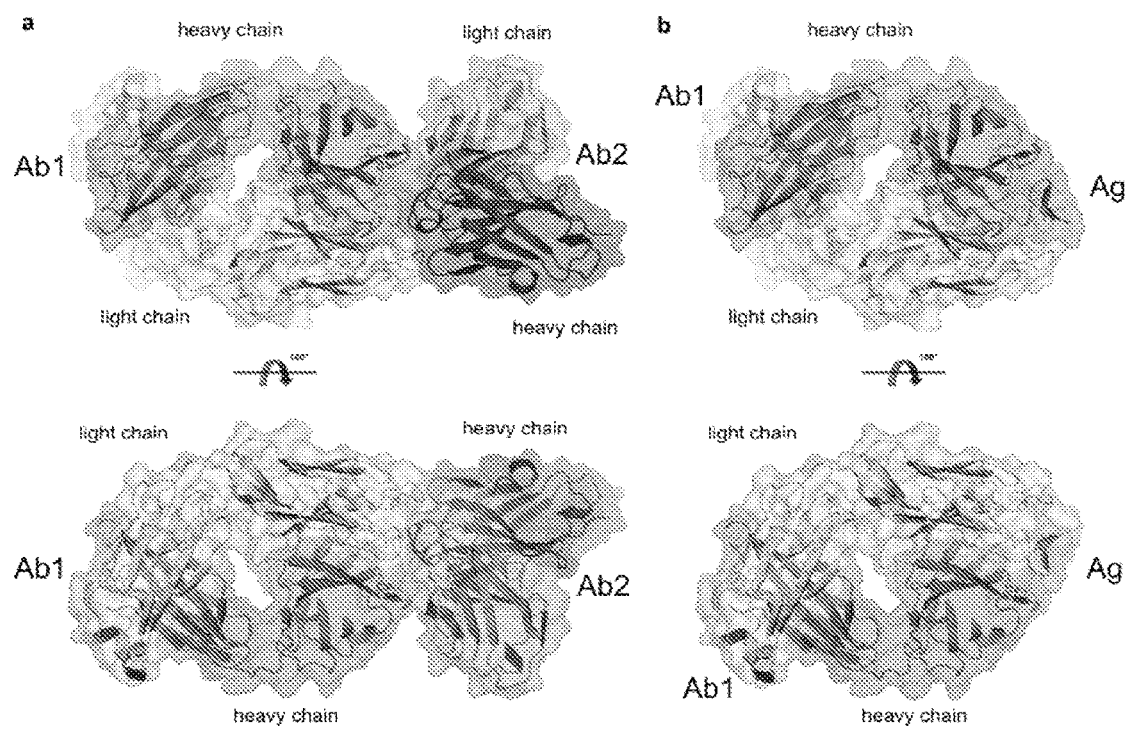
FIG. 14 shows that B2.1A docks into the AP33 antigen-binding site. Ribbon and surface representation of AP33 Fab (Ab1; heavy chain: orange, light chain: yellow) in complex with (a) B2.1A scFv (Ab2; heavy chain: purple, light chain: pink), and (b) a peptide corresponding to the HCV E2 epitope (Ag; teal; pdb accession code 4gag).
Figure 15:
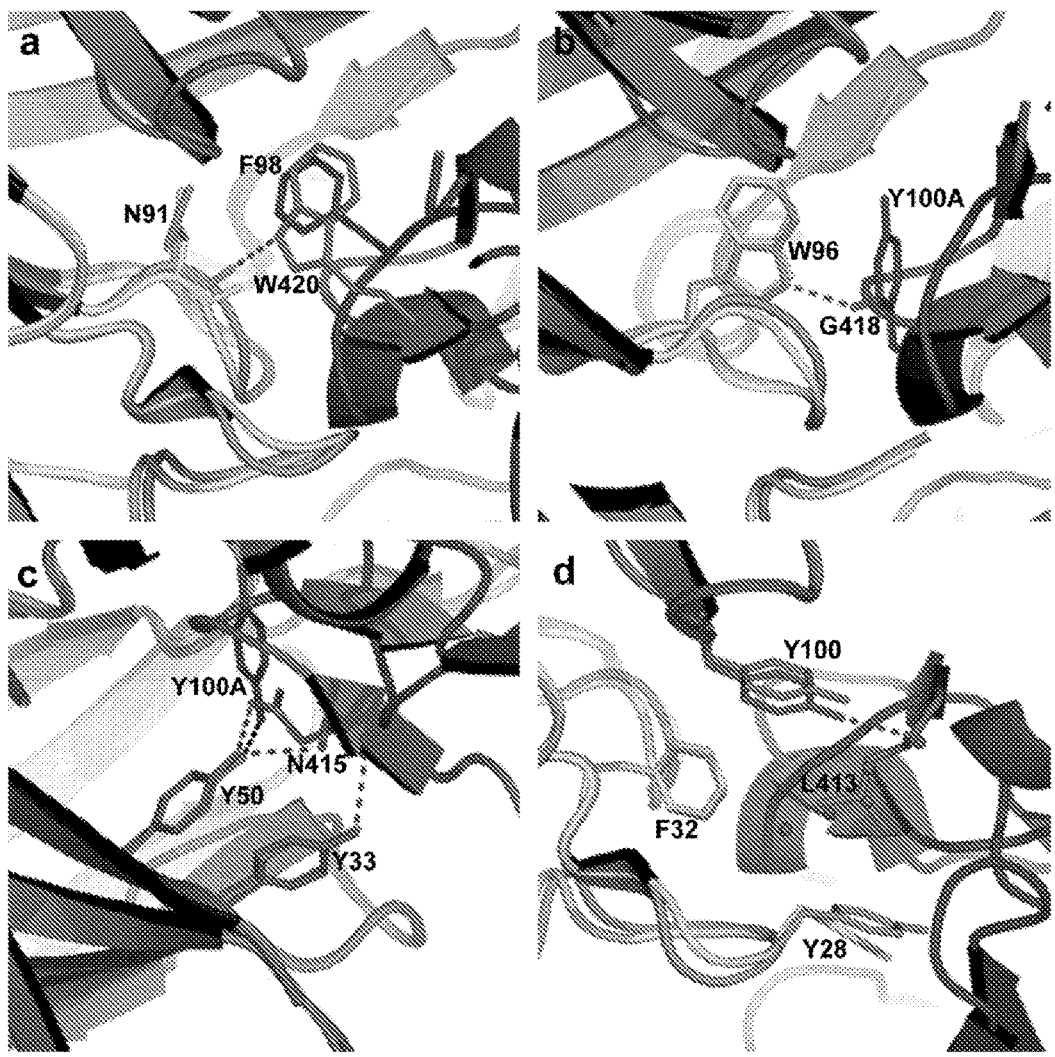
FIG. 15 shows Antigen mimicry by B2.1A. Structural alignment of the Ab$_1$-Ab$_2$ complex (AP33 heavy chain: orange, light chain: yellow; B2.1A heavy chain: purple, light chain: pink) with the Ab$_1$-Ag complex (AP33 heavy chain: blue, light chain: teal; peptide: magenta; pdb accession code 4gag). Hydrogen bonds in the Ab$_1$-Ab$_2$ complex are shown as black dashed lines and TABLE A-continued A summary of the Ab2 data obtained
from December 2008 to October 2011

A comparison of this $Ab_1$-$Ab_2$ complex with the $Ab_1$-Ag complex (i.e. the structure of AP33 in complex with a peptide corresponding to its E2 epitope (Potter et al. 2012; pdb accession code 4gag)) shows that B2.1A docks into the AP33 antigen-binding site (FIG. 14). It reveals that CDR-H3 of B2.1A mimics the shape and character of the E2 epitope, even though there is no sequence similarity. The critical E2 residue W420, which is deeply buried in the $Ab_1$-Ag complex, is mimicked by $F_H98$ of B2.1A in the $Ab_1$-$Ab_2$ complex (FIG. 15a).

The other important E2 residues at the $Ab_1$-Ag interface are G418, N415 and L413. The shape of the antigen around G418 is preserved by the side chain of B2.1A $Y_H100A$, which forms extensive contacts with $W_L96$ of AP33 (FIG. 15b). The polar character of E2 residue N415, which is deeply buried in the $Ab_1$-Ag complex, is conferred by $N_H100$ of B2.1A, while the neighbouring $Y_H100A$ provides a hydrogen bond to $Y_H50$ of AP33 (FIG. 15c). Interestingly, the interactions of L413 with AP33 are mimicked not by an amino acid residue but by five water molecules in the $Ab_1$-$Ab_2$ complex (FIG. 15d). In keeping with our biochemical and immunisation data (shown in Table 1 and FIGS. 9-12), this structural analysis confirms that B2.1A is an $Ab_2\beta$, i.e. an anti-idiotypic antibody that fits into the antigen-binding site (paratope) of the $Ab_1$ precisely enough to be an "internal image" of it, and, by the same token, an effective mimic of the original antigen.

Example 8: B2.1A Binding Affinity

We measured the binding affinity of B2.1A for AP33 by Surface Plasmon Resonance (SPR). B2.1A scFv was immobilised in three different ways: (a) amine coupling to a CM5 chip; (b) amine coupling to a CM4 chip; (c) capture via a histidine tag to a NTA chip. AP33 was then injected over the surface, using single-cycle kinetics. All the data sets were high quality and the three experiments yielded affinity constants of 29 nm, 20 nm and 8 nm, respectively:

TABLE

| Binding affinity of B2.1A for AP33 | | | |
| --- | --- | --- | --- |
| Expt | Ka (1/Ms) | Kd (1/s) | KD (M) |
| a) | $1.12 * 10^4$ | $3.21 * 10^{-4}$ | $2.86 * 10^{-8}$ |
| b) | $1.18 * 10^4$ | $2.43 * 10^{-4}$ | $2.07 * 10^{-8}$ |
| c) | $4.87 * 10^4$ | $3.9 * 10^{-4}$ | $8.0 * 10^{-9}$ |

These values are comparable to the affinity constants of 5.5-6.6 nm, measured by SPR, for binding of antibody MRCT10 (humanised AP33-WO2009/081285) to soluble $E2_{661}$ (Pantua et al 2013).

Example 9: B2.1A Mutagenesis

Figure 16:
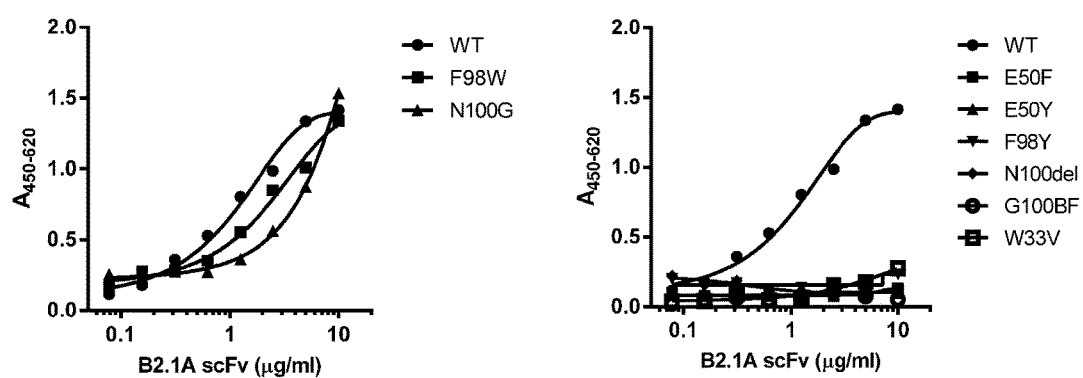
Figure 17:
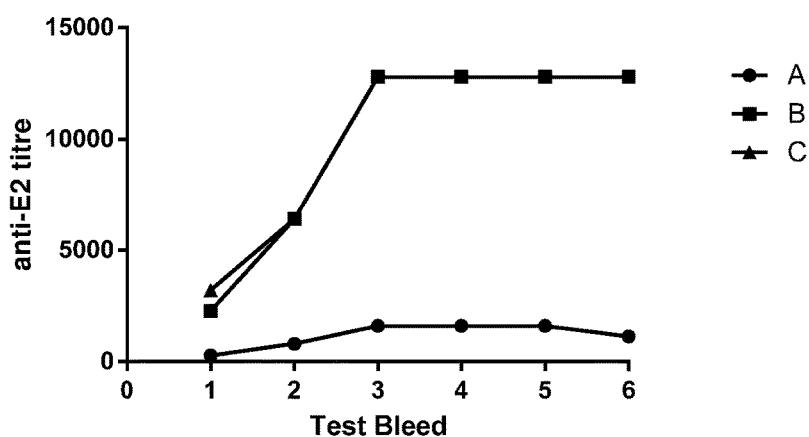
Figure 18:
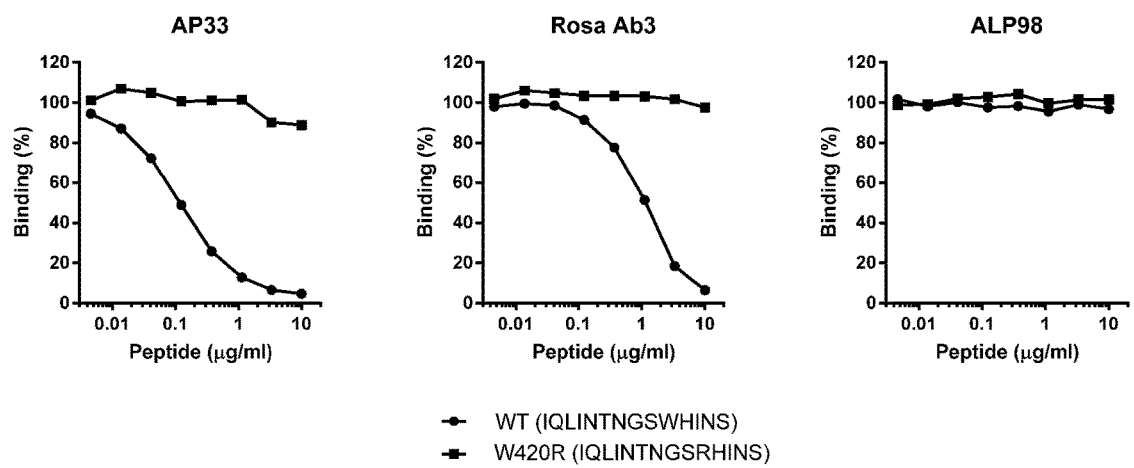

The crystallographic structure of B2.1A scFv, together with protein-protein interaction prediction servers, inspired the inventors to design point mutations aimed at increasing its binding affinity for AP33. The inventors reasoned that this might translate into an increased affinity for HCV E2 of Ab3 antibodies elicited by vaccination with B2.1A. The following mutations were introduced into the heavy chain sequence of B2.1A: W33V, E50F, E50Y, F98Y, F98W, N100G, N100del and G100BF, in a wild-type (WT) protein comprising a fusion of B2.1A scFv with maltose binding protein (MBP). The affinity of the mutant proteins for AP33 was assessed by AP33-capture ELISA, using MBP as a detection tag. As shown in FIG. 16b, most of the mutants showed little or no binding to AP33. Only two of the mutants, F98W and N100G, retained binding, but it was weaker than WT (FIG. 16a).

The $EC_{50}$ values, estimated by fitting a sigmoidal curve to the data, were 1.48 μg/ml for WT and 4.6 μg/ml for F98W.

Thus it seems that it is not possible to improve the affinity of B2.1A for AP33 by mutagenesis.

These results demonstrate that AP33 appears to represent the best possible antibody and additionally show that it is demonstrably superior to rationally designed alternatives and therefore possesses significant technical advantages over other antibody species having different amino acid sequences.

Example 10: Vaccination with B2.1A/Protection from HCV Infection

The immunocompetent mouse model developed by Marcus Dorner (Dorner et al 2011; Dorner et al 2013) is used to test whether vaccination with B2.1A can protect against infection by HCV. This is the most appropriate model for testing HCV vaccines. Commercially available transgenic Rosa26-Fluc mice contain a LoxP-flanked STOP cassette restricting firefly luciferase expression. They are made permissive for HCV entry by infection with adenoviruses encoding essential cell-surface receptors (human CD81, occludin, claudin 1 and SR-BI), and then infected with recombinant bicistronic HCVcc expressing cyclisation recombination (CRE) recombinase. Upon HCV entry into mouse hepatocytes, the recombinant viral genome is translated and the CRE protein is expressed. The CRE recombinase excises the STOP cassette and activates the luciferase reporter, leading to bioluminescence that can be measured using a using a whole body bioluminescence imager.

Detailed Protocols of Immunisation & Challenge Experiments in Mice

Mice Strain FVB.129S6(B6)-Gt(ROSA) 26Sor$^{tm1(Luc)Kael}$/J, (abbreviate to Rosa26-Fluc; Jackson Laboratories stock no 005125). Purchase 2-3 mating pairs and breed the mice to obtain sufficient numbers for immunisation.

Immunisation Protocol 1

Immunogens: (A) B2.1A Fab conjugated to KLH, 1 mg/ml (B) Peptide IQLINTNGSWHINS conjugated to KLH, 1 mg/ml (The peptide corresponds to the AP33 epitope, ie aa 412-423 of HCV E2)

For primary vaccination make up a 1:1 emulsion of immunogen (A) with Freund's Complete Adjuvant (FCA). The final protein concentration is 0.5 mg/ml.

For all booster vaccinations make up a 1:1 emulsion of immunogen (A) or (B), as appropriate, with Freund's Incomplete Adjuvant (IFA).

Day 0 Pre-immune bleed.

Day 7 Primary vaccination. Subcutaneous injection of 50 μg in 100 μl per mouse of immunogen (A) in CFA Day 28 Booster 1. Subcutaneous injection of 50 µg in 100 µl per mouse of immunogen (A) in IFA.
Day 35 Test bleed 1.
Day 42 Booster 2. Subcutaneous injection of 50 µg in 100 µl per mouse of immunogen (B) in IFA.
Day 49 Test bleed 2.
Day 56 Booster 3. Subcutaneous injection of 50 µg in 100 µl per mouse of immunogen (A) in IFA.
Day 63 Test bleed 3.
Day 70 Booster 4. Subcutaneous injection of 50 µg in h100 µl per mouse of immunogen (B) in IFA.
Day 77 Test bleed 4.
Day 84 Booster 5. Subcutaneous injection of 50 µg in 100 µl per mouse of immunogen (A) in IFA.
Day 91 Test bleed 5.

The timing does not have to be exactly as above. The first boost should be at least three weeks after the primary immunisation, and the subsequent boosters should be at least two weeks apart. A test bleed should be taken 7-10 days after the booster.

Immunisation Protocol 2

Immunogen: B2.1A Fab conjugated to KLH, 1 mg/ml

For primary vaccination make up a 1:1 emulsion of immunogen with Freund's Complete Adjuvant (FCA). The final protein concentration is 0.5 mg/ml.

For all booster vaccinations make up a 1:1 emulsion of immunogen with Freund's Incomplete Adjuvant (IFA).

Day 0 Pre-immune bleed.
Day 7 Primary vaccination. Subcutaneous injection of 50 µg in 100 µl per mouse of immunogen in CFA
Day 28 Booster 1. Subcutaneous injection of 50 µg in 100 µl per mouse of immunogen in IFA.
Day 35 Test bleed 1.
Day 42 Booster 2. Subcutaneous injection of 50 µg in 100 µl per mouse of immunogen in IFA.
Day 49 Test bleed 2.
Day 56 Booster 3. Subcutaneous injection of 50 µg in 100 µl per mouse of immunogen in IFA.
Day 63 Test bleed 3.
Day 70 Booster 4. Subcutaneous injection of 50 µg in 100 µl per mouse of immunogen in IFA.
Day 77 Test bleed 4.
Day 84 Booster 5. Subcutaneous injection of 50 µg in 100 µl per mouse of immunogen in IFA.
Day 91 Test bleed 5.

The timing does not have to be exactly as above. The first boost should be at least three weeks after the primary immunisation, and the subsequent boosters should be at least two weeks apart. A test bleed should be taken 7-10 days after the booster.

If the test bleeds show that the mice have developed HCV E2-specific antibodies, proceed with genetic humanisation and challenge according the protocol below. If the test bleeds show that the mice have developed a high titre (>1:10,000) of HCV E2-specific antibodies after two or three boosters, there is no need to give all the boosters.

We have described two immunisation protocols. The first protocol includes boosters with a peptide corresponding to the E2 epitope that is mimicked by the CDRs of B2.1A. This aims to focus the immune response on the desired region of B2.1A. The second protocol boosts with B2.1A Fab alone. Our data show that we can definitely elicit E2-specific antibodies using B2.1A Fab alone. Boosting with peptide may or may not confer an advantage. The skilled worker may choose the protocol according to their needs.

Test bleeds are processed as is known in the art, i.e. by taking the test bleed, clotting it, taking the supernatant, centrifuging it to pellet any cells not removed with the clot, adding 1 mM sodium azide and storing it at 4 degrees Celsius until needed.

Titration[1] of mouse serum by sE2 by ELISA

[1] The titre of a serum is defined as the lowest concentration that gives a positive antigen-specific signal. In this assay, a positive signal is defined as an $A_{450}$ reading that is three times higher than that produced by non-immune, control serum at the same dilution. The mean signal from several non-immune sera is used as the control.

1. Coat the wells of a 96-well Immulon 2 HB plate with 0.2 μg/well of purified soluble HCV E2[2] in 100 ul PBS. Incubate overnight at RT.

[2] soluble E2 (sE2) expressed and purified from insect cells. It comprises aa 384-661 of the HCV polyprotein, ie the ectodomain without the membrane-proximal and trans-membrane regions.

2. Discard sE2 and block with 2% skimmed milk powder in PBST[3], 200 μl/well. Incubate for 2 hours at RT.

[3] PBST=PBS+0.05% Tween 20

3. Wash 3× with PBST. The plate can be stored at this stage at −20° C. or 4° C.
4. Add two-fold dilutions of serum in 100 μl of PBST. Incubate for 2 hours at RT.
5. Wash 3× with PBST.
6. Add 100 μl/well of anti-mouse HRP conjugate (Sigma A4416) diluted 1/3000 in PBST. Incubate for 1 hour at RT.
7. Wash 4×PBST.
8. Add 100 μl/well of TMB substrate. Incubate at RT for 30 mins.
9. Stop the reaction by adding 50 μl/well of 0.5M $H_2SO_4$.
10. Read the absorbance at 450 nm in a microplate reader.

Infection of Genetically Humanised Rosa26-Fluc Mice with HCV-CRE

The preparation of adenoviruses and recombinant HCV-CRE and the analysis of HCV entry by in vivo bioluminescence imaging are carried out exactly as known in the art, for example as described in sections 2.2.1, 2.2.2 and 2.3.2 of Dorner et al, 2013 which is incorporated herein by reference specifically for the detailed description of performing this technique.

In this example we show data for six mice. Three mice were given a primary vaccination with B2.1A Fab coupled to KLH, followed by five booster vaccinations. This elicited robust anti-E2 titres of 1:12,800 in two mice and 1:1,600 in the third mouse (FIG. 17).

The E2 reactivity is inhibited by a peptide containing the AP33 epitope, showing that the Ab3 antibodies elicited in the Rosa26-Fluc mice have the same specificity as AP33 (FIG. 18). This shows that the binding to E2 of AP33 and of Ab3 in the Rosa26 Flue immune sera is specifically inhibited in a concentration-dependent manner by the WT peptide that contains the AP33 epitope. There is no inhibition by the peptide in which W420, an essential contact residue for AP33, has been replaced by R. As expected, ALP98, which binds to a different linear epitope on E2 (aa residues 644-651), is not inhibited by either of the peptides.

Thus the Rosa26Fluc mice showed a good immune response.

The vaccinated and unvaccinated mice are made permissive for HCV infection as described above, and then challenged with $2\times10^7$ $TCID_{50}$ of HCV-CRE.

REFERENCES TO EXAMPLES

1. Chothia, C., A. M. Lesk, A. Tramontano, M. Levitt, S. J. Smith-Gill, G. Air, S. Sheriff, E. A. Padlan, D.

Davies, W. R. Tulip et al. (1989). Conformations of immunoglobulin hypervariable regions. *Nature* 342, 877--883.

2. Dorner, M., Horwitz, J. A., Robbins, J. B., Barry, W. T., Feng, Q., Mu, K., Jones, C. T., Schoggins, J. W., Catanese, M. T., Burton, D. R., Law, M., Rice, C. M. & Ploss, A. (2011). A genetically humanized mouse model for hepatitis C virus infection. *Nature* 474, 208-211.

3. Dorner, M., Rice, C. M. & Ploss, A. (2013). Study of hepatitis C virus entry in genetically humanized mice. *Methods* 59, 249-257.

4. Kabat, E. A., T. T. Wu, H. M. Perry, K. S. Gottesman, and C. Foeller. (1991). Sequences of proteins of immunological interest. 5$^{th}$ Edition ed. U.S. Department of Health and Human Services/NIH, Bethesda, Md.

5. Potter, J. A., Owsianka, A. M., Jeffery, N., Matthews, D, J, Keck, Z.-Y., Lau, P. L., Foung, S. K. H., Taylor, G. L. & Patel, A. H. (2012). Towards a hepatitis C virus vaccine: the structural basis of hepatitis C virus neutralization by AP33, a broadly neutralizing antibody. *J. Virol.* 86, 12923-12932.

6. Pantua, H., Diao, J., Ultsch, M., Hazen, M., Mathieu, M., McCutcheon, K., Takeda, K., Date, S., Cheung, T. K., Phung, Q., Hass, P., Arnott, D., Hongo, J-A., Matthews, D. J., Brown, A., Patel, A. H., Kelley, R. F., Eigenbrot, C. and Kapadia, S. B. (2013). Glycan shifting on hepatitis C virus (HCV) E2 glycoprotein is a mechanism for escape from broadly neutralizing antibodies. *J. Mol. Biol.* 425, 1899-1914.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention claimed is:

1. An anti-idiotypic antibody or antigen binding fragment thereof said anti-idiotypic antibody or antigen binding fragment thereof comprising VL CDR1 (L1), VL CDR2 (L2), and VL CDR3 (L3) consisting of the amino acid sequences of SEQ ID NO:1, SEQ ID NO:2 and SEQ ID NO:23 respectively, and VH CDR1 (H1), VH CDR2 (H2), and VH CDR3 (H3) consisting of the amino acid sequences of SEQ ID NO:24, SEQ ID NO:25, and SEQ ID NO:26 respectively, wherein said anti-idiotypic antibody or antigen binding fragment thereof specifically binds to an antigen binding pocket of an AP33 antibody.

2. The anti-idiotypic antibody or antigen binding fragment thereof according to claim 1 wherein said anti-idiotypic antibody or antigen binding fragment thereof comprises VL amino acid sequence consisting of the amino acid sequence of SEQ ID NO:20.

3. The anti-idiotypic antibody or antigen binding fragment thereof according to claim 1 wherein said anti-idiotypic antibody or antigen binding fragment thereof comprises VH amino acid sequence consisting of the amino acid sequence of SEQ ID NO:22.

4. The anti-idiotypic antibody or antigen binding fragment thereof according to claim 1 wherein said anti-idiotypic antibody or antigen binding fragment thereof comprises VL amino acid sequence consisting of the amino acid sequence of SEQ ID NO:20 and wherein said anti-idiotypic antibody or antigen binding fragment thereof comprises VH amino acid sequence consisting of the amino acid sequence of SEQ ID NO:22.

5. The anti-idiotypic antibody or antigen binding fragment thereof according to claim 1, wherein the antigen binding fragment thereof is selected from the group consisting of a Fab fragment, a Fab' fragment, a F(ab')2 fragment, a scFv, a Fv, a rIgG, and a diabody.

6. The anti-idiotypic antibody or antigen binding fragment thereof according to claim 5 wherein said antigen binding fragment is a scFv and wherein said scFv comprises the amino acid sequence of SEQ ID NO:11 or SEQ ID NO:12 or SEQ ID NO:13.

7. A nucleic acid comprising a nucleotide sequence encoding a variable heavy chain domain, a variable light chain domain, or both the variable heavy chain domain and the variable light chain domain of an anti-idiotypic antibody or antigen binding fragment according, or a complement thereof, wherein the variable light chain domain comprises VL CDR1 (L1), VL CDR2 (L2), and VL CDR3 (L3), consisting of the amino acid sequences of SEQ ID NO:1, SEQ ID NO:2 and SEQ ID NO:23 respectively, and the variable heavy chain domain comprises VH CDR1 (H1), VH CDR2 (H2), and VH CDR3 (H3), consisting of the amino acid sequences of SEQ ID NO:24, SEQ ID NO:25, and SEQ ID NO:26 respectively.

8. The nucleic acid of claim 7, wherein the nucleic acid comprises one or more nucleotide sequences selected from the group consisting of SEQ ID NO:19 and SEQ ID NO:21.

9. A vector comprising the nucleic acid of claim 7, and optionally an expression control sequence operatively linked to the nucleic acid of claim 7.

10. A host cell containing the vector of claim 9.

11. The host cell of claim 10, wherein the cell is a eukaryotic cell, a Chinese Hamster Ovary (CHO) cell or a human embryonic kidney (HEK) cell.

12. A method of producing an anti-idiotypic antibody or antigen binding fragment thereof, comprising incubating a host cell according to claim 10 such that the encoded variable heavy chain domain, variable light chain domain, or both the variable heavy chain domain and the variable light chain domain is expressed by the cell; recovering the expressed anti-idiotypic antibody or antigen binding fragment thereof; and optionally purifying the recovered anti-idiotypic antibody or antigen binding fragment thereof.

13. A composition comprising an anti-idiotypic antibody or antigen binding fragment thereof and a pharmaceutically acceptable carrier or excipient and optionally one or both of a carrier protein and an adjuvant, wherein said anti-idiotypic antibody or antigen binding fragment thereof comprises VL CDR1 (L1), VL CDR2 (L2), and VL CDR3 (L3), consisting of the amino acid sequences of SEQ ID NO:1, SEQ ID NO:2 and SEQ ID NO:23 respectively, and VH CDR1 (H1), VH CDR2 (H2), and VH CDR3 (H3), consisting of the amino acid sequences of SEQ ID NO:24, SEQ ID NO:25, and SEQ ID NO:26 respectively, and said anti-idiotypic antibody or antigen binding fragment thereof specifically binds to an antigen binding pocket of an AP33 antibody.

14. The composition according to claim 13, wherein the composition comprises the carrier protein, and the carrier protein is selected from the group consisting of tetanus toxoid and CRM 197 mutant diphtheria toxin.

15. The composition according to claim 13, wherein the pharmaceutically acceptable carrier or excipient and optionally one or both of the carrier protein and the adjuvant are nontoxic to a human recipient at the dosages and concentrations employed.

16. The anti-idiotypic antibody or antigen binding fragment of claim 1, wherein said anti-idiotypic antibody or antigen binding fragment thereof is capable of inducing in a mammal an immune response against the hepatitis C virus E2 protein.

17. The anti-idiotypic antibody or antigen binding fragment thereof of claim 1, wherein said anti-idiotypic antibody or antigen binding fragment thereof exhibits binding to said AP33 antibody mutants $F_L32A$, $N_L91A$, $W_L96A$, $Y_H33A$, $Y_H50A$, $Y_H58A$, $I_H95A$ and $Y_H100A$ of less than 50% of its binding to the AP33 antibody.

18. A method of inducing in a mammal an immune response against the hepatitis C virus E2 protein, the method comprising administering to said mammal an antibody according to claim 1, a nucleic acid according to claim 7, a vector according to claim 9, or a composition according to claim 13.

19. The anti-idiotypic antibody or antigen binding fragment thereof according to claim 1 wherein, said AP33 antibody binds a linear epitope present at residues 412-423 of the E2 polypeptide.

* * * * *

```
                           SEQUENCE LISTING

<160> NUMBER OF SEQ ID NOS: 30

<210> SEQ ID NO 1
<211> LENGTH: 11
<212> TYPE: PRT
<213> ORGANISM: Artificial Sequence
<220> FEATURE:
<223> OTHER INFORMATION: antibody sequence

<400> SEQUENCE: 1

Lys Ala Ser Gln Asn Val Arg Thr Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: antibody sequence

<400> SEQUENCE: 2

Leu Ala Ser Ser Arg His Thr
1               5

<210> SEQ ID NO 3
<211> LENGTH: 8
<212> TYPE: PRT
<213> ORGANISM: Artificial Sequence
<220> FEATURE:
<223> OTHER INFORMATION: antibody sequence

<400> SEQUENCE: 3

Leu Gln His Trp Asn Tyr Pro Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: antibody sequence

<400> SEQUENCE: 4

Asn Tyr Trp Met His
1               5
```

```
<210> SEQ ID NO 5
<211> LENGTH: 17
<212> TYPE: PRT
<213> ORGANISM: Artificial Sequence
<220> FEATURE:
<223> OTHER INFORMATION: antibody sequence

<400> SEQUENCE: 5

Glu Ile Asn Pro Ser Asp Gly His Thr Asn Tyr Asn Glu Lys Phe Lys
1               5                   10                  15

Ser

<210> SEQ ID NO 6
<211> LENGTH: 12
<212> TYPE: PRT
<213> ORGANISM: Artificial Sequence
<220> FEATURE:
<223> OTHER INFORMATION: antibody sequence

<400> SEQUENCE: 6

Pro Trp Ala Phe Gly Asn Tyr Gly Ala Trp Phe Ala
1               5                   10

<210> SEQ ID NO 7
<211> LENGTH: 109
<212> TYPE: PRT
<213> ORGANISM: Artificial Sequence
<220> FEATURE:
<223> OTHER INFORMATION: antibody sequence

<400> SEQUENCE: 7

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Ser Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Tyr
                85                  90                  95

Thr Phe Gly Gly Gly Thr Lys Leu Glu Ile Lys Arg Ala
            100                 105

<210> SEQ ID NO 8
<211> LENGTH: 122
<212> TYPE: PRT
<213> ORGANISM: Artificial Sequence
<220> FEATURE:
<223> OTHER INFORMATION: antibody sequence

<400> SEQUENCE: 8

Gln Val Gln Leu Gln Glu Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Glu Ile Asn Pro Ser Asp Gly His Thr Asn Tyr Asn Glu Lys Phe
    50                  55                  60
```

```
Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Pro Trp Ala Phe Gly Asn Tyr Gly Ala Trp Phe Ala Tyr Trp
            100                 105                 110

Gly Gln Gly Thr Leu Val Thr Val Ser Ala
        115                 120
```

<210> SEQ ID NO 9
<211> LENGTH: 338
<212> TYPE: DNA
<213> ORGANISM: Artificial Sequence
<220> FEATURE:
<223> OTHER INFORMATION: antibody coding sequence

<400> SEQUENCE: 9

```
tgtgatgacc cagtctccaa aattcatgtc cacatcagta ggagacaggg tcagcatcac    60
ctgcaaggcc agtcagaatg ttcgtactgc tgtagcctgg tatcaacaga accagggca   120 gtctcctaaa gcactgattt acttggcatc agccggcac actggagtcc ctgatcgctt   180
cacaggcagt ggatctggga cagatttcac tctcaccatt agcaatgtgc aatctgaaga   240
cctggcagat tatttctgtc tgcaacattg gaattatccg tacacgttcg gagggggac   300 caagctggaa ataaaacggg ctgatgctgc accaactg                           338
```

<210> SEQ ID NO 10
<211> LENGTH: 399
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 10

```
cttccggaat tncaggtnca gctgcaggag tctggggctg agctggtgaa gcctggggct    60
tcagtgaagc tgtcctgcaa ggcttctggc tacaccttca ccaactactg gatgcactgg   120
gttaagcaga ggcctggaca aggccttgag tggattggag agattaatcc tagcgacggt   180
catactaact acaatgagaa gttcaagagc aaggccacac tgactgtaga caaatcctcc   240
agcacagcct acatgcaact cagcagcctg acatctgagg actctgcggt ctattactgt   300
gcaagacctt gggcgtttgg taactacggg gcctggtttg cttactgggg ccaagggact   360
ctggtcactg tctctgcagc caaaacgaca cccccatct                          399
```

<210> SEQ ID NO 11
<211> LENGTH: 282
<212> TYPE: PRT
<213> ORGANISM: Artificial Sequence
<220> FEATURE:
<223> OTHER INFORMATION: scfv antibody sequence

<400> SEQUENCE: 11

```
Met Glu Thr Asp Thr Leu Leu Leu Trp Val Leu Leu Leu Trp Val Pro
 1               5                  10                  15
```

Gly Ser Thr Gly Asp Ala Asn Ser Gln Val Gln Leu Gln Glu Ser Gly
             20                  25                  30

Thr Glu Leu Val Lys Pro Gly Ala Ser Val Lys Leu Ser Cys Lys Ala
         35                  40                  45

Ser Gly Tyr Thr Phe Thr Asn Tyr Trp Met His Trp Val Lys Gln Arg
 50                  55                  60

Pro Gly Gln Gly Leu Glu Trp Ile Gly Glu Ile Asn Pro Ser Asp Gly
65                  70                  75                  80

His Thr Asn Tyr Asn Glu Lys Phe Lys Ser Lys Ala Thr Leu Thr Val
                 85                  90                  95

Asp Lys Ser Ser Ser Thr Ala Tyr Met Gln Leu Ser Ser Leu Thr Ser
            100                 105                 110

Glu Asp Ser Ala Val Tyr Tyr Cys Ala Arg Pro Trp Ala Phe Gly Asn
        115                 120                 125

Tyr Gly Ala Trp Phe Ala Tyr Trp Gly Gln Gly Thr Leu Val Thr Val
130                 135                 140

Ser Ala Gly Gly Ser Gly Gly Ser Gly Gly Gly Ser Gly Gly Gly
145                 150                 155                 160

Gly Ser Gly Gly Gly Ala Ser Asp Ile Val Met Thr Gln Ser Pro Lys
                165                 170                 175

Phe Met Ser Thr Ser Val Gly Asp Arg Val Ser Ile Thr Cys Lys Ala
            180                 185                 190

Ser Gln Asn Val Arg Thr Ala Val Ala Trp Tyr Gln Gln Lys Pro Gly
        195                 200                 205

Gln Ser Pro Lys Ala Leu Ile Tyr Leu Ala Ser Ser Arg His Thr Gly
    210                 215                 220

Val Pro Asp Arg Phe Thr Gly Ser Gly Ser Gly Thr Asp Phe Thr Leu
225                 230                 235                 240

Thr Ile Ser Asn Val Gln Ser Glu Asp Leu Ala Asp Tyr Phe Cys Leu
                245                 250                 255

Gln His Trp Asn Tyr Pro Tyr Thr Phe Gly Gly Gly Thr Lys Leu Glu
            260                 265                 270

Ile Lys Ser Arg His His His His His His
        275                 280

<210> SEQ ID NO 12
<211> LENGTH: 655
<212> TYPE: PRT
<213> ORGANISM: Artificial Sequence
<220> FEATURE:
<223> OTHER INFORMATION: MBP-B2.1A scFv fusion protein

<400> SEQUENCE: 12

Met Lys Tyr Tyr His His His His His His Asp Tyr Asp His Met Lys
1               5                   10                  15

Ile Glu Glu Gly Lys Leu Val Ile Trp Ile Asn Gly Asp Lys Gly Tyr
             20                  25                  30

Asn Gly Leu Ala Glu Val Gly Lys Lys Phe Glu Lys Asp Thr Gly Ile
         35                  40                  45

Lys Val Thr Val Glu His Pro Asp Lys Leu Glu Glu Lys Phe Pro Gln
 50                  55                  60

Val Ala Ala Thr Gly Asp Gly Pro Asp Ile Ile Phe Trp Ala His Asp
65                  70                  75                  80

Arg Phe Gly Gly Tyr Ala Gln Ser Gly Leu Leu Ala Glu Ile Thr Pro
                 85                  90                  95

```
Asp Lys Ala Phe Gln Asp Lys Leu Tyr Pro Phe Thr Trp Asp Ala Val
                100                 105                 110
Arg Tyr Asn Gly Lys Leu Ile Ala Tyr Pro Ile Ala Val Glu Ala Leu
            115                 120                 125
Ser Leu Ile Tyr Asn Lys Asp Leu Leu Pro Asn Pro Pro Lys Thr Trp
130                 135                 140
Glu Glu Ile Pro Ala Leu Asp Lys Glu Leu Lys Ala Lys Gly Lys Ser
145                 150                 155                 160
Ala Leu Met Phe Asn Leu Gln Glu Pro Tyr Phe Thr Trp Pro Leu Ile
                165                 170                 175
Ala Ala Asp Gly Gly Tyr Ala Phe Lys Tyr Glu Asn Gly Lys Tyr Asp
                180                 185                 190
Ile Lys Asp Val Gly Val Asp Asn Ala Gly Ala Lys Ala Gly Leu Thr
            195                 200                 205
Phe Leu Val Asp Leu Ile Lys Asn Lys His Met Asn Ala Asp Thr Asp
        210                 215                 220
Tyr Ser Ile Ala Glu Ala Ala Phe Asn Lys Gly Glu Thr Ala Met Thr
225                 230                 235                 240
Ile Asn Gly Pro Trp Ala Trp Ser Asn Ile Asp Thr Ser Lys Val Asn
                245                 250                 255
Tyr Gly Val Thr Val Leu Pro Thr Phe Lys Gly Gln Pro Ser Lys Pro
                260                 265                 270
Phe Val Gly Val Leu Ser Ala Gly Ile Asn Ala Ala Ser Pro Asn Lys
            275                 280                 285
Glu Leu Ala Lys Glu Phe Leu Glu Asn Tyr Leu Leu Thr Asp Glu Gly
        290                 295                 300
Leu Glu Ala Val Asn Lys Asp Lys Pro Leu Gly Ala Val Ala Leu Lys
305                 310                 315                 320
Ser Tyr Glu Glu Glu Leu Ala Lys Asp Pro Arg Ile Ala Ala Thr Met
                325                 330                 335
Glu Asn Ala Gln Lys Gly Glu Ile Met Pro Asn Ile Pro Gln Met Ser
                340                 345                 350
Ala Phe Trp Tyr Ala Val Arg Thr Ala Val Ile Asn Ala Ala Ser Gly
            355                 360                 365
Arg Gln Thr Val Asp Glu Ala Leu Lys Asp Ala Gln Thr Asn Ser Ser
        370                 375                 380
Ser Asn Asn Asn Asn Asn Asn Asn Asn Asn Leu Gly Glu Asn Leu
385                 390                 395                 400
Tyr Phe Gln Gly Ala Met Ala Gln Val Gln Leu Gln Glu Ser Gly Thr
                405                 410                 415
Glu Leu Val Lys Pro Gly Ala Ser Val Lys Leu Ser Cys Lys Ala Ser
            420                 425                 430
Gly Tyr Thr Phe Thr Asn Tyr Trp Met His Trp Val Lys Gln Arg Pro
        435                 440                 445
Gly Gln Gly Leu Glu Trp Ile Gly Glu Ile Asn Pro Ser Asp Gly His
    450                 455                 460
Thr Asn Tyr Asn Glu Lys Phe Lys Ser Lys Ala Thr Leu Thr Val Asp
465                 470                 475                 480
Lys Ser Ser Ser Thr Ala Tyr Met Gln Leu Ser Ser Leu Thr Ser Glu
                485                 490                 495
Asp Ser Ala Val Tyr Tyr Cys Ala Arg Pro Trp Ala Phe Gly Asn Tyr
            500                 505                 510
```

```
Gly Ala Trp Phe Ala Tyr Trp Gly Gln Gly Thr Leu Val Thr Val Ser
            515                 520                 525

Ala Gly Gly Ser Gly Ser Gly Gly Gly Ser Gly Gly Gly Gly
530                 535                 540

Ser Gly Gly Ala Ser Asp Ile Val Met Thr Gln Ser Pro Lys Phe
545                 550                 555                 560

Met Ser Thr Ser Val Gly Asp Arg Val Ser Ile Thr Cys Lys Ala Ser
                565                 570                 575

Gln Asn Val Arg Thr Ala Val Ala Trp Tyr Gln Gln Lys Pro Gly Gln
            580                 585                 590

Ser Pro Lys Ala Leu Ile Tyr Leu Ala Ser Ser Arg His Thr Gly Val
            595                 600                 605

Pro Asp Arg Phe Thr Gly Ser Gly Ser Gly Thr Asp Phe Thr Leu Thr
            610                 615                 620

Ile Ser Asn Val Gln Ser Glu Asp Leu Ala Asp Tyr Phe Cys Leu Gln
625                 630                 635                 640

His Trp Asn Tyr Pro Tyr Thr Phe Gly Gly Gly Thr Lys Leu Glu
                645                 650                 655
```

<210> SEQ ID NO 13
<211> LENGTH: 250
<212> TYPE: PRT
<213> ORGANISM: Artificial Sequence
<220> FEATURE:
<223> OTHER INFORMATION: MBP-B2.1A scFv fusion protein cleaved

<400> SEQUENCE: 13

```
Met Ala Gln Val Gln Leu Gln Glu Ser Gly Thr Glu Leu Val Lys Pro
1               5                   10                  15

Gly Ala Ser Val Lys Leu Ser Cys Lys Ala Ser Gly Tyr Thr Phe Thr
                20                  25                  30

Asn Tyr Trp Met His Trp Val Lys Gln Arg Pro Gly Gln Gly Leu Glu
            35                  40                  45

Trp Ile Gly Glu Ile Asn Pro Ser Asp Gly His Thr Asn Tyr Asn Glu
        50                  55                  60

Lys Phe Lys Ser Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Pro Trp Ala Phe Gly Asn Tyr Gly Ala Trp Phe Ala
            100                 105                 110

Tyr Trp Gly Gln Gly Thr Leu Val Thr Val Ser Ala Gly Gly Ser Gly
        115                 120                 125

Gly Ser Gly Gly Gly Gly Ser Gly Gly Gly Gly Ser Gly Gly Gly Ala
    130                 135                 140

Ser Asp Ile Val Met Thr Gln Ser Pro Lys Phe Met Ser Thr Ser Val
145                 150                 155                 160

Gly Asp Arg Val Ser Ile Thr Cys Lys Ala Ser Gln Asn Val Arg Thr
                165                 170                 175

Ala Val Ala Trp Tyr Gln Gln Lys Pro Gly Gln Ser Pro Lys Ala Leu
            180                 185                 190

Ile Tyr Leu Ala Ser Ser Arg His Thr Gly Val Pro Asp Arg Phe Thr
        195                 200                 205

Gly Ser Gly Ser Gly Thr Asp Phe Thr Leu Thr Ile Ser Asn Val Gln
    210                 215                 220
```

Ser Glu Asp Leu Ala Asp Tyr Phe Cys Leu Gln His Trp Asn Tyr Pro
225                 230                 235                 240

Tyr Thr Phe Gly Gly Gly Thr Lys Leu Glu
            245                 250

<210> SEQ ID NO 14
<211> LENGTH: 402
<212> TYPE: DNA
<213> ORGANISM: Artificial Sequence
<220> FEATURE:
<223> OTHER INFORMATION: AP33 WT VH

<400> SEQUENCE: 14
atggtgttaa gtcttctgta cctgttgaca gcccttccgg gtatcctgtc agaggtgcag      60
cttcaggagt caggacctag cctcgtgaaa ccttctcaga ctctgtccct cacctgttct     120
gtcactggcg actccatcac cagtggttac tggaactgga tccggaaatt cccagggaat     180
aaacttgagt acatgggata cataagttac agtggtagca cttactacaa tctatctctc     240
agaagtcgca tctccatcac tcgagacaca tccaagaatc agtactacct gcagttgaat     300
tctgtgacta ctgaggacac agccacatat tactgtgcgc tcattactac gactacctat     360
gctatggact actggggtca aggaacctca gtcaccgtct cc                        402

<210> SEQ ID NO 15
<211> LENGTH: 393
<212> TYPE: DNA
<213> ORGANISM: Artificial Sequence
<220> FEATURE:
<223> OTHER INFORMATION: AP33 WT VL

<400> SEQUENCE: 15
atggagacag acacactcct gctatgggtg ctgctgctct gggttccagg ttccacaggt      60
aacattgtgc tgacccaatc tccagttttct ttggctgtgt ctctggggca gagggccacc    120
atttcctgca gagccagtga aagtgttgat ggttatggca atagttttct gcactggttc     180
cagcagaaac aggacagcc acccaaactc ctcatctatc ttgcatccaa cctaaactct      240
ggggtccctg ccaggttcag tggcagtggg tctaggacag acttcaccct caccattgat     300
cctgtggagg ctgatgatgc tgcaacctat tactgtcagc aaaataatgt ggaccgtgg      360 acgttcggtg gaggcaccaa gctggaaatc aaa                                  393

<210> SEQ ID NO 16
<211> LENGTH: 5842
<212> TYPE: DNA
<213> ORGANISM: Artificial Sequence
<220> FEATURE:
<223> OTHER INFORMATION: sc fv coding sequence

<400> SEQUENCE: 16
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgacccccgc ccattgacgt caataatgac gtatgttccc atagtaacgc     180
caatagggac tttccattga cgtcaatggg tggactattt acgtaaaact gcccacttgg     240
cagtacatca agtgtatcat atgccaagta cgccccctat tgacgtcaat gacggtaaat     300
ggcccgcctg gcattatgcc cagtacatga ccttatggga ctttcctact tggcagtaca     360
tctacgtatt agtcatcgct attaccatgg tgatgcggtt ttggcagtac atcaatgggc     420
gtggatagcg gtttgactca cggggatttc caagtctcca ccccattgac gtcaatggga     480

```
gtttgttttg gcaccaaaat caacgggact ttccaaaatg tcgtaacaac tccgccccat    540
tgacgcaaat gggcggtagg cgtgtacggt gggaggtcta tataagcaga gctctctggc    600
taactagaga acccactgct tactggctta tcgaaattaa tacgactcac tatagggaga    660
cccaagcttg gtaccgagct cggatctact agtaacggcc gccagtgtgc tggatttcgg    720
cttggggata tccaccatgg agacagacac actcctgcta tgggtactgc tgctctgggt    780
tccaggttcc actggtgacg cgaattcgca ggttcagctg caggagtctt gggctgagct    840
ggtgaagcct ggggcttcag tgaagctgtc ctgcaaggct tctggctaca ccttcaccaa    900
ctactggatg cactgggtta agcagaggcc tggacaaggc cttgagtgga ttggagagat    960
taatcctagc gacggtcata ctaactacaa tgagaagttc aagagcaagg ccacactgac   1020
tgtagacaaa tcctccagca cagcctacat gcaactcagc agcctgacat ctgaggactc   1080
tgcggtctat tactgtgcaa gaccttgggc gtttggtaac tacggggcct ggtttgctta   1140
ctggggccaa gggactctgg tcactgtctc tgccggggga tccggtggat caggaggtgg   1200
cggatctggt ggaggcggtt caggaggagg tgctagcgat atagtgatga cccagtctcc   1260
aaaattcatg tccacatcag taggagacag ggtcagcatc acctgcaagg ccagtcagaa   1320
tgttcgtact gctgtagcct ggtatcaaca gaaaccaggg cagtctccta aagcactgat   1380
ttacttggca tccagccggc acactggagt ccctgatcgc ttcacaggca gtggatctgg   1440
gacagatttc actctcacca ttagcaatgt gcaatctgaa gacctggcag attatttctg   1500
tctgcaacat tggaattatc cgtacacgtt cggaggggg accaagtcta gacatcacca   1560
tcaccatcac taggcttccg ctcgagatca gcctcgactg tgccttctag ttgccagcca   1620
tctgttgttt gccctcccc cgtgccttcc ttgaccctgg aaggtgccac tcccactgtc    1680
ctttcctaat aaaatgagga attgcatcg cattgtctga gtaggtgtca ttctattctg   1740
gggggtgggg tggggcagga cagcaagggg gaggattggg aagacaatag caggcatgct   1800
ggggatgcgg tgggctctat ggcttctgag gcggaaagaa ccagtggcgg taatacggtt   1860
atccacagaa tcaggggata acgcaggaaa gaacatgtga gcaaaaggcc agcaaaaggc   1920
caggaaccgt aaaaaggccg cgttgctggc gtttttccat aggctccgcc ccctgacga    1980 gcatcacaaa aatcgacgct caagtcagag gtggcgaaac ccgacaggac tataaagata   2040
ccaggcgttt ccccctggaa gctccctcgt gcgctctcct gttccgaccc tgccgcttac   2100
cggatacctg tccgccttc tcccttcggg aagcgtggcg ctttctcata gctcacgctg   2160
taggtatctc agttcggtgt aggtcgttcg ctccaagctg ggctgtgtgc acgaaccccc   2220
cgttcagccc gaccgctgcg ccttatccgg taactatcgt cttgagtcca acccggtaag   2280
acacgactta tcgccactgg cagcagccac tggtaacagg attagcagag cgaggtatgt   2340
aggcggtgct acagagttct tgaagtggtg gcctaactac ggctacacta aaggacagt    2400 atttggtatc tgcgctctgc tgaagccagt taccttcgga aaaagagttg gtagctcttg   2460
atccggcaaa caaaccaccg ctggtagcgg tggttttttt gtttgcaagc agcagattac   2520
gcgcagaaaa aaaggatctc aagaagatcc tttgatcttt tctacggggt ctgacgctca   2580
gtggaacgaa aactcacgtt aagggatttt ggtcatgaga ttatcaaaaa ggatcttcac   2640
ctagatcctt ttaaattaaa aatgaagttt taaatcaatc taagtatat atgagtaacc   2700 tgaggctatg gcagggcctg ccgccccgac gttggctgcg agccctgggc cttcacccga   2760
acttgggggg tggggtgggg aaaaggaaga aacgcgggcg tattggcccc aatggggtct   2820
```

```
cggtggggta tcgacagagt gccagccctg ggaccgaacc ccgcgtttat gaacaaacga   2880
cccaacaccg tgcgttttat tctgtctttt tattgccgtc atagcgcggg ttccttccgg   2940
tattgtctcc ttccgtgttt cagttagcct cccccctaggg tgggcgaaga actccagcat   3000
gagatccccg cgctggagga tcatccagcc ggcgtcccgg aaaacgattc cgaagcccaa   3060
cctttcatag aaggcggcgg tggaatcgaa atctcgtgat ggcaggttgg gcgtcgcttg   3120
gtcggtcatt tcgaacccca gagtcccgct cagaagaact cgtcaagaag gcgatagaag   3180
gcgatgcgct gcgaatcggg agcggcgata ccgtaaagca cgaggaagcg gtcagcccat   3240
tcgccgccaa gctcttcagc aatatcacgg gtagccaacg ctatgtcctg atagcggtcc   3300
gccacaccca gccggccaca gtcgatgaat ccagaaaagc ggccattttc caccatgata   3360
ttcggcaagc aggcatcgcc atgggtcacg acgagatcct cgccgtcggg catgctcgcc   3420
ttgagcctgg cgaacagttc ggctggcgcg agcccctgat gctcttgatc atcctgatcg   3480
acaagaccgg cttccatccg agtacgtgct cgctcgatgc gatgtttcgc ttggtggtcg   3540
aatgggcagg tagccggatc aagcgtatgc agccgccgca ttgcatcagc catgatggat   3600
actttctcgg caggagcaag gtgagatgac aggagatcct gccccggcac ttcgcccaat   3660
agcagccagt cccttcccgc ttcagtgaca acgtcgagca cagctgcgca aggaacgccc   3720
gtcgtggcca gccacgatag ccgcgctgcc tcgtcttgca gttcattcag ggcaccggac   3780
aggtcggtct tgacaaaaag aaccgggcgc ccctgcgctg acagccgaaa cacggcggca   3840
tcagagcagc cgattgtctg ttgtgcccag tcatagccga atagcctctc cacccaagcg   3900
gccggagaac ctgcgtgcaa tccatcttgt tcaatcatgc gaaacgatcc tcatcctgtc   3960
tcttgatcga tctttgcaaa agcctaggcc tccaaaaaag cctcctcact acttctggaa   4020
tagctcagag gccgaggagg cggcctcggc ctctgcataa ataaaaaaaa ttagtcagcc   4080 atgggcgga gaatgggcgg aactgggcgg agttaggggc gggatgggcg gagttagggg   4140
cgggactatg gttgctgact aattgagatg catgctttgc atacttctgc ctgctgggga   4200
gcctggggac tttccacacc tggttgctga ctaattgaga tgcatgcttt gcatacttct   4260
gcctgctggg gagcctgggg actttccaca ccctaactga cacacattcc acagctggtt   4320
ctttccgcct caggactctt cctttttcaa taaatcaatc taaagtatat atgagtaaac   4380
ttggtctgac agttaccaat gcttaatcag tgaggcacct atctcagcga tctgtctatt   4440
tcgttcatcc atagttgcct gactccccgt cgtgtagata actacgatac gggagggctt   4500
accatctggc cccagtgctg caatgatacc gcgagaccca cgctcaccgg ctccagattt   4560
atcagcaata aaccagccag ccggaagggc cgagcgcaga agtggtcctg caactttatc   4620
cgcctccatc cagtctatta attgttgccg ggaagctaga gtaagtagtt cgccagttaa   4680 tagtttcgc aacgttgttg ccattgctac aggcatcgtg gtgtcacgct cgtcgtttgg   4740
tatggcttca ttcagctccg gttcccaacg atcaaggcga gttacatgat cccccatgtt   4800
gtgcaaaaaa gcggttagct ccttcggtcc tccgatcgtt gtcagaagta agttggccgc   4860
agtgttatca ctcatggtta tggcagcact gcataattct cttactgtca tgccatccgt   4920
aagatgcttt tctgtgactg gtgagtactc aaccaagtca ttctgagaat agtgtatgcg   4980
gcgaccgagt tgctcttgcc cggcgtcaat acgggataat accgcgccac atagcagaac   5040
tttaaaagtg ctcatcattg gaaaacgttc ttcggggcga aaactctcaa ggatcttacc   5100
gctgttgaga tccagttcga tgtaacccac tcgtgcaccc aactgatctt cagcatcttt   5160
tactttcacc agcgtttctg ggtgagcaaa aacaggaagg caaaatgccg caaaaaaggg   5220
```

```
aataagggcg acacggaaat gttgaatact catactcttc cttttttcaat attattgaag    5280 catttatcag ggttattgtc tcatgagcgg atacatattt gaatgtattt agaaaaataa    5340
acaaataggg gttccgcgca catttccccg aaaagtgcca cctgacgcgc cctgtagcgg    5400
cgcattaagc gcggcgggtg tggtggttac gcgcagcgtg accgctacac ttgccagcgc    5460
cctagcgccc gctcctttcg ctttcttccc ttcctttctc gccacgttcg ccggctttcc    5520
ccgtcaagct ctaaatcggg ggctcccttt agggttccga tttagtgctt tacggcacct    5580
cgaccccaaa aaacttgatt agggtgatgg ttcacgtagt gggccatcgc cctgatagac    5640
ggtttttcgc cctttgacgt tggagtccac gttctttaat agtggactct tgttccaaac    5700
tggaacaaca ctcaaccta tctcggtcta ttcttttgat ttataaggga ttttgccgat    5760
ttcggcctat tggttaaaaa atgagctgat ttaacaaaaa tttaacgcga atttttaacaa    5820 aatattaacg cttacaattt ac                                            5842

<210> SEQ ID NO 17
<211> LENGTH: 4838
<212> TYPE: DNA
<213> ORGANISM: Artificial Sequence
<220> FEATURE:
<223> OTHER INFORMATION: B2.1A vH sequence cloned into pFUSEss-CHIg-Mg1

<400> SEQUENCE: 17
ggatctgcga tcgctccggt gcccgtcagt gggcagagcg cacatcgccc acagtccccg      60
agaagttggg gggagggggtc ggcaattgaa cgggtgccta gagaaggtgg cgcggggtaa    120
actgggaaag tgatgtcgtg tactggctcc gccttttttcc cgagggtggg ggagaaccgt    180
atataagtgc agtagtcgcc gtgaacgttc ttttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggtctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgcaggttca gctgcaggag tctggggctg    660
agctggtgaa gcctggggct tcagtgaagc tgtcctgcaa ggcttctggc tacaccttca    720
ccaactactg gatgcactgg gttaagcaga ggcctggaca aggccttgag tggattggag    780
agattaatcc tagcgacggt catactaact acaatgagaa gttcaagagc aaggccacac    840
tgactgtaga caaatcctcc agcacagcct acatgcaact cagcagcctg acatctgagg    900
actctgcggt ctattactgt gcaagacctt gggcgtttgg taactacggg gcctggtttg    960
cttactgggg ccaagggact ctggtcactg tctctgccgc taaaacgaca ccccccatctg    1020 tctatccact ggcccctgga tctgctgccc aaactaactc catggtgacc ctgggatgcc    1080
tggtcaaggg ctatttccct gagccagtga cagtgacctg gaactctgga tccctgtcca    1140
gcggtgtgca caccttccca gctgtcctgc agtctgacct ctacactctg agcagctcag    1200
tgactgtccc ctccagcacc tggcccagcg agaccgtcac ctgcaacgtt gcccacccgg    1260
ccagcagcac caaggtggac aagaaaattg tgcccaggga ttgtggttgt aagccttgca    1320
tatgtacagt cccagaagta tcatctgtct tcatcttccc cccaaagccc aaggatgtgc    1380
```

-continued

```
tcaccattac tctgactcct aaggtcacgt gtgttgtggt agacatcagc aaggatgatc    1440
ccgaggtcca gttcagctgg tttgtagatg atgtggaggt gcacacagct cagacgcaac    1500
cccgggagga gcagttcaac agcactttcc gctcagtcag tgaacttccc atcatgcacc    1560
aggactggct caatgcaag gagttcaaat gcagggtcaa cagtgcagct ttccctgccc     1620
ccatcgagaa aaccatctcc aaaaccaaag gcagaccgaa ggctccacag gtgtacacca    1680
ttccacctcc caaggagcag atggccaagg ataaagtcag tctgacctgc atgataacag    1740
acttcttccc tgaagacatt actgtggagt ggcagtggaa tgggcagcca gcggagaact    1800
acaagaacac tcagcccatc atggacacag atggctctta cttcgtctac agcaagctca    1860
atgtgcagaa gagcaactgg gaggcaggaa atactttcac ctgctctgtg ttacatgagg    1920
gcctgcacaa ccaccatact gagaagagcc tctcccactc tcctggtaaa tgatcccagt    1980
gtccctagct ggccagacat gataagatac attgatgagt ttggacaaac cacaactaga    2040
atgcagtgaa aaaatgctt tatttgtgaa atttgtgatg ctattgcttt atttgtaacc     2100
attataagct gcaataaaca agttaacaac aacaattgca ttcattttat gtttcaggtt    2160
cagggggagg tgtgggaggt tttttaaagc aagtaaaacc tctacaaatg tggtatggaa    2220
ttaattctaa aatacagcat agcaaaactt aacctccaa atcaagcctc tacttgaatc     2280
cttttctgag ggatgaataa ggcataggca tcaggggctg ttgccaatgt gcattagctg    2340
tttgcagcct caccttcttt catggagttt aagatatagt gtattttccc aaggtttgaa    2400
ctagctcttc atttctttat gttttaaatg cactgacctc ccacattccc tttttagtaa    2460
aatattcaga aataatttaa atacatcatt gcaatgaaaa taaatgtttt ttattaggca    2520
gaatccagat gctcaaggcc cttcataata tcccccagtt tagtagttgg acttagggaa    2580
caaaggaacc tttaatagaa attggacagc aagaaagcga gcttctagct tatcctcagt    2640
cctgctcctc tgccacaaag tgcacgcagt tgccggccgg gtcgcgcagg gcgaactccc    2700 gccccacgg ctgctcgccg atctcggtca tggccggccc ggaggcgtcc cggaagttcg     2760
tggacacgac ctccgaccac tcggcgtaca gctcgtccag gccgcgcacc cacacccagg    2820
ccagggtgtt gtccggcacc acctggtcct ggaccgcgct gatgaacagg gtcacgtcgt    2880
cccggaccac accggcgaag tcgtcctcca cgaagtcccg ggagaacccg agccggtcgg    2940
tccagaactc gaccgctccg gcgacgtcgc gcgcggtgag caccggaacg gcactggtca    3000
acttggccat gatggctcct cctgtcagga gaggaaagag aagaaggtta gtacaattgc    3060
tatagtgagt tgtattatac tatgcagata tactatgcca atgattaatt gtcaaactag    3120
ggctgcaggg ttcatagtgc cacttttcct gcactgcccc atctcctgcc cacccttcc    3180 caggcataga cagtcagtga cttaccaaac tcacaggagg gagaaggcag aagcttgaga    3240
cagacccgcg ggaccgccga actgcgaggg gacgtggcta gggcggcttc ttttatggtg    3300
cgccggccct cggaggcagg gcgctcgggg aggcctagcg gccaatctgc ggtggcagga    3360
ggcggggccg aaggccgtgc ctgaccaatc cggagcacat aggagtctca gccccccgcc    3420
ccaaagcaag gggaagtcac gcgcctgtag cgccagcgtg ttgtgaaatg ggggcttggg    3480
ggggttgggg ccctgactag tcaaaacaaa ctcccattga cgtcaatggg gtggagactt    3540
ggaaatcccc gtgagtcaaa ccgctatcca cgcccattga tgtactgcca aaccgcatc     3600 atcatggtaa tagcgatgac taatacgtag atgtactgcc aagtaggaaa gtcccataag    3660
gtcatgtact gggcataatg ccaggcgggc catttaccgt cattgacgtc aatagggggc    3720
gtacttggca tatgatacac ttgatgtact gccaagtggg cagtttaccg taaatactcc    3780
```

```
acccattgac gtcaatggaa agtccctatt ggcgttacta tgggaacata cgtcattatt    3840
gacgtcaatg ggcggggggtc gttgggcggt cagccaggcg ggccatttac cgtaagttat    3900
gtaacgcctg caggttaatt aagaacatgt gagcaaaagg ccagcaaaag gccaggaacc    3960
gtaaaaaggc cgcgttgctg gcgtttttcc ataggctccg ccccctgac gagcatcaca    4020 aaaatcgacg ctcaagtcag aggtggcgaa acccgacagg actataaaga taccaggcgt    4080
ttccccctgg aagctccctc gtgcgctctc ctgttccgac cctgccgctt accggatacc    4140
tgtccgcctt tctcccttcg ggaagcgtgg cgctttctca tagctcacgc tgtaggtatc    4200
tcagttcggt gtaggtcgtt cgctccaagc tgggctgtgt gcacgaaccc cccgttcagc    4260
ccgaccgctg cgccttatcc ggtaactatc gtcttgagtc caacccggta agacacgact    4320
tatcgccact ggcagcagcc actggtaaca ggattagcag agcgaggtat gtaggcggtg    4380
ctacagagtt cttgaagtgg tggcctaact acggctacac tagaagaaca gtatttggta    4440
tctgcgctct gctgaagcca gttaccttcg gaaaaagagt tggtagctct tgatccggca    4500
aacaaaccac cgctggtagc ggtggttttt ttgtttgcaa gcagcagatt acgcgcagaa    4560
aaaaaggatc tcaagaagat cctttgatct tttctacggg gtctgacgct cagtggaacg    4620
aaaactcacg ttaagggatt ttggtcatgg ctagttaatt aacatttaaa tcagcggccg    4680
caataaaata tctttatttt cattacatct gtgtgttggt tttttgtgtg aatcgtaact    4740
aacatacgct ctccatcaaa acaaaacgaa acaaaacaaa ctagcaaaat aggctgtccc    4800
cagtgcaagt gcaggtgcca gaacatttct ctatcgaa                            4838

<210> SEQ ID NO 18
<211> LENGTH: 4162
<212> TYPE: DNA
<213> ORGANISM: Artificial Sequence
<220> FEATURE:
<223> OTHER INFORMATION: B2.1A vL sequence cloned into pFUSEss-CLIg-Mk

<400> SEQUENCE: 18
ggatctgcga tcgctccggt gcccgtcagt gggcagagcg cacatcgccc acagtccccg      60
agaagttggg gggagggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac     240
agctgaagct tcgaggggct cgcatctctc cttcacgcgc ccgccgccct acctgaggcc     300
gccatccacg ccgttgagt gcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg taccggcgc     540 ctacctgaga tcaacatgta caggatgcaa ctcctgtctt gcattgcact aagtcttgca     600
cttgtcacga attcagatat agtgatgacc cagtctccaa aattcatgtc cacatcagta     660
ggagacaggg tcagcatcac ctgcaaggcc agtcagaatg ttcgtactgc tgtagcctgg     720
tatcaacaga aaccagggca gtctcctaaa gcactgattt acttggcatc cagccggcac     780
actggagtcc ctgatcgctt cacaggcagt ggatctggga cagatttcac tctcaccatt     840
agcaatgtgc aatctgaaga cctggcagat tatttctgtc tgcaacattg gaattatccg     900
tacacgttcg gaggggggac caagctcgag atcaaacggg cagatgctgc accaactgta     960
```

```
tccatcttcc caccatccag tgagcagtta acatctggag gtgcctcagt cgtgtgcttc    1020
ttgaacaact tctaccccaa agacatcaat gtcaagtgga agattgatgg cagtgaacga    1080
caaaatggcg tcctgaacag ttggactgat caggacagca agacagcac ctacagcatg     1140 agcagcaccc tcacgttgac caaggacgag tatgaacgac ataacagcta tacctgtgag    1200
gccactcaca agacatcaac ttcacccatt gtcaagagct tcaacaggaa tgagtgttag    1260
agacaaaggt cctgagagct agctggccag acatgataag atacattgat gagtttggac    1320
aaaccacaac tagaatgcag tgaaaaaaat gctttatttg tgaaatttgt gatgctattg    1380
ctttatttgt aaccattata agctgcaata acaagttaa caacaacaat tgcattcatt      1440
ttatgtttca ggttcagggg gaggtgtggg aggtttttta aagcaagtaa aacctctaca    1500
aatgtggtat ggaattaatt ctaaaataca gcatagcaaa actttaacct ccaaatcaag    1560
cctctacttg aatcctttc tgagggatga ataaggcata ggcatcaggg gctgttgcca     1620
atgtgcatta gctgtttgca gcctcacctt ctttcatgga gtttaagata tagtgtattt    1680
tcccaaggtt tgaactagct cttcatttct ttatgtttta aatgcactga cctcccacat    1740 tccctttta gtaaaatatt cagaaataat ttaaatacat cattgcaatg aaaataaatg      1800 tttttatta ggcagaatcc agatgctcaa ggcccttcat aatatccccc agtttagtag      1860
ttggacttag ggaacaaagg aacctttaat agaaattgga cagcaagaaa gcgagcttct    1920
agctttagtt cctggtgtac ttgagggga tgagttcctc aatggtggtt ttgaccagct      1980
tgccattcat ctcaatgagc acaaagcagt caggagcata gtcagagatg agctctctgc    2040
acatgccaca ggggctgacc accctgatgg atctgtccac ctcatcagag taggggtgcc    2100
tgacagccac aatggtgtca aagtccttct gcccgttgct cacagcagac ccaatggcaa    2160
tggcttcagc acagacagtg accctgccaa tgtaggcctc aatgtggaca gcagagatga    2220
tctccccagt cttggtcctg atggccgccc cgacatggtg cttgttgtcc tcatagagca    2280
tggtgatctt ctcagtggcg acctccacca gctccagatc ctgctgagag atgttgaagg    2340
tcttcatgat ggctcctcct gtcaggagag gaaagagaag aaggttagta caattgctat    2400
agtgagttgt attatactat gcttatgatt aattgtcaaa ctagggctgc agggttcata    2460
gtgccacttt tcctgcactg ccccatctcc tgcccaccct ttcccaggca tagacagtca    2520
gtgacttacc aaactcacag gagggagaag gcagaagctt gagacagacc cgcgggaccg    2580
ccgaactgcg aggggacgtg gctagggcgg cttcttttat ggtgcgccgg ccctcggagg    2640
cagggcgctc ggggaggcct agcggccaat ctgcggtggc aggaggcggg gccgaaggcc    2700
gtgcctgacc aatccggagc acataggagt ctcagccccc cgccccaaag caggggaag     2760 tcacgcgcct gtagcgccag cgtgttgtga aatgggggct tggggggggtt ggggccctga    2820 ctagtcaaaa caaactccca ttgacgtcaa tggggtggag acttggaaat ccccgtgagt    2880
caaaccgcta tccacgccca ttgatgtact gccaaaaccg catcatcatg gtaatagcga    2940
tgactaatac gtagatgtac tgccaagtag gaaagtccca taaggtcatg tactgggcat    3000
aatgccaggc gggccattta ccgtcattga cgtcaatagg gggcgtactt ggcatatgat    3060
acacttgatg tactgccaag tgggcagttt accgtaaata ctccacccat tgacgtcaat    3120
ggaaagtccc tattggcgtt actatgggaa catacgtcat tattgacgtc aatgggcggg    3180
ggtcgttggg cggtcagcca ggcgggccat ttaccgtaag ttatgtaacg cctgcaggtt    3240
aattaagaac atgtgagcaa aaggccagca aaaggccagg aaccgtaaaa aggccgcgtt    3300
gctggcgttt ttccataggc tccgcccccc tgacgagcat cacaaaaatc gacgctcaag    3360
```

```
tcagaggtgg cgaaacccga caggactata aagataccag gcgttttccc ctggaagctc    3420
cctcgtgcgc tctcctgttc cgaccctgcc gcttaccgga tacctgtccg cctttctccc    3480
ttcgggaagc gtggcgcttt ctcatagctc acgctgtagg tatctcagtt cggtgtaggt    3540
cgttcgctcc aagctgggct gtgtgcacga acccccgtt cagcccgacc gctgcgcctt    3600
atccggtaac tatcgtcttg agtccaaccc ggtaagacac gacttatcgc cactggcagc    3660
agccactggt aacaggatta gcagagcgag gtatgtaggc ggtgctacag agttcttgaa    3720
gtggtggcct aactacggct acactagaag aacagtattt ggtatctgcg ctctgctgaa    3780
gccagttacc ttcggaaaaa gagttggtag ctcttgatcc ggcaaacaaa ccaccgctgg    3840
tagcggtggt ttttttgttt gcaagcagca gattacgcgc agaaaaaaag gatctcaaga    3900
agatcctttg atcttttcta cggggtctga cgctcagtgg aacgaaaact cacgttaagg    3960
gattttggtc atggctagtt aattaacatt taaatcagcg gccgcaataa aatatcttta    4020
ttttcattac atctgtgtgt tggttttttg tgtgaatcgt aactaacata cgctctccat    4080
caaaacaaaa cgaaacaaaa caaactagca aaataggctg tccccagtgc aagtgcaggt    4140
gccagaacat ttctctatcg aa                                             4162

<210> SEQ ID NO 19
<211> LENGTH: 324
<212> TYPE: DNA
<213> ORGANISM: Artificial Sequence
<220> FEATURE:
<223> OTHER INFORMATION: antibody coding sequence

<400> SEQUENCE: 19
gatatagtga tgacccagtc tccaaaattc atgtccacat cagtaggaga cagggtcagc      60
atcacctgca aggccagtca gaatgttcgt actgctgtag cctggtatca acagaaacca     120
gggcagtctc ctaaagcact gatttacttg gcatccagcc ggcacactgg agtccctgat     180
cgcttcacag gcagtggatc tgggacagat ttcactctca ccattagcaa tgtgcaatct     240
gaagacctgg cagattattt ctgtctgcaa cattggaatt atccgtacac gttcggaggg     300
gggaccaagc tggaaataaa acgg                                            324

<210> SEQ ID NO 20
<211> LENGTH: 108
<212> TYPE: PRT
<213> ORGANISM: Artificial Sequence
<220> FEATURE:
<223> OTHER INFORMATION: antibody sequence

<400> SEQUENCE: 20

Asp Ile Val Met Thr Gln Ser Pro Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Ser Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Tyr
                85                  90                  95
```

```
Thr Phe Gly Gly Gly Thr Lys Leu Glu Ile Lys Arg
            100                 105
```

<210> SEQ ID NO 21
<211> LENGTH: 366
<212> TYPE: DNA
<213> ORGANISM: Artificial Sequence
<220> FEATURE:
<223> OTHER INFORMATION: antibody coding sequence

<400> SEQUENCE: 21

```
caggttcagc tgcaggagtc tgggactgag ctggtgaagc ctggggcttc agtgaagctg      60
tcctgcaagg cttctggcta ccttcacc aactactgga tgcactgggt taagcagagg       120
cctggacaag gccttgagtg gattggagag attaatccta gcgacggtca tactaactac     180
aatgagaagt tcaagagcaa ggccacactg actgtagaca atcctccag cacagcctac      240 atgcaactca gcagcctgac atctgaggac tctgcggtct attactgtgc aagaccttgg    300
gcgtttggta actacggggc ctggtttgct tactggggcc aagggactct ggtcactgtc    360
tctgca                                                                366
```

<210> SEQ ID NO 22
<211> LENGTH: 122
<212> TYPE: PRT
<213> ORGANISM: Artificial Sequence
<220> FEATURE:
<223> OTHER INFORMATION: antibody sequence

<400> SEQUENCE: 22

```
Gln Val Gln Leu Gln Glu Ser Gly Thr Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Glu Ile Asn Pro Ser Asp Gly His Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Pro Trp Ala Phe Gly Asn Tyr Gly Ala Trp Phe Ala Tyr Trp
            100                 105                 110

Gly Gln Gly Thr Leu Val Thr Val Ser Ala
        115                 120
```

<210> SEQ ID NO 23
<211> LENGTH: 9
<212> TYPE: PRT
<213> ORGANISM: Artificial Sequence
<220> FEATURE:
<223> OTHER INFORMATION: antibody sequence

<400> SEQUENCE: 23

```
Leu Gln His Trp Asn Tyr Pro Tyr Thr
1               5
```

<210> SEQ ID NO 24
<211> LENGTH: 8
<212> TYPE: PRT
<213> ORGANISM: Artificial Sequence
<220> FEATURE:
<223> OTHER INFORMATION: antibody sequence

<400> SEQUENCE: 24

Gly Tyr Thr Phe Thr Asn Tyr Trp
1               5

<210> SEQ ID NO 25
<211> LENGTH: 6
<212> TYPE: PRT
<213> ORGANISM: Artificial Sequence
<220> FEATURE:
<223> OTHER INFORMATION: antibody sequence

<400> SEQUENCE: 25

Asn Pro Ser Asp Gly His
1               5

<210> SEQ ID NO 26
<211> LENGTH: 13
<212> TYPE: PRT
<213> ORGANISM: Artificial Sequence
<220> FEATURE:
<223> OTHER INFORMATION: antibody sequence

<400> SEQUENCE: 26

Pro Trp Ala Phe Gly Asn Tyr Gly Ala Trp Phe Ala Tyr
1               5                   10

<210> SEQ ID NO 27
<211> LENGTH: 5842
<212> TYPE: DNA
<213> ORGANISM: Artificial Sequence
<220> FEATURE:
<223> OTHER INFORMATION: pDisMod2-B2.1A-scFv

<400> SEQUENCE: 27

| | | | | | |
|---|---|---|---|---|---|
| gcgcgcgttg | acattgatta | ttgactagtt | attaatagta | atcaattacg | gggtcattag | 60 |
| ttcatagccc | atatatggag | ttccgcgtta | cataacttac | ggtaaatggc | ccgcctggct | 120 |
| gaccgcccaa | cgaccccgc | ccattgacgt | caataatgac | gtatgttccc | atagtaacgc | 180 |
| caatagggac | tttccattga | cgtcaatggg | tggactattt | acggtaaact | gcccacttgg | 240 |
| cagtacatca | agtgtatcat | atgccaagta | cgccccctat | tgacgtcaat | gacggtaaat | 300 |
| ggcccgcctg | gcattatgcc | cagtacatga | ccttatggga | ctttcctact | tggcagtaca | 360 |
| tctacgtatt | agtcatcgct | attaccatgg | tgatgcggtt | ttggcagtac | atcaatgggc | 420 |
| gtggatagcg | gtttgactca | cggggatttc | caagtctcca | ccccattgac | gtcaatggga | 480 |
| gtttgttttg | gcaccaaaat | caacgggact | ttccaaaatg | tcgtaacaac | tccgccccat | 540 |
| tgacgcaaat | gggcggtagg | cgtgtacggt | gggaggtcta | tataagcaga | gctctctggc | 600 |
| taactagaga | acccactgct | tactggctta | tcgaaattaa | tacgactcac | tatagggaga | 660 |
| cccaagcttg | gtaccgagct | cggatctact | agtaacggcc | gccagtgtgc | tggatttcgg | 720 |
| cttggggata | tccaccatgg | agacagacac | actcctgcta | tgggtactgc | tgctctgggt | 780 |
| tccaggttcc | actggtgacg | cgaattcgca | ggttcagctg | caggagtctg | gactgagct | 840 |
| ggtgaagcct | ggggcttcag | tgaagctgtc | ctgcaaggct | tctggctaca | ccttcaccaa | 900 |
| ctactggatg | cactgggtta | agcagaggcc | tggacaaggc | cttgagtgga | ttggagagat | 960 |
| taatcctagc | gacggtcata | ctaactacaa | tgagaagttc | aagagcaagg | ccacactgac | 1020 |
| tgtagacaaa | tcctccagca | cagcctacat | gcaactcagc | agcctgacat | ctgaggactc | 1080 |

```
tgcggtctat tactgtgcaa gaccttgggc gtttggtaac tacgggcct ggtttgctta    1140 ctggggccaa gggactctgg tcactgtctc tgccgggga tccggtggat caggaggtgg    1200
cggatctggt ggaggcggtt caggaggagg tgctagcgat atagtgatga cccagtctcc    1260
aaaattcatg tccacatcag taggagacag ggtcagcatc acctgcaagg ccagtcagaa    1320
tgttcgtact gctgtagcct ggtatcaaca gaaaccaggg cagtctccta aagcactgat    1380
ttacttggca tccagccggc acactggagt ccctgatcgc ttcacaggca gtggatctgg    1440
gacagatttc actctcacca ttagcaatgt gcaatctgaa gacctggcag attatttctg    1500
tctgcaacat tggaattatc cgtacacgtt cggaggggg accaagtcta gacatcacca    1560
tcaccatcac taggcttccg ctcgagatca gcctcgactg tgccttctag ttgccagcca    1620
tctgttgttt gcccctcccc cgtgccttcc ttgaccctgg aaggtgccac tcccactgtc    1680
ctttcctaat aaaatgagga aattgcatcg cattgtctga gtaggtgtca ttctattctg    1740
gggggtgggg tggggcagga cagcaagggg gaggattggg aagacaatag caggcatgct    1800
ggggatgcgg tgggctctat ggcttctgag gcggaaagaa ccagtggcgg taatacggtt    1860
atccacagaa tcaggggata acgcaggaaa gaacatgtga gcaaaaggcc agcaaaaggc    1920
caggaaccgt aaaaaggccg cgttgctggc gttttccat aggctccgcc cccctgacga    1980
gcatcacaaa aatcgacgct caagtcagag gtggcgaaac ccgacaggac tataaagata    2040
ccaggcgttt ccccctggaa gctccctcgt gcgctctcct gttccgaccc tgccgcttac    2100
cggatacctg tccgcctttc tcccttcggg aagcgtggcg ctttctcata gctcacgctg    2160
taggtatctc agttcggtgt aggtcgttcg ctccaagctg ggctgtgtgc acgaaccccc    2220
cgttcagccc gaccgctgcg ccttatccgg taactatcgt cttgagtcca acccggtaag    2280
acacgactta tcgccactgg cagcagccac tggtaacagg attagcagag cgaggtatgt    2340
aggcggtgct acagagttct tgaagtggtg gcctaactac ggctacacta aggacagt      2400 atttggtatc tgcgctctgc tgaagccagt taccttcgga aaaagagttg gtagctcttg    2460
atccggcaaa caaccaccg ctggtagcgg tggtttttt gtttgcaagc agcagattac      2520
gcgcagaaaa aaaggatctc aagaagatcc tttgatcttt tctacggggt ctgacgctca    2580
gtggaacgaa aactcacgtt aagggatttt ggtcatgaga ttatcaaaaa ggatcttcac    2640
ctagatcctt ttaaattaaa aatgaagttt taaatcaatc taaagtatat atgagtaacc    2700
tgaggctatg caggcctg ccgccccgac gttggctgcg agccctgggc cttcacccga     2760
acttgggggg tgggtgggg aaaaggaaga aacgcgggcg tattggcccc aatgggtct      2820 cggtggggta tcgacagagt gccagccctg gaccgaacc ccgcgtttat gaacaaacga     2880
cccaacaccg tgcgtttat tctgtctttt tattgccgtc atagcgcggg ttccttccgg     2940
tattgtctcc ttccgtgttt cagttagcct ccccctaggg tgggcgaaga actccagcat    3000 gagatcccg cgctggagga tcatccagcc ggcgtcccgg aaaacgattc cgaagcccaa     3060
cctttcatag aaggcggcgg tggaatcgaa atctcgtgat ggcaggttgg gcgtcgcttg    3120
gtcggtcatt tcgaacccca gagtcccgct cagaagaact cgtcaagaag gcgatagaag    3180
gcgatgcgct gcgaatcggg agcggcgata ccgtaaagca cgaggaagcg gtcagcccat    3240
tcgccgccaa gctcttcagc aatatcacgg gtagccaacg ctatgtcctg atagcggtcc    3300
gccacaccca gccggccaca gtcgatgaat ccagaaaagc ggccattttc caccatgata    3360
ttcggcaagc aggcatcgcc atgggtcacg acgagatcct cgccgtcggg catgctcgcc    3420
```

```
ttgagcctgg cgaacagttc ggctggcgcg agcccctgat gctcttgatc atcctgatcg   3480
acaagaccgg cttccatccg agtacgtgct cgctcgatgc gatgtttcgc ttggtggtcg   3540
aatgggcagg tagccggatc aagcgtatgc agccgccgca ttgcatcagc catgatggat   3600
actttctcgg caggagcaag gtgagatgac aggagatcct gccccggcac ttcgcccaat   3660
agcagccagt cccttcccgc ttcagtgaca acgtcgagca cagctgcgca aggaacgccc   3720
gtcgtggcca gccacgatag ccgcgctgcc tcgtcttgca gttcattcag ggcaccggac   3780
aggtcggtct tgacaaaaag aaccgggcgc cctgcgctg acagccggaa cacggcggca    3840
tcagagcagc cgattgtctg ttgtgcccag tcatagccga atagcctctc acccaagcg    3900
gccggagaac ctgcgtgcaa tccatcttgt tcaatcatgc gaaacgatcc tcatcctgtc   3960
tcttgatcga tctttgcaaa agcctaggcc tccaaaaaag cctcctcact acttctggaa   4020
tagctcagag gccgaggagg cggcctcggc ctctgcataa ataaaaaaaa ttagtcagcc   4080
atggggcgga gaatgggcgg aactggcgg agttaggggc gggatgggcg gagttagggg   4140
cgggactatg gttgctgact aattgagatg catgctttgc atacttctgc ctgctgggga   4200
gcctggggac tttccacacc tggttgctga ctaattgaga tgcatgcttt gcatacttct   4260
gcctgctggg gagcctgggg actttccaca ccctaactga cacacattcc acagctggtt   4320
ctttccgcct caggactctt ccttttcaa taaatcaatc taaagtatat atgagtaaac    4380
ttggtctgac agttaccaat gcttaatcag tgaggcacct atctcagcga tctgtctatt   4440
tcgttcatcc atagttgcct gactccccgt cgtgtagata actacgatac gggagggctt   4500
accatctggc cccagtgctg caatgatacc gcgagaccca cgctcaccgg ctccagattt   4560
atcagcaata accagccag ccggaagggc cgagcgcaga agtggtcctg caactttatc     4620
cgcctccatc cagtctatta ttgttgccg ggaagctaga gtaagtagtt cgccagttaa     4680
tagtttgcgc aacgttgttg ccattgctac aggcatcgtg gtgtcacgct cgtcgtttgg   4740
tatggcttca ttcagctccg gttcccaacg atcaaggcga gttacatgat cccccatgtt   4800
gtgcaaaaaa gcggttagct ccttcggtcc tccgatcgtt gtcagaagta agttggccgc   4860
agtgttatca ctcatggtta tggcagcact gcataattct cttactgtca tgccatccgt   4920
aagatgcttt tctgtgactg gtgagtactc aaccaagtca ttctgagaat agtgtatgcg   4980
gcgaccgagt tgctcttgcc cggcgtcaat acgggataat accgcgccac atagcagaac   5040
tttaaaagtg ctcatcattg gaaaacgttc ttcggggcga aaactctcaa ggatcttacc   5100
gctgttgaga tccagttcga tgtaacccac tcgtgcaccc aactgatctt cagcatcttt   5160
tactttcacc agcgtttctg ggtgagcaaa aacaggaagg caaaatgccg caaaaaaggg   5220
aataagggcg acacggaaat gttgaatact catactcttc ctttttcaat attattgaag   5280
catttatcag ggttattgtc tcatgagcgg atacatattt gaatgtattt agaaaaataa   5340
acaaataggg gttccgcgca catttccccg aaaagtgcca cctgacgcgc cctgtagcgg   5400
cgcattaagc gcggcgggtg tggtggttac gcgcagcgtg accgctacac ttgccagcgc   5460
cctagcgccc gctcctttcg ctttcttccc ttcctttctc gccacgttcg ccggctttcc   5520
ccgtcaagct ctaaatcggg ggctcccttt agggttccga tttagtgctt tacggcacct   5580
cgaccccaaa aaacttgatt agggtgatgg ttcacgtagt gggccatcgc cctgatagac   5640
ggtttttcgc cctttgacgt tggagtccac gttctttaat agtggactct gttccaaac    5700
tggaacaaca ctcaacccta tctcggtcta ttcttttgat ttataaggga ttttgccgat   5760
ttcggcctat tggttaaaaa atgagctgat ttaacaaaaa tttaacgcga attttaacaa   5820
```
aatattaacg cttacaattt ac        5842

<210> SEQ ID NO 28
<211> LENGTH: 4838
<212> TYPE: DNA
<213> ORGANISM: Artificial Sequence
<220> FEATURE:
<223> OTHER INFORMATION: pFUSEss-CHIg-mG1-B2.1a-vH

<400> SEQUENCE: 28

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc      300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgcaggttca gctgcaggag tctgggactg     660
agctggtgaa gcctggggct tcagtgaagc tgtcctgcaa ggcttctggc tacaccttca     720
ccaactactg gatgcactgg gttaagcaga ggcctggaca aggccttgag tggattggag     780
agattaatcc tagcgacggt catactaact acaatgagaa gttcaagagc aaggccacac     840
tgactgtaga caaatcctcc agcacagcct acatgcaact cagcagcctg acatctgagg     900
actctgcggt ctattactgt gcaagacctt gggcgtttgg taactacggg gcctggtttg     960
cttactgggg ccaagggact ctggtcactg tctctgccgc taaaacgaca ccccccatctg    1020
tctatccact ggcccctgga tctgctgccc aaactaactc catggtgacc ctgggatgcc    1080
tggtcaaggg ctatttccct gagccagtga cagtgacctg gaactctgga tccctgtcca    1140
gcggtgtgca caccttccca gctgtcctgc agtctgacct ctacactctg agcagctcag    1200
tgactgtccc ctccagcacc tggcccagcg agaccgtcac ctgcaacgtt gcccacccgg    1260
ccagcagcac caaggtggac aagaaaattg tgcccaggga ttgtggttgt aagccttgca    1320
tatgtacagt cccagaagta tcatctgtct tcatcttccc cccaaagccc aaggatgtgc    1380
tcaccattac tctgactcct aaggtcacgt gtgttgtggt agacatcagc aaggatgatc    1440
ccgaggtcca gttcagctgg tttgtagatg atgtggaggt gcacacagct cagacgcaac    1500
cccgggagga gcagttcaac agcactttcc gctcagtcag tgaacttccc atcatgcacc    1560
aggactggct caatggcaag gagttcaaat gcagggtcaa cagtgcagct ttccctgccc    1620
ccatcgagaa aaccatctcc aaaaccaaag gcagaccgaa ggctccacag gtgtacacca    1680
ttccacctcc caaggagcag atggccaagg ataaagtcag tctgacctgc atgataacag    1740
acttcttccc tgaagacatt actgtggagt ggcagtggaa tgggcagcca gcggagaact    1800
acaagaacac tcagcccatc atggacacag atggctctta cttcgtctac agcaagctca    1860
atgtgcagaa gagcaactgg gaggcaggaa atacttttac ctgctctgtg ttacatgagg    1920
gcctgcacaa ccaccatact gagaagagcc tctcccactc tcctggtaaa tgatcccagt    1980
```

```
gtccctagct ggccagacat gataagatac attgatgagt ttggacaaac cacaactaga    2040
atgcagtgaa aaaaatgctt tatttgtgaa atttgtgatg ctattgcttt atttgtaacc    2100
attataagct gcaataaaca agttaacaac aacaattgca ttcattttat gtttcaggtt    2160 caggggagg tgtgggaggt ttttaaagc aagtaaaacc tctacaaatg tggtatggaa      2220
ttaattctaa aatacagcat agcaaaactt taacctccaa atcaagcctc tacttgaatc    2280
cttttctgag ggatgaataa ggcataggca tcaggggctg ttgccaatgt gcattagctg    2340
tttgcagcct caccttcttt catggagttt aagatatagt gtattttccc aaggtttgaa    2400
ctagctcttc atttctttat gttttaaatg cactgacctc ccacattccc tttttagtaa    2460
aatattcaga ataatttaa atacatcatt gcaatgaaaa taaatgtttt ttattaggca     2520
gaatccagat gctcaaggcc cttcataata tcccccagtt tagtagttgg acttagggaa    2580
caaaggaacc tttaatagaa attggacagc aagaaagcga gcttctagct tatcctcagt    2640
cctgctcctc tgccacaaag tgcacgcagt tgccggccgg gtcgcgcagg gcgaactccc    2700
gcccccacgg ctgctcgccg atctcggtca tggccggccc ggaggcgtcc cggaagttcg    2760
tggacacgac ctccgaccac tcggcgtaca gctcgtccag gccgcgcacc cacacccagg    2820
ccagggtgtt gtccggcacc acctggtcct ggaccgcgct gatgaacagg gtcacgtcgt    2880
cccggaccac accggcgaag tcgtcctcca cgaagtcccg ggagaacccg agccggtcgg    2940
tccagaactc gaccgctccg cgacgtcgc gcgcggtgag caccggaacg gcactggtca     3000
acttggccat gatggctcct cctgtcagga gaggaaagag aagaaggtta gtacaattgc    3060
tatagtgagt tgtattatac tatgcagata tactatgcca atgattaatt gtcaaactag    3120
ggctgcaggg ttcatagtgc cacttttcct gcactgcccc atctcctgcc caccctttcc    3180
caggcataga cagtcagtga cttaccaaac tcacaggagg gagaaggcag aagcttgaga    3240
cagacccgcg ggaccgccga actgcgaggg gacgtggcta gggcggcttc ttttatggtg    3300
cgccggccct cggaggcagg gcgctcgggg aggcctagcg gccaatctgc ggtggcagga    3360
ggcggggccg aaggccgtgc ctgaccaatc cggagcacat aggagtctca gccccccgcc    3420
ccaaagcaag gggaagtcac gcgcctgtag cgccagcgtt ttgtgaaatg ggggcttggg    3480
ggggttgggg ccctgactag tcaaaacaaa ctcccattga cgtcaatggg gtggagactt    3540
ggaaatcccc gtgagtcaaa ccgctatcca cgcccattga tgtactgcca aaaccgcatc    3600
atcatggtaa tagcgatgac taatacgtag atgtactgcc aagtaggaaa gtcccataag    3660
gtcatgtact gggcataatg ccaggcgggc catttaccgt cattgacgtc aatagggggc    3720
gtacttggca tatgatacac ttgatgtact gccaagtggg cagtttaccg taaatactcc    3780
acccattgac gtcaatggaa agtccctatt ggcgttacta tgggaacata cgtcattatt    3840
gacgtcaatg ggcggggtc gttgggcggt cagccaggcg ggccatttac cgtaagttat    3900
gtaacgcctg caggttaatt aagaacatgt gagcaaaagg ccagcaaaag gccaggaacc    3960
gtaaaaaggc cgcgttgctg gcgtttttcc ataggctccg ccccctgac gagcatcaca     4020 aaaatcgacg ctcaagtcag aggtggcgaa acccgacagg actataaaga taccaggcgt    4080
ttccccctgg aagctccctc gtgcgctctc ctgttccgac cctgccgctt accggatacc    4140
tgtccgcctt tctcccttcg ggaagcgtgg cgctttctca tagctcacgc tgtaggtatc    4200
tcagttcggt gtaggtcgtt cgctccaagc tgggctgtgt gcacgaaccc ccgttcagc    4260 ccgaccgctg cgccttatcc ggtaactatc gtcttgagtc aacccggta agacacgact    4320 tatcgccact ggcagcagcc actggtaaca ggattagcag agcgaggtat gtaggcggtg    4380
```

-continued

| | |
|---|---|
| ctacagagtt cttgaagtgg tggcctaact acggctacac tagaagaaca gtatttggta | 4440 |
| tctgcgctct gctgaagcca gttaccttcg gaaaaagagt tggtagctct tgatccggca | 4500 |
| aacaaaccac cgctggtagc ggtggttttt ttgtttgcaa gcagcagatt acgcgcagaa | 4560 |
| aaaaaggatc tcaagaagat cctttgatct tttctacggg gtctgacgct cagtggaacg | 4620 |
| aaaactcacg ttaagggatt ttggtcatgg ctagttaatt aacatttaaa tcagcggccg | 4680 |
| caataaaata tctttatttt cattacatct gtgtgttggt tttttgtgtg aatcgtaact | 4740 |
| aacatacgct ctccatcaaa acaaaacgaa acaaaacaaa ctagcaaaat aggctgtccc | 4800 |
| cagtgcaagt gcaggtgcca gaacatttct ctatcgaa | 4838 |

<210> SEQ ID NO 29
<211> LENGTH: 2600
<212> TYPE: DNA
<213> ORGANISM: Hepatitis C virus

<400> SEQUENCE: 29

| | |
|---|---|
| gccagccccc tgatggggc gacactccac catgaatcac tcccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gataaacccg ctcaatgcct ggagatttgg gcgtgccccc | 240 |
| gcaagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaacgt aacaccaacc gtcgcccaca ggacgtcaag ttcccgggtg | 420 |
| gcggtcagat cgttggtgga gtttacttgt tgccgcgcag gggccctaga ttgggtgtgc | 480 |
| gcgcgacgag gaagacttcc gagcggtcgc aacctcgagg tagacgtcag cctatcccca | 540 |
| aggcacgtcg gcccgaggc aggacctggg ctcagcccgg gtaccttgg ccctctatg | 600 |
| gcaatgaggg ttgcgggtgg gcgggatggc tcctgtctcc ccgtggctct cggcctagct | 660 |
| ggggccccac agaccccgg cgtaggtcgc gcaatttggg taaggtcatc gatacccta | 720 |
| cgtgcggctt cgccgacctc atgggtaca taccgctcgt cggcgcccct cttggaggcg | 780 |
| ctgccagggc cctggcgcat ggcgtccggg ttctggaaga cggcgtgaac tatgcaacag | 840 |
| ggaaccttcc tggttgctct ttctctatct tccttctggc cctgctctct tgcctgactg | 900 |
| tgcccgcttc agcctaccaa gtgcgcaatt cctcggggct ttaccatgtc accaatgatt | 960 |
| gccctaactc gagtattgtg tacgaggcgg ccgatgccat cctgcacact ccgggggtgt | 1020 |
| tcccttgcgt tcgcgagggt aacgcctcga ggtgttgggt ggcggtgacc cccacggtgg | 1080 |
| ccaccaggga cggcaaactc cccacaacgc agcttgacg tcatatcgat ctgcttgtcg | 1140 |
| ggagcgccac cctctgctcg gccctctacg tggggacct gtgcgggtct gtctttcttg | 1200 |
| ttggtcaact gttttaccttc tctcccaggc gccactggac gacgcaagac tgcaattgtt | 1260 |
| ctatctatcc cggccatata acgggtcatc gcatggcatg ggatatgatg atgaactggt | 1320 |
| cccctacggc agcgttggtg gtagctcagc tgctccggat cccacaagcc atcatggaca | 1380 |
| tgatcgctgg tgctcactgg ggagtcctgg cgggcatagc gtatttctcc atggtgggga | 1440 |
| actgggcgaa ggtcctggta gtgctgctgc tatttgccgg cgtcgacgcg gaaacccacg | 1500 |
| tcaccggggg aaatgccggc cgcaccacg ctgggcttgt tggtctccctt acaccaggcg | 1560 |
| ccaagcagaa catccaactg atcaacacca acggcagttg gcacatcaat agcacggcct | 1620 |

-continued

```
tgaattgcaa tgaaagcctt aacaccggct ggttagcagg gctcttctat caacacaaat    1680
tcaactcttc aggctgtcct gagaggttgg ccagctgccg acgccttacc gattttgccc    1740
agggctgggg tcctatcagt tatgccaacg gaagcggcct cgacgaacgc ccctactgct    1800
ggcactaccc tccaagacct tgtggcattg tgcccgcaaa gagcgtgtgt ggcccggtat    1860
attgcttcac tcccagcccc gtggtggtgg gaacgaccga caggtcgggc gcgcctacct    1920
acagctgggg tgcaaatgat acggatgtct tcgtccttaa caacaccagg ccaccgctgg    1980
gcaattggtt cggttgtacc tggatgaact caactggatt caccaaagtg tgcggagcgc    2040
ccccttgtgt catcggaggg gtgggcaaca cacccttgct ctgccccact gattgcttcc    2100
gcaaacatcc ggaagccaca tactctcggt gcggctccgg tcctggatt acacccaggt     2160 gcatggtcga ctacccgtat aggctttggc actatccttg taccatcaat tacaccatat    2220
tcaaagtcag gatgtacgtg ggagggtcg agcacaggct ggaagcggcc tgcaactgga     2280
cgcggggcga acgctgtgat ctggaagaca gggacaggtc cgagctcagc ccgttgctgc    2340
tgtccaccac acagtggcag gtccttccgt gttctttcac gaccctgcca gccttgtcca    2400
ccggcctcat ccacctccac cagaacattg tggacgtgca gtacttgtac ggggtagggt    2460
caagcatcgc gtcctgggcc attaagtggg agtacgtcgt tctcctgttc cttctgcttg    2520
cagacgcgcg cgtctgctcc tgcttgtgga tgatgttact catatcccaa gcggaggcgg    2580
ctttggagaa cctcgtaata                                                2600
```

<210> SEQ ID NO 30
<211> LENGTH: 753
<212> TYPE: PRT
<213> ORGANISM: Hepatitis C virus

<400> SEQUENCE: 30

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
```

```
            195                 200                 205
Asn Ser Ser Ile Val Tyr Glu Ala Ala Asp Ala Ile Leu His Thr Pro
    210                 215                 220
Gly Cys Val Pro Cys Val Arg Glu Gly Asn Ala Ser Arg Cys Trp Val
225                 230                 235                 240
Ala Val Thr Pro Thr Val Ala Thr Arg Asp Gly Lys Leu Pro Thr Thr
                    245                 250                 255
Gln Leu Arg Arg His Ile Asp Leu Leu Val Gly Ser Ala Thr Leu Cys
            260                 265                 270
Ser Ala Leu Tyr Val Gly Asp Leu Cys Gly Ser Val Phe Leu Val Gly
            275                 280                 285
Gln Leu Phe Thr Phe Ser Pro Arg Arg His Trp Thr Thr Gln Asp Cys
            290                 295                 300
Asn Cys Ser Ile Tyr Pro Gly His Ile Thr Gly His Arg Met Ala Trp
305                 310                 315                 320
Asp Met Met Met Asn Trp Ser Pro Thr Ala Ala Leu Val Val Ala Gln
                    325                 330                 335
Leu Leu Arg Ile Pro Gln Ala Ile Met Asp Met Ile Ala Gly Ala His
                340                 345                 350
Trp Gly Val Leu Ala Gly Ile Ala Tyr Phe Ser Met Val Gly Asn Trp
            355                 360                 365
Ala Lys Val Leu Val Val Leu Leu Leu Phe Ala Gly Val Asp Ala Glu
        370                 375                 380
Thr His Val Thr Gly Gly Asn Ala Gly Arg Thr Thr Ala Gly Leu Val
385                 390                 395                 400
Gly Leu Leu Thr Pro Gly Ala Lys Gln Asn Ile Gln Leu Ile Asn Thr
                    405                 410                 415
Asn Gly Ser Trp His Ile Asn Ser Thr Ala Leu Asn Cys Asn Glu Ser
                420                 425                 430
Leu Asn Thr Gly Trp Leu Ala Gly Leu Phe Tyr Gln His Lys Phe Asn
            435                 440                 445
Ser Ser Gly Cys Pro Glu Arg Leu Ala Ser Cys Arg Arg Leu Thr Asp
    450                 455                 460
Phe Ala Gln Gly Trp Gly Pro Ile Ser Tyr Ala Asn Gly Ser Gly Leu
465                 470                 475                 480
Asp Glu Arg Pro Tyr Cys Trp His Tyr Pro Arg Pro Cys Gly Ile
                    485                 490                 495
Val Pro Ala Lys Ser Val Cys Gly Pro Val Tyr Cys Phe Thr Pro Ser
            500                 505                 510
Pro Val Val Val Gly Thr Thr Asp Arg Ser Gly Ala Pro Thr Tyr Ser
        515                 520                 525
Trp Gly Ala Asn Asp Thr Asp Val Phe Val Leu Asn Asn Thr Arg Pro
        530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Gly Val Gly Asn
                565                 570                 575
Asn Thr Leu Leu Cys Pro Thr Asp Cys Phe Arg Lys His Pro Glu Ala
            580                 585                 590
Thr Tyr Ser Arg Cys Gly Ser Gly Pro Trp Ile Thr Pro Arg Cys Met
            595                 600                 605
Val Asp Tyr Pro Tyr Arg Leu Trp His Tyr Pro Cys Thr Ile Asn Tyr
    610                 615                 620
```

```
Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile
```